(12) United States Patent
Heo et al.

(10) Patent No.: US 8,716,326 B2
(45) Date of Patent: May 6, 2014

(54) ISOINDOLINONE DERIVATIVES, PREPARATION METHOD THEREOF AND A PHARMACEUTICAL COMPOSITION COMPRISING SAME

(75) Inventors: Jung Nyoung Heo, Daejeon (KR); Bum Tae Kim, Daejeon (KR); Hyuk Lee, Seoul (KR); Sung Youn Chang, Daejeon (KR); Zang Hee Lee, Seoul (KR); Seong Hwan Kim, Daejeon (KR); Hyun-Mo Ryoo, Seoul (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 13/320,117

(22) PCT Filed: May 14, 2010

(86) PCT No.: PCT/KR2010/003060
§ 371 (c)(1),
(2), (4) Date: Nov. 11, 2011

(87) PCT Pub. No.: WO2010/131922
PCT Pub. Date: Nov. 18, 2010

(65) Prior Publication Data
US 2012/0065396 A1    Mar. 15, 2012

(30) Foreign Application Priority Data

May 15, 2009 (KR) .......................... 10-2009-0042585
May 15, 2009 (KR) .......................... 10-2009-0042691

(51) Int. Cl.
*A61K 31/4035* (2006.01)
*C07D 209/44* (2006.01)

(52) U.S. Cl.
USPC ........... 514/418; 548/452; 548/470; 548/472; 514/412; 514/416

(58) Field of Classification Search
USPC ........... 548/452, 470, 472; 514/412, 416, 418
See application file for complete search history.

(56) References Cited

U.S. PATENT DOCUMENTS

| 4,077,998 A | * | 3/1978 | Fessler et al. | 562/442 |
| 6,022,882 A | * | 2/2000 | Kim et al. | 514/350 |
| 6,051,737 A | * | 4/2000 | Kim et al. | 564/44 |

FOREIGN PATENT DOCUMENTS

| EP | 0 847 992 A1 | 6/1998 |
| EP | 1 024 134 A1 | 8/2000 |
| WO | 02/26696 A1 | 4/2002 |
| WO | 2010/028192 A1 | 3/2010 |

OTHER PUBLICATIONS

Kobashi et al (1981): STN International HCAPLUS database, Columbus (OH), accession No. 1981: 10875.*
European Patent Office, European Search Report issued in corresponding EP Application No. 10775124.0, dated Aug. 31, 2012.
Maeda et al., "Potent Histone Deacetylase Inhibitors: N-hydroxybenzamides with Antitumor Activities," Bioorganic & Medicinal Chemistry, 2004, vol. 12, pp. 4351-4360.
Remiszewski et al., "Inhibitors of Human Histone Deacetylase: Synthesis and Enzyme and Cellular Activity of Straight Chain Hydroxamates," Journal of Medicinal Chemistry, 2002, vol. 45, No. 4, pp. 753-757.
Vaisburg et al., "N-(2-Amino-phenyl)-4-(heteroarylmethyl)-benzamides as New Histone Deacetylase Inhibitors," Bioorganic & Medicinal Chemistry Letters, 2007, vol. 17, pp. 6729-6733.

* cited by examiner

*Primary Examiner* — Golam M M Shameem
(74) *Attorney, Agent, or Firm* — Sughrue Mion, PLLC

(57) ABSTRACT

The present invention relates to an amide compound or a pharmaceutically acceptable salt thereof, a preparation method thereof, and a pharmaceutical composition comprising the same. The inventive amide compound facilitates bone formation and inhibits bone loss, and is therefore useful for preventing and treating bone disorders such as osteoporosis, osteodystrophy, bone fracture, periodontal disease, Paget's disease, bone metastasis, and rheumatoid arthritis.

7 Claims, 9 Drawing Sheets
(3 of 9 Drawing Sheet(s) Filed in Color)

Control　　　　　　　Test group
　　　　　　　　　　(Example 8)

Control　　　　　　　Test group
　　　　　　　　　　(Example 8)

Control

Test group
(Example 94)

Control

Test group
(Example 94)

Control          Test group (Example 8)

ISOINDOLINONE DERIVATIVES, PREPARATION METHOD THEREOF AND A PHARMACEUTICAL COMPOSITION COMPRISING SAME

CROSS REFERENCE TO RELATED APPLICATIONS

This application is a National Stage of International Application No. PCT/KR2010/003060 filed on May 14, 2010, which claims priorities from Korean Patent Application Nos. 10-2009-0042585 and 10-2009-0042691, filed on May 15, 2009, the contents of all of which are incorporated herein by reference in their entirety.

FIELD OF THE INVENTION

The present invention relates to an amide compound which is effective in simultaneously stimulating bone formation and inhibiting bone loss, a method for the preparation thereof, and a pharmaceutical composition comprising the same.

BACKGROUND OF THE INVENTION

The amount of bone made by osteoblastic cells and the amount of bone removed or resorbed by osteoclastic cells are balanced in healthy individuals, an imbalance therebetween causing a bone disorder such as bone fracture due to the bone loss, which occurs, e.g., at a rate of over 5% per year in the vertebrae of postmenopausal women. Such symptom can to be attributable to estrogen deficiency, but the mechanism as to how the estrogen deficiency causes bone resorption still remains unresolved.

In order to treat osteoporosis, there is a need to: (a) reduce the rate of bone resorption; (b) raise the rate of bone formation; or (c) perform both (a) and (b). There have been conducted a number of studies on the effects on bone resorption of estrogen, integrin $\alpha_v\beta_3$ antagonists, cathepsin K inhibitors, and OPG/RANKL/RANK system inhibitors, while studies of the bone formation have also been carried out to examine the effects of novel parathyroid hormone products, calcium sensing receptor antagonists to control the secretion of parathyroid hormone, selective androgen receptor modulators (SARMs), growth hormone secretagogues, insulin-like growth factors, proteosome inhibitors, and TGF-β.

The administration of estrogen, bisphosphonates, calcitonin, or raloxifene has been known to be effective in delaying the bone loss. However, the administration of such a compound over a long period of time induces side effects, e.g., the death or disfunction of osteoclastic cells (Hughes et al., *Nat. Med.* 2:1132-1136, 1996; Jilka et al., *Exp. Hematol.* 23:500-506, 1995). Bisphosphonates, in particular, reduce the activity of osteoclastic cells, ultimately leading to cell death (Parfitt et al., *J. Bone Miner Res.* 11:150-159, 1996; Suzuki et al., *Endocrinology* 137:4685-4690, 1996).

Currently available therapeutic agents for osteoporosis include bisphosphonates, hormonal drugs, vitamin D, calcitonin, and calcium.

Representative bisphosphonates are alendronate (Merck and Co., Ltd.), risedronate (Hoffman-La Roche Ltd.), zoledronate (Novartis AG; EP Patent No. 275,821), ibandronate (Hoffman-La Roche Ltd.; U.S. Pat. No. 4,942,157), and minodronate (Yamanouchi Pharmaceutical Co., Ltd.; EP Patent No. 354,806), some of which are sold on the market while others are at the clinical trial stages. However, each of them exhibits a low absorption rate of 10% or less through the gastrointestinal tracts, must be administered with a large amount of water before meal, and may cause esophagitis after administration, or osteonecrosis when administered over a long period of time.

Examples of hormonal drugs are raloxifene (Eli Lilly and Co.), droloxyfene (Pfizer Inc.; EP Patent No. 54,168), lasopoxifene (Pfizer Inc., WO 97/16434), FC-1271 (homosmedical Co. and Orion Corp., WO 96/07402), TES-424 (Ligand Co. and Weyers Co., U.S. Pat. No. 5,948,775), but may induce breast and uterine cancers, and accordingly, they are used only limitedly.

Further, vitamin D is expensive and its therapeutic efficacy is not clearly established. Calcitonin is also expensive and requires a difficult method of administration, while calcium, although known to cause little side effects, is effective only for the prevention of osteoporosis and has no therapeutic effect.

It has been found that Runx domain transcription factor (Runx2) is intimately involved in the bone differentiation. Runx2 is an important transcription factor which regulates the expression of early marker alkaline phosphatase (ALP) and late marker osteocalcin (OC) (Ducy, P. et al., *Cell* 89:747-754, 1997; Mundlos, S. et al., *Cell* 89:773-779, 1997; Komori, T. et al., *Cell* 89:755-764, 1997; Otto, F. et al., *Cell* 89:765-771, 1997). The expression of Runx2 is regulated by Smads, which are signal transmitters activated by BMP (Lee, K. S., et al., *Mol. Cell. Biol.* 20:8783-8792, 2000). It has also been reported that smurf1 (Smad ubiquitin regulatory factor 1) is a causing factor of ubiquitin-mediated Runx2 protein degradation, and over-expression smurf1 in osteoblast precursor cells leads to the suppression of signal transduction and osteoblast differentiation by the action of BMP (Zhao, M. et al., *J. Biol. Chem.* 279:12854-12859, 2004; Zhao, M. et al., *J. Biol. Chem.* 278:27939-27944, 2003). In addition, it has been known that the deacylation and ubiquitination of Runx2 result in the degradation of Runx2 by proteosome, but the treatment with histon deacetylase (HDAC) inhibitor raises the transcription activity of Runx2 to enhance the bone formation (Korean Patent Publication No. 2007-0118986).

The biological usefulness of an amide compound for facilitating bone formation and inhibiting bone loss has not yet been reported. The present inventors have unexpectedly found that bone formation is enhanced and bone loss is inhibited when treated with a specific amide compound.

SUMMARY OF THE INVENTION

Accordingly, it is an object of the present invention to provide a novel amide compound that enhances both the transcription activity of Runx2 and the expression level of alkaline phosphatase, to facilitate bone formation and also to inhibit bone loss.

It is another object of the present invention to provide a method of preparing said compound.

It is a further object of the present invention to provide a pharmaceutical composition for preventing or treating a bone disorder, comprising said compound as an active ingredient.

In accordance with an aspect of the present invention, there is provided an amide compound of formula (I) and a pharmaceutically acceptable salt thereof:

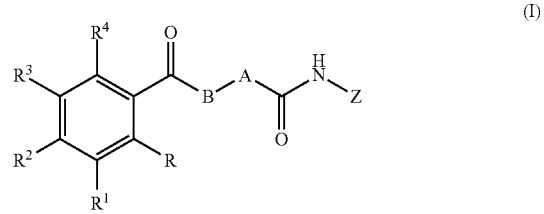

wherein,

A is $C_3$-$C_8$ alkylene or

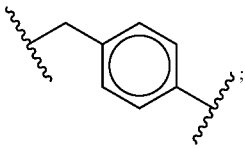

B is NH and R is selected from the group consisting of H, halogen, $C_1$-$C_6$ alkyl, $C_1$-$C_6$ alkoxy, aryl, substituted aryl, heteroaryl and substituted heteroaryl, or B and R are fused together to form an isoindolin-1-one ring;

$R^1$ to $R^4$ are each independently selected from the group consisting of H, halogen, $C_1$-$C_6$ alkyl, $C_1$-$C_6$ alkoxy, aryl, substituted aryl, heteroaryl and substituted heteroaryl;

Z is OH or

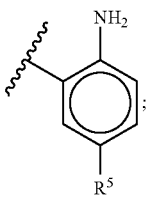

and $R^5$ is H or 2-thiophenyl.

In accordance with further aspect of the present invention, there is provided a pharmaceutical composition for preventing or treating a bone disorder, which comprises the compound of formula (I) or the pharmaceutically acceptable salt thereof as an active ingredient.

BRIEF DESCRIPTION OF THE DRAWINGS

The patent or application file contains at least one drawing executed in color. Copies of this patent or patent application publication with color drawings will be provided by the Office upon request and payment of the necessary fee.

The above and other objects and features of the present invention will become apparent from the following description of the invention, when taken in conjunction with the accompanying drawings which respectively show:

FIG. 3b: the result of evaluating bone mineral content based on the image of FIG. 3a;

FIG. 5b: the result of evaluating bone mineral content based on the image of FIG. 5a;

FIG. 6b: the result of evaluating bone mineral content based on the image of FIG. 6a.

DETAILED DESCRIPTION OF THE INVENTION

Figure 1:
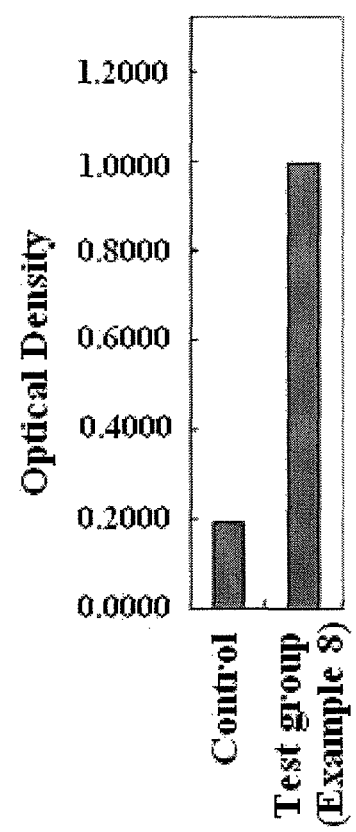
FIG. 1: the effect of the compound (Example 8) according to the present invention on the promoter activity of alkaline phosphatase, a marker of osteoblast differentiation.

Hereinafter, a detailed description of the present invention is given.

The term "halogen" refers to fluoro, bromo, chloro, or iodo.

The term "alkyl" refers to a straight or branched saturated $C_1$-$C_6$ hydrocarbon radical. Examples of alkyl include, but are not limited to, methyl, ethyl, n-propyl, isopropyl, n-butyl, isobutyl, t-butyl, n-pentyl, isopentyl, and hexyl.

The term "alkoxy" refers to —$OR_a$, wherein $R_a$ is alkyl defined above. Examples of alkoxy include, but are not limited to, methoxy, ethoxy, n-propoxy, isopropoxy, n-butoxy, isobutoxy, n-butoxy, and t-butoxy.

The term "aryl" refers to a monocyclic or bicyclic aromatic group such as phenyl and substituted phenyl as well as a fused ring aromatic group such as naphthyl and phenanthrenyl. Examples of aryl include, but are not limited to, phenyl, toluoyl, xylyl, biphenyl, and naphthyl. The term "aryl" is inclusive of an aromatic group which is substituted by one or more substituents selected from the group consisting of halogen, alkyl, alkoxy, hydroxyl, carboxy, carbamoyl, alkyloxycarbonyl, nitro, trifluoromethyl, amino, alkylcarbonylamino, cycloalkyl, cyano, alkyl $S(O)_n$ (n is 1 or 2), and thiol.

The term "heteroaryl" refers to a 5- to 10-membered heteromonocyclic aromatic group, which includes furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidinyl, pyrazinyl, pyridazinyl, 1,2,4-triazinyl, 1,2,3-triazinyl, 1,3,5-triazinyl, cinnolinyl, pteridinyl, purinyl, and 6,7-dihydro-5H-[1]pyridinyl; or a heterobicyclic aromatic group, such as 5,6,7,8-tetrahydro-quinolin-3-yl, benzo[d][1,3]dioxolyl, benzoxazolyl, benzothiazolyl, benzo[b]thiophenyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, pyrazolo[3,4-b]pyridinyl, and benzoxazinyl.

The term "pharmaceutically acceptable salts of the amide compound of formula (I)" refers to a pharmaceutically acceptable acid addition salt prepared by treating said compound with a pharmaceutically acceptable salt. Examples of the pharmaceutically acceptable salt are, but are not limited to, a salt of an inorganic acid such as hydrochloric acid, bromic acid, sulfuric acid, sodium hydrogensulfate, phosphoric acid, nitric acid, and carbonic acid; a salt of an organic acid such as formic acid, acetic acid, propionic acid, oxalic acid, succinic acid, benzoic acid, citric acid, maleic acid, malonic acid, tartaric acid, gluconic acid, lactic acid, gestisic acid, fumaric acid, lactobionic acid, salicylic acid, and acetylsalicylic acid (aspirin); a salt of an amino acid such as glycine, alanine, valine, isoleucine, serine, cysteine, cystine, aspartic acid, glutamine, lysine, arginine, tyrosine, and proline; a salt of a sulfonic acid such as methanesulfonic acid, ethanesulfonic acid, benzenesulfonic acid, and toluenesulfonic acid; a salt of an alkaline metal ion such as sodium and potassium; and an ammonium ion salt.

The present invention provides an amide compound of formula (I) or a pharmaceutically acceptable salt thereof.

Examples of preferable compounds as the amide compound according to the present invention are selected from the group consisting of the compounds of formulae (i) to (iv):

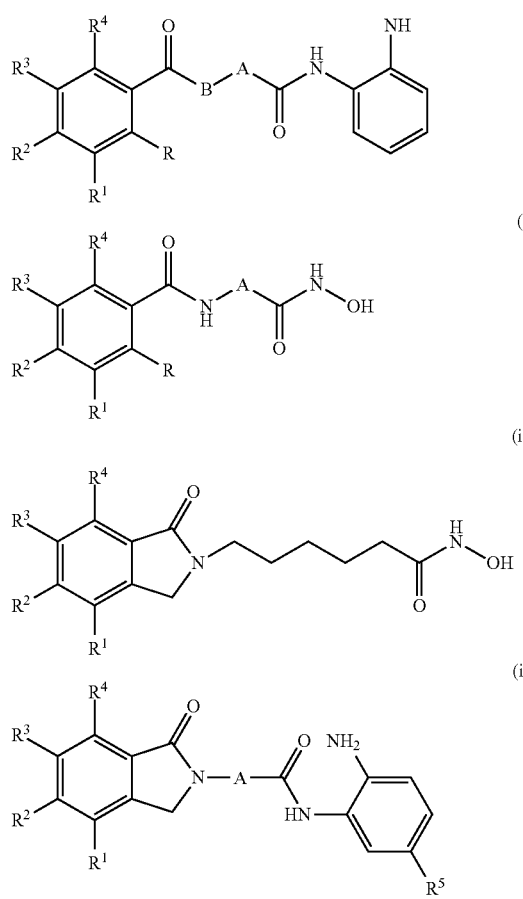

wherein A is —(CH$_2$)$_5$— or

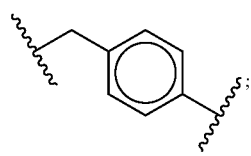

and B, R and R$^1$ to R$^5$ are defined above.

In formulae (i) to (iv), preferably one of R$^1$ to R$^4$ is selected from the group consisting of halogen, C$_1$-C$_6$ alkyl, C$_1$-C$_6$ alkoxy, aryl, substituted aryl, heteroaryl and substituted heteroaryl, and the remainder thereof being H; or R$^1$ is selected from the group consisting of halogen, C$_1$-C$_6$ alkyl, C$_1$-C$_6$ alkoxy, aryl, substituted aryl, heteroaryl and substituted heteroaryl, R$^2$ and R$^3$ are C$_1$-C$_6$ alkoxy, and R$^4$ is H.

In formula (Iv), more preferably A is

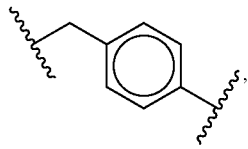

and R$^5$ is H.

In detail, preferable compounds as the amide compound according to the present invention are selected from the group consisting of:
1) N-(2-aminophenyl)-4-((4-bromo-5,6-dimethoxy-1-oxoisoindolin-2-yl)methyl)benzamide;
2) N-(2-aminophenyl)-4-((5,6-dimethoxy-1-oxo-4-phenylisoindolin-2-yl)methyl)benzamide;
3) N-(2-aminophenyl)-4-((5,6-dimethoxy-4-(3,5-dimethylphenyl)-1-oxoisoindolin-2-yl)methyl)benzamide;
4) N-(2-aminophenyl)-4-((5,6-dimethoxy-1-oxo-4-(pyridin-3-yl)isoindolin-2-yl)methyl)benzamide;
5) N-(2-aminophenyl)-4-((5,6-dimethoxy-4-(4-methoxyphenyl)-1-oxoisoindolin-2-yl)methyl)benzamide;
6) N-(2-aminophenyl)-4-(4-(4-(trifluoromethyl)phenyl)-5,6-dimethoxy-1-oxoisoindolin-2-yl)methyl)benzamide;
7) N-(2-aminophenyl)-4-((5,6-dimethoxy-4-(3,4-dimethoxyphenyl)-1-oxoisoindolin-2-yl)methyl)benzamide;
8) N-(2-aminophenyl)-4-((5,6-dimethoxy-1-oxo-4-(pyrimidin-5-yl)isoindolin-2-yl)methyl)benzamide;
9) N-(2-aminophenyl)-4-((4-bromo-1-oxoisoindolin-2-yl)methyl)benzamide;
10) N-(2-aminophenyl)-4-((1-oxo-4-(pyrimidin-5-yl)isoindolin-2-yl)methyl)benzamide;
11) N-(2-aminophenyl)-4-((1-oxo-4-phenylisoindolin-2-yl)methyl)benzamide;
12) N-(2-aminophenyl)-4-((4-(3,5-dimethylphenyl)-1-oxoisoindolin-2-yl)methyl)benzamide;
13) N-(2-aminophenyl)-4-((4-(4-trifluoromethyl)phenyl)-1-oxoisoindolin-2-yl)methyl)benzamide;
14) N-(2-aminophenyl)-4-((1-oxo-4-(pyridin-3-yl)isoindolin-2-yl)methyl)benzamide;
15) N-(2-aminophenyl)-4-((4-(4-methoxyphenyl)-1-oxoisoindolin-2-yl)methyl)benzamide;
16) N-(2-aminophenyl)-4-((4-(3,4-dimethoxyphenyl)-1-oxoisoindolin-2-yl)methyl)benzamide;
17) N-(2-aminophenyl)-4-((4-(3,5-difluorophenyl)-1-oxoisoindolin-2-yl)methyl)benzamide;
18) N-(2-aminophenyl)-4-((4-(3-aminophenyl)-1-oxoisoindolin-2-yl)methyl)benzamide;
19) N-(2-aminophenyl)-4-((4-(benzo[d][1,3]dioxol-6-yl)-1-oxoisoindolin-2-yl)methyl)benzamide;
20) N-(2-aminophenyl)-4-[4-(4-cyanophenyl)-1-oxo-2,3-dihydro-1H-isoindol-2-yl]methylbenzamide;
21) N-(2-aminophenyl)-4-((4-(naphthalen-2-yl)-1-oxoisoindolin-2-yl)methyl)benzamide;
22) N-(2-aminophenyl)-4-((4-(6-methoxypyridin-3-yl)-1-oxoisoindolin-2-yl)methyl)benzamide;
23) N-(2-aminophenyl)-4-[4-(3-acetamidophenyl)-1-oxo-2,3-dihydro-1H-isoindol-2-yl]methylbenzamide;
24) N-(2-aminophenyl)-4-((4-(3-fluoro-4-methoxyphenyl)-1-oxoisoindolin-2-yl)methyl)benzamide;
25) N-(2-aminophenyl)-4-[1-oxo-4-(4-phenylphenyl)-2,3-dihydro-1H-isoindol-2-yl]methylbenzamide;

26) 3-[2-(4-[(2-aminophenyl)carbamoyl]phenylmethyl)-1-oxo-2,3-dihydro-1H-isoindol-4-yl]benzamide;
27) N-(2-aminophenyl)-4-((4-(3-fluoro-4-methylphenyl)-1-oxoisoindolin-2-yl)methyl)benzamide;
28) 4-((4-(4-tert-butylphenyl)-1-oxoisoindolin-2-yl)methyl)-N-(2-aminophenyl)benzamide;
29) N-(2-aminophenyl)-4-((1-oxo-4-(4-phenoxyphenyl)isoindolin-2-yl)methyl)benzamide;
30) N-(2-aminophenyl)-4-((4-(4-fluorophenyl)-1-oxoisoindolin-2-yl)methyl)benzamide;
31) N-(2-aminophenyl)-6-(5,6-dimethoxy-1-oxo-4-phenyl-isoindolin-2-yl)hexanamide;
32) N-(2-aminophenyl)-6-(5,6-dimethoxy-4-(3,5-dimethylphenyl)-1-oxoisoindolin-2-yl)hexanamide;
33) N-(2-aminophenyl)-6-(5,6-dimethoxy-1-oxo-4-(pyridin-3-yl)isoindolin-2-yl)hexanamide;
34) N-(2-aminophenyl)-6-(4-(3,5-difluorophenyl)-5,6-dimethoxy-1-oxoisoindolin-2-yl)hexanamide;
35) N-(2-aminophenyl)-6-(4-(4-(trifluoromethyl)phenyl)-5,6-dimethoxy-1-oxoisoindolin-2-yl)hexanamide;
36) N-(2-aminophenyl)-6-(4-bromo-1-oxoisoindolin-2-yl)hexanamide;
37) N-(2-aminophenyl)-6-(1-oxo-4-phenylisoindolin-2-yl)hexanamide;
38) N-(2-aminophenyl)-6-(1-oxo-4-(pyridin-3-yl)isoindolin-2-yl)hexanamide;
39) N-hydroxy-6-(4-(2,4-dimethoxyphenyl)-1-oxoisoindolin-2-yl)hexanamide;
40) N-hydroxy-6-(4-(3,4-dimethoxyphenyl)-1-oxoisoindolin-2-yl)hexanamide;
41) N-hydroxy-6-(4-(3,5-dimethylphenyl)-1-oxoisoindolin-2-yl)hexanamide;
42) 6-(4-(3,5-difluorophenyl)-1-oxoisoindolin-2-yl)-N-hydroxyhexanamide;
43) N-hydroxy-6-(1-oxo-4-(pyridin-3-yl)isoindolin-2-yl)hexanamide;
44) 6-(4-(4-(trifluoromethyl)phenyl)-1-oxoisoindolin-2-yl)-N-hydroxyhexanamide;
45) N-(2-amino-5-(thiophen-2-yl)phenyl)-4-((4-bromo-1-oxoisoindolin-2-yl)methyl)benzamide;
46) N-(2-amino-5-(thiophen-2-yl)phenyl)-4-((1-oxo-4-(pyrimidin-5-yl)isoindolin-2-yl)methyl)benzamide;
47) N-(2-amino-5-(thiophen-2-yl)phenyl)-6-(1-oxo-4-(pyrimidin-5-yl)isoindolin-2-yl)hexanamide;
48) N-(2-amino-5-(thiophen-2-yl)phenyl)-4-((5,6-dimethoxy-1-oxo-4-(pyridin-3-yl)isoindolin-2-yl)methyl)benzamide;
49) N-hydroxy-6-(1-oxo-5-phenylisoindolin-2-yl)hexanamide;
50) N-hydroxy-6-(5-(2,4-dimethoxyphenyl)-1-oxoisoindolin-2-yl)hexanamide;
51) N-hydroxy-6-(5-(3,4-dimethoxyphenyl)-1-oxoisoindolin-2-yl)hexanamide;
52) N-hydroxy-6-(5-(3,5-dimethylphenyl)-1-oxoisoindolin-2-yl)hexanamide;
53) 6-(5-(3,5-difluorophenyl)-1-oxoisoindolin-2-yl)-N-hydroxyhexanamide;
54) N-hydroxy-6-(1-oxo-5-(pyridin-3-yl)isoindolin-2-yl)hexanamide;
55) 6-(5-(4-(trifluoromethyl)phenyl)-1-oxoisoindolin-2-yl)-N-hydroxyhexanamide;
56) N-(2-aminophenyl)-4-((5-bromo-1-oxoisoindolin-2-yl)methyl)benzamide;
57) N-(2-aminophenyl)-4-((1-oxo-5-phenylisoindolin-2-yl)methyl)benzamide;
58) N-(2-aminophenyl)-4-((1-oxo-5-(pyrimidin-5-yl)isoindolin-2-yl)methyl)benzamide;
59) N-(2-aminophenyl)-4-((5-(4-(trifluoromethyl)phenyl)-1-oxoisoindolin-2-yl)methyl)benzamide;
60) N-(2-aminophenyl)-4-((5-(3,5-difluorophenyl)-1-oxoisoindolin-2-yl)methyl)benzamide;
61) N-(2-aminophenyl)-4-((1-oxo-5-(pyridin-3-yl)isoindolin-2-yl)methyl)benzamide;
62) N-(2-aminophenyl)-4-((5-(3,5-dimethylphenyl)-1-oxoisoindolin-2-yl)methyl)benzamide;
63) N-(2-aminophenyl)-4-((5-(4-methoxyphenyl)-1-oxoisoindolin-2-yl)methyl)benzamide;
64) N-(2-aminophenyl)-4-((5-(3,4-dimethoxyphenyl)-1-oxoisoindolin-2-yl)methyl)benzamide;
65) N-(2-aminophenyl)-4-[5-(4-cyanophenyl)-1-oxo-2,3-dihydro-1H-isoindol-2-yl]methylbenzamide;
66) N-(2-aminophenyl)-4-((5-(benzo[d][1,3]dioxol-6-yl)-1-oxoisoindolin-2-yl)methyl)benzamide;
67) N-(2-aminophenyl)-4-((5-(naphthalen-2-yl)-1-oxoisoindolin-2-yl)methyl)benzamide;
68) N-(2-aminophenyl)-4-((3-bromo-2-methylbenzamido)methyl)benzamide;
69) N-(2-aminophenyl)-4-((2-methyl-3-phenyl-benzamido)methyl)benzamide;
70) N-(2-aminophenyl)-4-((2-methyl-3-(5-pyrimidinyl)benzamido)methyl)benzamide;
71) N-(2-aminophenyl)-4-((2-methyl-3-(3-pyridinyl)benzamido)methyl)benzamide;
72) N-(2-aminophenyl)-4-((2-methyl-3-(3-aminophenyl)benzmido)methyl)benzamide;
73) N-(2-aminophenyl)-4-((3-bromo-4,5-dimethoxy-2-methylbenzamido)methyl)benzamide;
74) N-(2-aminophenyl)-4-((2-methyl-3-phenyl-4,5-dimethoxy-benzamido)methyl)benzamide;
75) N-(2-aminophenyl)-4-((2-methyl-4,5-dimethoxy-3-(5-pyrimidinyl)-benzamido)methyl)benzamide;
76) N-(2-aminophenyl)-4-((2-methyl-3-(3-pyridinyl)-4,5-dimethoxy-benzamido)methyl)benzamide;
77) N-(2-aminophenyl)-4-((3-(3-aminophenyl)-4,5-dimethoxy-2-methyl-benzamido)methyl)benzamide;
78) N-(2-aminophenyl)-4-((2-methyl-3-(4-trifluoromethylphenyl)-4,5-dimethoxy-benzamido)methyl)benzamide;
79) N-(2-aminophenyl)-4-((2-methyl-3-(3,5-difluorophenyl)-4,5-dimethoxy-benzamido)methyl)benzamide;
80) N-(5-(2-aminophenylcarbamoyl)pentyl)-3-bromo-2-methylbenzamide;
81) N-(5-(2-aminophenylcarbamoyl)pentyl)-2-methyl-3-phenyl-benzamide;
82) N-(5-(2-aminophenylcarbamoyl)pentyl)-2-methyl-3-(2,4-dimethoxyphenyl)-benzamide;
83) N-(5-(2-aminophenylcarbamoyl)pentyl)-2-methyl-3-(3-pyridinyl)-benzamide;
84) N-(5-(2-aminophenylcarbamoyl)pentyl)-2-methyl-3-(4-pyridinyl)-benzamide;
85) N-(5-(2-aminophenylcarbamoyl)pentyl)-4-bromo-3-methylbenzamide;
86) N-(5-(2-aminophenylcarbamoyl)pentyl)-3-methyl-4-phenyl-benzamide;
87) N-(5-(2-aminophenylcarbamoyl)pentyl)-3-methyl-4-(2,4-dimethoxyphenyl)-benzamide;
88) N-(5-(2-aminophenylcarbamoyl)pentyl)-3-methyl-4-(3-pyridinyl)-benzamide;
89) N-(5-(2-aminophenylcarbamoyl)pentyl)-3-methyl-4-(4-pyridinyl)-benzamide;
90) N-(5-(2-aminophenylcarbamoyl)pentyl)-3-methyl-4-(5-pyrimidinyl)-benzamide;
91) N-(5-(2-aminophenylcarbamoyl)pentyl)-3-methyl-4-(3,5-dimethylphenyl)-benzamide;

92) N-(5-(hydroxycarbamoyl)pentyl)-2-methyl-3-phenyl-benzamide;
93) N-(5-(hydroxycarbamoyl)pentyl)-2-methyl-3-(2,4-dimethoxyphenyl)-benzamide; and
94) N-(5-(hydroxycarbamoyl)pentyl)-3-methyl-4-phenyl-benzamide.

The present invention provides a method of preparing the compound of formula (I) comprising conducting an amide coupling reaction of a compound of formula (II) with phenylene diamine or hydroxylamine hydrochloride:

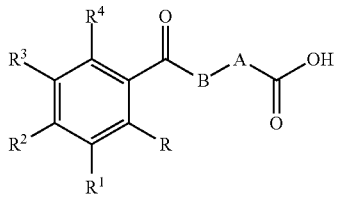
(II)

wherein A, B, R and $R^1$ to $R^4$ are defined above.

The inventive method further comprises the step of conducting a Suzuki Miyaura coupling (hereinafter refer to "Suzuki coupling reaction") using a boronic acid of formula (III) in the presence of a palladium catalyst after the amide coupling reaction, when at least one of $R^1$ to $R^4$ of formula (II) is halogen:

$R^6B(OH)_2$ (III)

wherein $R^6$ is selected from the group consisting of $C_1$-$C_6$ alkyl, aryl, substituted aryl, heteroaryl and substituted heteroaryl.

The compound of formula (II) used in the inventive method may be prepared by a method comprising the steps of:
i) subjecting a compound of formula (IV) to react with a compound of formula (V) in a solvent in the presence of a base to obtain a compound of formula (VI);
ii) hydrolyzing the compound of formula (VI),

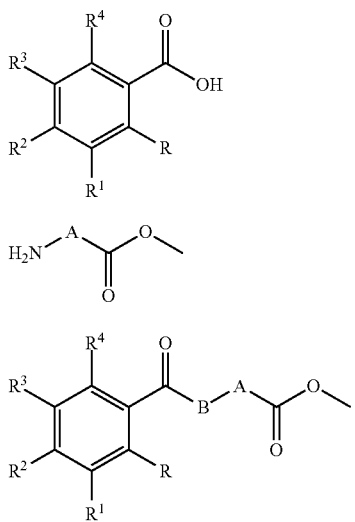

The present invention also provides a method of preparing the compound of formula (IV), comprising debenzylation of a compound of formula (V):

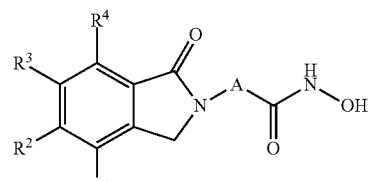
(IV)

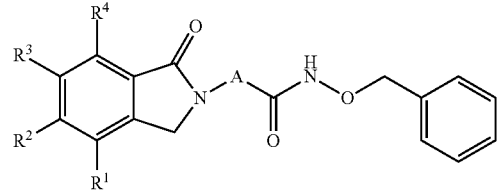
(V)

wherein A and $R^1$ to $R^4$ are defined above.

The present invention also provides a method of preparing the compound of formula (VI), comprising the steps of:
conducting an amide coupling reaction of a compound of formula (VII) with the amine compound of formula (VIII) having a butoxycarbonyl group to obtain a compound of formula (IX); and
removing the butoxycarbonyl group from the compound of formula (IX) or deprotecting the butoxycarbonyl group of the product of a Suzuki coupling reaction of the compound of formula (IX) with a boronic acid of formula (III):

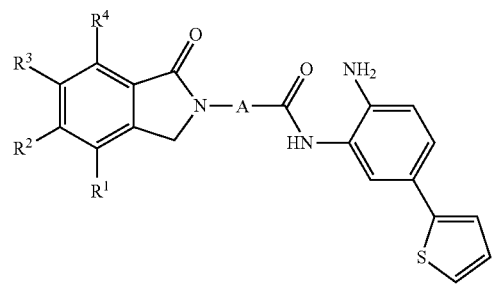
(VI)

wherein A and $R^1$ to $R^4$ are defined above;

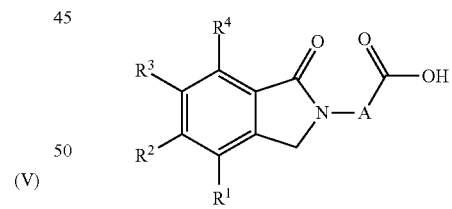
(VII)

wherein A and $R^1$ to $R^4$ are defined above, and at least one of $R^1$ to $R^4$ is halogen;

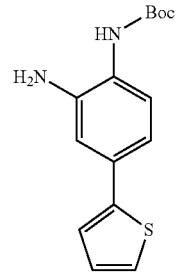
(VIII)

wherein Boc is a butoxycarbonyl group;

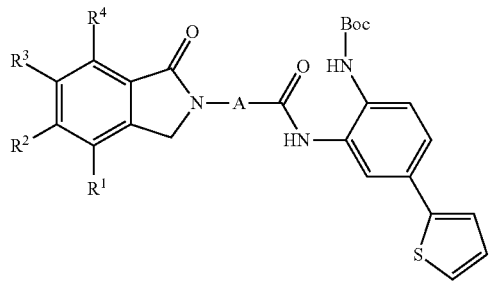 (IX)

wherein A and $R^1$ to $R^4$ are defined above, at least one of $R^1$ to $R^4$ is halogen, and Boc is a butoxycarbonyl group, $R^6B(OH)_2$  (III)

wherein $R^6$ is selected from the group consisting of $C_1$-$C_6$ alkyl, aryl, substituted aryl, heteroaryl and substituted heteroaryl.

Specifically, in case B and R are fused together to forms a 5-membered cyclic group, the amide compound of formula (I) according to the present invention may be prepared by one of the methods illustrated in Reaction Schemes 1 to 4, but not limited to them.

In an embodiment, in case B forms 5-membered cyclic group with R, Z is

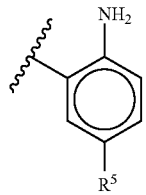

and $R^5$ is H in formula (I), the amide compound of formulae (1a) and (1b) according to the present invention may be prepared as shown in Reaction Scheme 1:

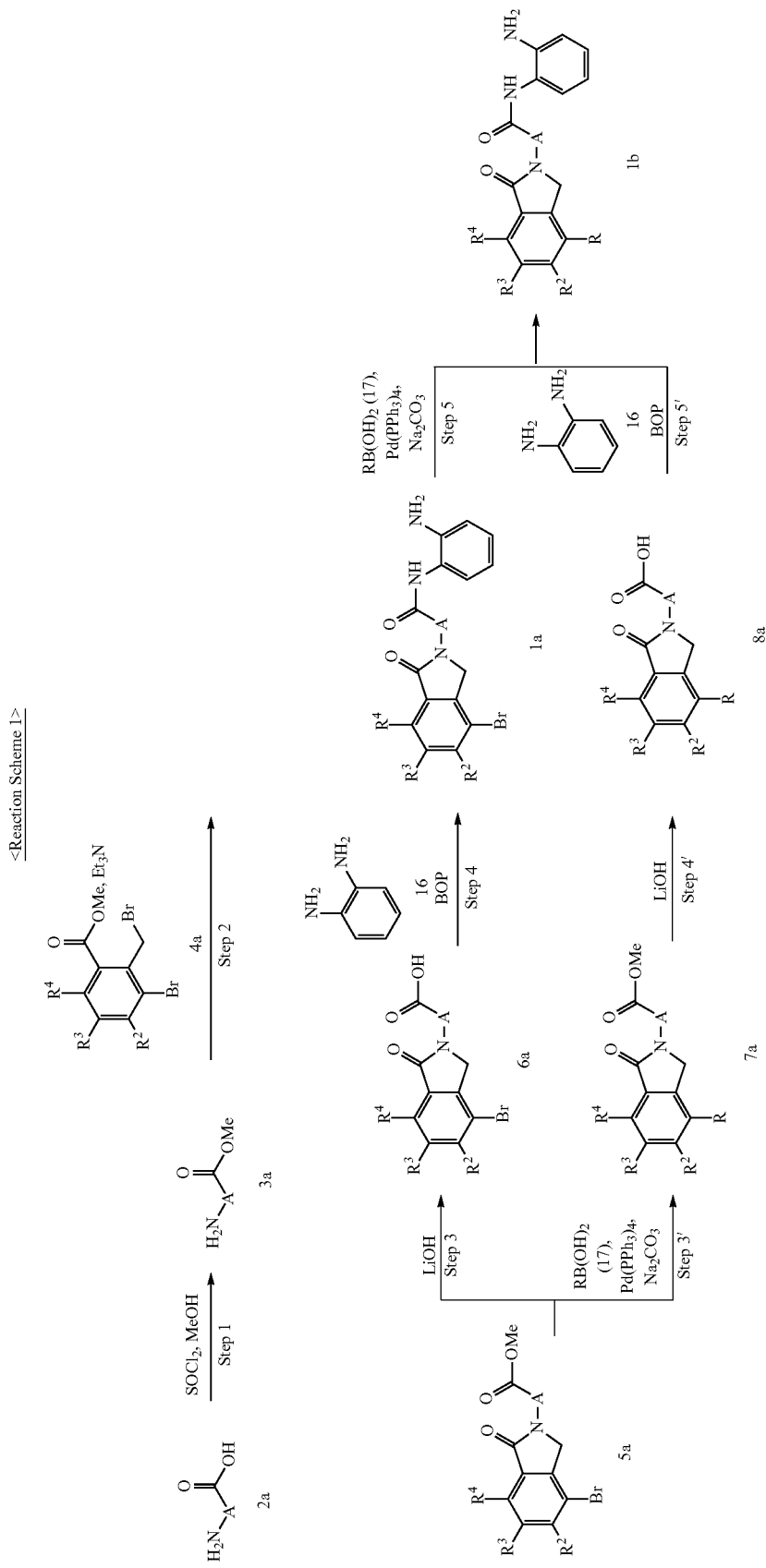

wherein,

A is defined above;

R is selected from the group consisting of $C_1$-$C_6$ alkyl, aryl, substituted aryl, heteroaryl and substituted heteroaryl; and $R^2$ to $R^4$ are each independently selected from the group consisting of H, $C_1$-$C_6$ alkyl, $C_1$-$C_6$ alkoxy, aryl, substituted aryl, heteroaryl and substituted heteroaryl.

Step 1) Esterification

A carboxylic acid of formula (2a) is dissolved in a solvent such as MeOH, thionyl chloride (2 to 3 equiv.) is added slowly thereto at 0° C., and the reacting mixture is refluxed for 12 to 24 hrs to obtain an ester of formula (3a).

Step 2) Synthesis of Isoindolinone

The ester of formula (3a) (1.5 to 2 equiv.) obtained in the step 1 and a compound of formula (4a) (e.g., methyl 3-bromo-2-(bromomethyl)-4,5-dimethoxybenzoate or methyl 3-bromo-2-(bromomethyl)benzoate) are dissolved in a solvent, preferably a mixture of tetrahydrofuran (THF) and distilled water, more preferably a 4:1 (v/v) mixture of THF and distilled water, an amine, e.g., triethylamine ($Et_3N$, 2 to 3 equiv.) is added thereto, and the reacting mixture is refluxed for 12 to 24 hrs to obtain an isoindolinone of formula (5a).

Methyl 3-bromo-2-(bromomethyl)-4,5-dimethoxybenzoate may be obtained by the method described in Kim, J. K. et al., *Org. Lett.* 10:3543-3546, 2008, and methyl 3-bromo-2-(bromomethyl)benzoate may be obtained by the method described in Curtin. M. L. et al., *Bioorg. Med. Chem. Lett.* 14:4504-4509, 2004.

Step 3) Hydrolysis

The isoindolinone of formula (5a) obtained in the step 2 and lithium hydroxide monohydrate (2 to 10 equiv.) are dissolved in a solvent, preferably a mixture of THF and distilled water, more preferably a 2:1 (v/v). mixture of THF and distilled water, and the reacting mixture is stirred for 12 to 24 hrs at room temperature to obtain a carboxylic acid of formula (6a).

Step 4) Amide Coupling Reaction

The carboxylic acid of formula (6a) obtained in the step 3,1,2-phenylenediamine of formula (16) (1.5 to 2 equiv.), and benzotriazol-1-yl oxytris(dimethylamino)phosphonium hexafluorophosphate (BOP) (1.1 to 1.5 equiv.) are dissolved in a solvent, e.g., dimethylformamide (DMF), and triethylamine (2 to 3 equiv.) is added thereto. The reacting mixture is stirred for 12 to 24 hrs at room temperature to obtain the amide compound of formula (1a) according to the present invention.

Step 5) Suzuki Coupling Reaction

The amide compound of formula (1a) obtained in the step 4, a boronic acid of formula (17) (1.1 to 1.5 equiv.), teterkis(triphenyl-phosphino)palladium (5 to 6 mol %), and sodium carbonate (2 to 3 equiv.) are dissolved in a solvent, e.g., a 4:1 (v/v). mixture of dioxane and distilled water. The reacting mixture is exposed to microwave irradiation at 150° C. to conduct a Suzuki coupling reaction for 10 to 20 minutes, to obtain the amide compound of formula (1b) according to the present invention.

The amide compound of formula (1b) according to the present invention can also be obtained by changing the order of the steps 3, 4 and 5, e.g., conducting a Suzuki coupling reaction (step 3'), hydrolysis (step 4'), and an amide coupling reaction (step 5') sequentially employing the same reaction conditions as described above.

In other embodiment, in case A is

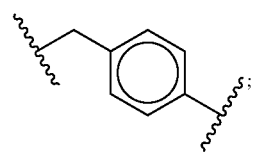

B forms 5-membered cyclic group with R, Z is

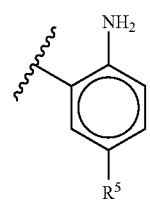

and $R^5$ is H in formula (I), the amide compound of formulae (1c) and (1d) according to the present invention may be prepared as shown in Reaction Scheme 2:

<Reaction Scheme 2>

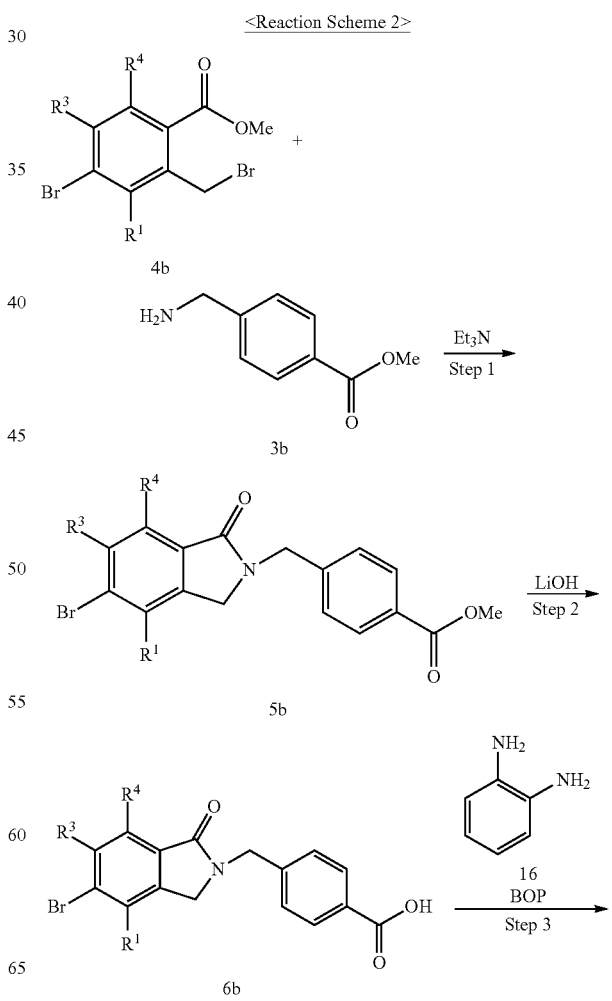

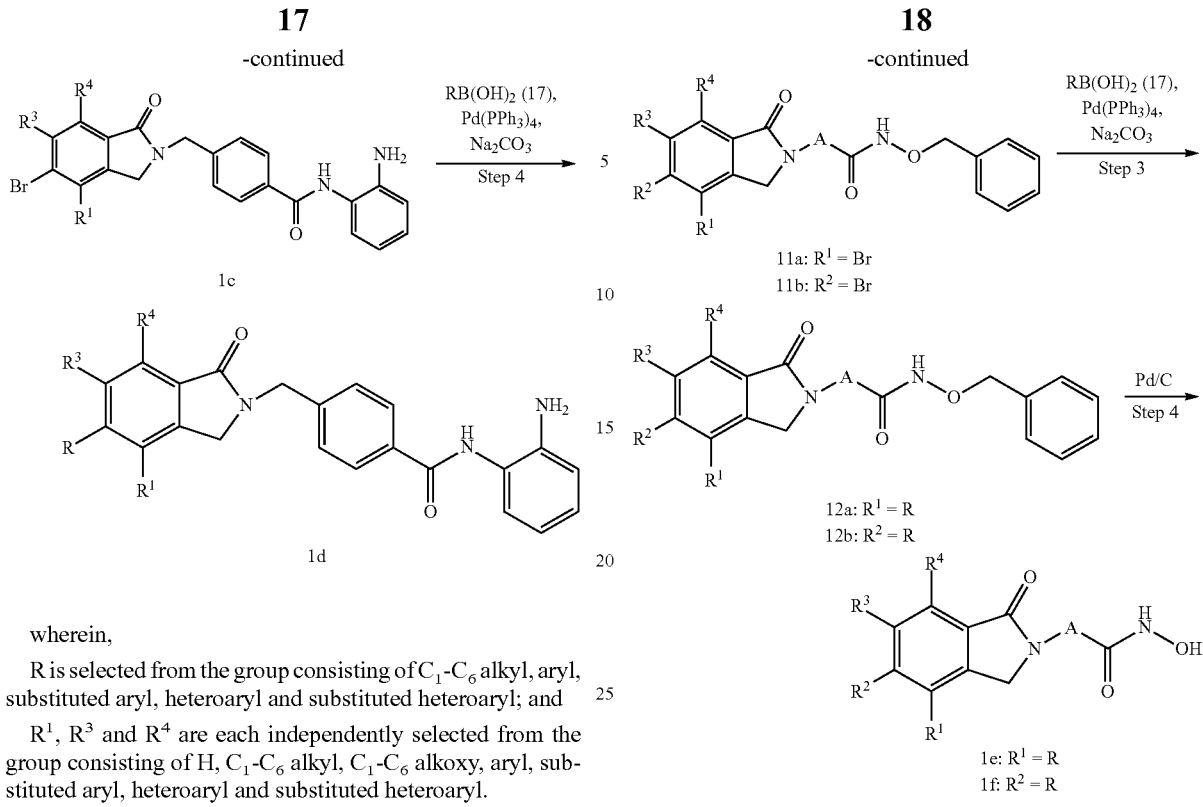

1c

1d wherein,

R is selected from the group consisting of $C_1$-$C_6$ alkyl, aryl, substituted aryl, heteroaryl and substituted heteroaryl; and $R^1$, $R^3$ and $R^4$ are each independently selected from the group consisting of H, $C_1$-$C_6$ alkyl, $C_1$-$C_6$ alkoxy, aryl, substituted aryl, heteroaryl and substituted heteroaryl.

The amide compound of formulae (1c) and (1d) according to the present invention can be prepared using the same reaction conditions and procedures as in the steps 2, 3, 4 and 5 of Reaction Scheme 1 except for using a compound of formula (4b) whose Br is substituted in the position 4 as a starting material and using an ester of formula (3b) and a bromic acid of formula (17).

In another embodiment, in case B forms 5-membered cyclic group with R and Z is OH, the amide compound of formulae (1e) and (1f) containing hydroxamic acid according to the present invention may be prepared as shown in Reaction Scheme 3:

<Reaction Scheme 3>

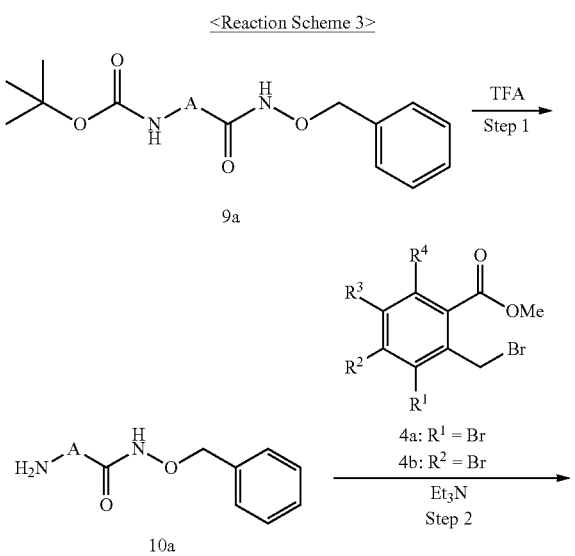

11a: $R^1$ = Br
11b: $R^2$ = Br

12a: $R^1$ = R
12b: $R^2$ = R

1e: $R^1$ = R
1f: $R^2$ = R wherein,

A is defined above;

R is selected from the group consisting of $C_1$-$C_6$ alkyl, aryl, substituted aryl, heteroaryl and substituted heteroaryl; and $R^1$ to $R^4$ are each independently selected from the group consisting of H, $C_1$-$C_6$ alkyl, $C_1$-$C_6$ alkoxy, aryl, substituted aryl, heteroaryl and substituted heteroaryl.

Step 1) Deprotection of Boc

An amine of formula (9a) protected by Boc is dissolved in a solvent such as methylene chloride, trifluoroacetic acid (TFA; 2 to 5 equiv.) is added dropwise slowly thereto at 0° C., and the reacting mixture is reacted for 3 to 24 hrs at room temperature to obtain a deprotected amine of formula (10a). The deprotection can also be conducted with a 1:1 (v/v). mixture of methylene chloride and trifluororoacetic acid.

Step 2) Synthesis of Isoindolinone

The amine of formula (10a) obtained in the step 1 is subjected to a reaction with a compound of formula (4a) or (4b) using the same reaction conditions as in the step 2 of Reaction Scheme 1 to obtain an isoindolinone of formula (11a) or (11b).

Step 3) Suzuki Coupling Reaction

A Suzuki coupling reaction is performed with the same reaction conditions as in the step 5 of Reaction Scheme 1 using the isoindolinone of formula (11a) or (11b) as a starting material to obtain an isoindolinone of formula (12a) or (12b) whose $R^1$ or $R^2$ is substituted with R.

Step 4) Debenzylation

The isoindolinone of formula (12a) or (12b) is dissolved in a solvent, e.g., a 2:1 (v/v). mixture of MeOH and EtOAc, and treated with 10% of Pd/C (5 to 10% in the weight ratio). Debenzylation is carried out under a hydrogen balloon for 2 to 10 hrs at room temperature to obtain the amide compound of formula (1e) or (1f) of the present invention.

In another embodiment, in case B forms 5-membered cyclic group with R, Z is

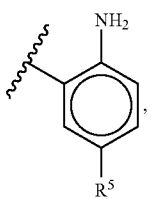

and $R^5$ is 2-thiophenyl, the amide compound of formula (1g) or (1h) of the present invention can be prepared as shown in Reaction Scheme 4:

Further, the amide of formula (14a) is subjected to a Suzuki coupling reaction using the same reaction conditions as in the step 5 of Reaction Scheme 1 (step 2'), and Boc is removed by deprotection using the same reaction conditions as in the step 1 of Reaction Scheme 3 (step 3') to obtain the amide compound of formula (1h) of the present invention.

Further, in case B is NH, the amide compound of formula (I) according to the present invention may be prepared by one of the methods illustrated in Reaction Schemes 5 to 8, but not limited to them.

In an embodiment, in case B is NH, Z is

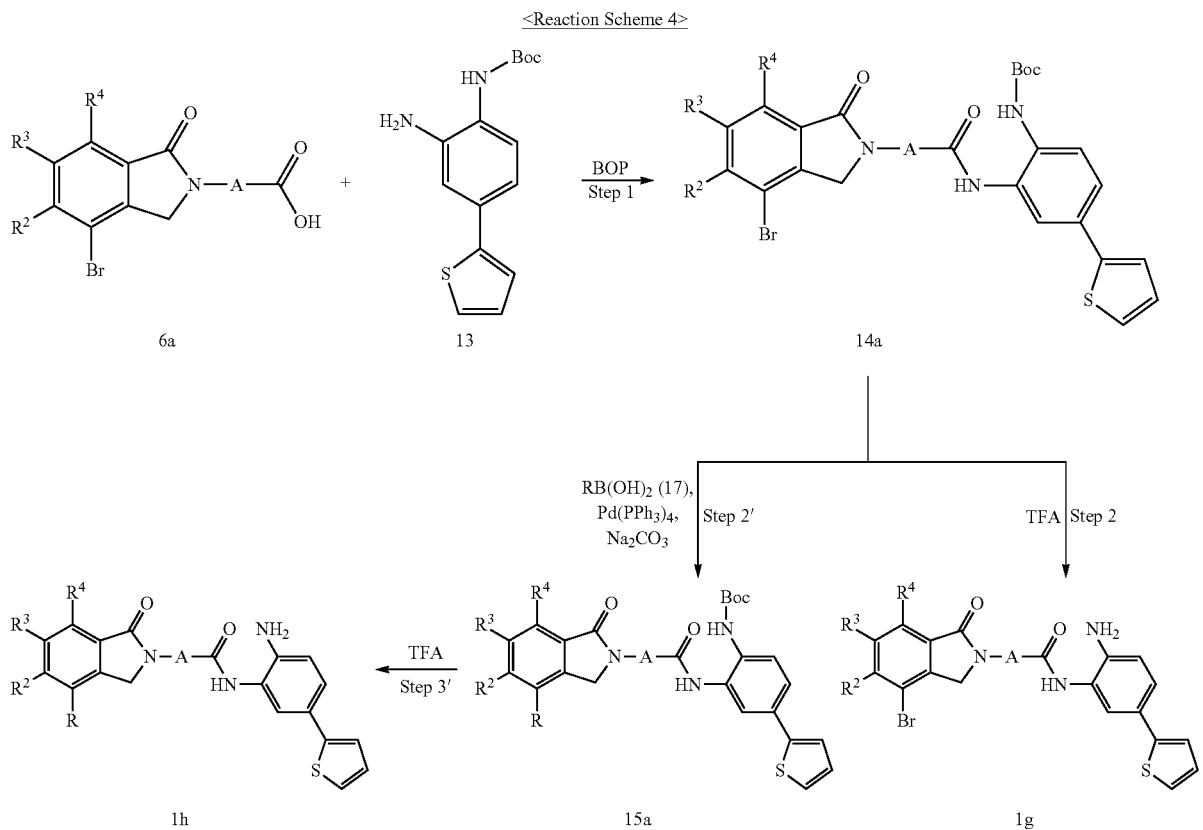

<Reaction Scheme 4> wherein,
A is defined above;
R is selected from the group consisting of $C_1$-$C_6$ alkyl, aryl, substituted aryl, heteroaryl and substituted heteroaryl;
$R^2$ to $R^4$ are each independently selected from the group consisting of H, $C_1$-$C_6$ alkyl, $C_1$-$C_6$ alkoxy, aryl, substituted aryl, heteroaryl and substituted heteroaryl; and
Boc is a butoxycarbonyl group.

Step 1) Amide Coupling Reaction

The carboxylic acid of formula (6a) obtained in the step 3 of Reaction Scheme 1 is subjected to an amide coupling reaction with an amine of formula (13) using the same reaction conditions as in the step 4 of Reaction Scheme 1 to obtain an amide of formula (14a).

Step 2) Deprotection of Boc

Deprotection of Boc is performed with the same reaction conditions as in the step 1 of Reaction Scheme 3 using the amide of formula (14a) as a starting material to obtain the isoindolinone of formula (1g) whose Boc is removed according to the present invention.

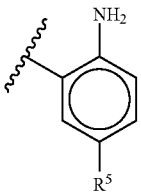

and $R^5$ is H in formula (I), the amide compound of formula (I) of the present invention may be prepared by either of the methods illustrated in Reaction Schemes 5 or 6.

Specifically, as shown in Reaction Scheme 5, the amide compound of formula (1i) may be prepared by subjecting a compound of formula (18a) to an amide coupling reaction with a compound of formula (3a) in a suitable solvent in the presence of a base to obtain a compound of formula (19a) (step 1); hydrolyzing the compound of formula (19a) to obtain a compound of formula (20a) (step 2); and conducting an amide coupling reaction of the compound of formula (20a) by Suzuki-Miyaura coupling reaction (step 3) to induce an aryl group.

The compound of formula (18a) may be prepared by the method disclosed in [Kim J. K et al., *Org. Lett.*, 10:3543-3546, 2008] or Korea patent application NO. 2007-0104435.

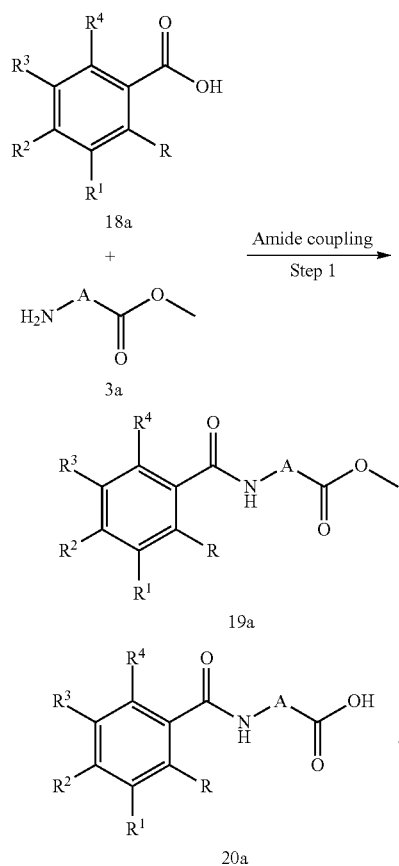

<Reaction Scheme 5>

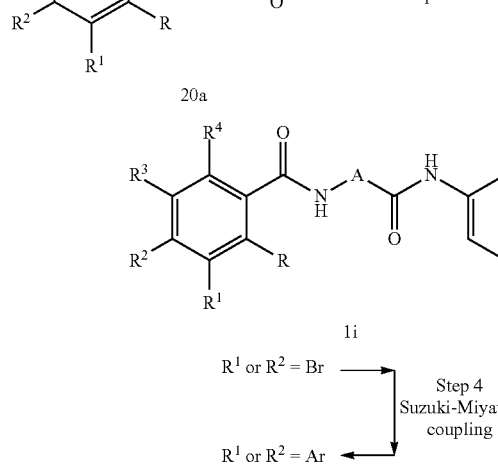

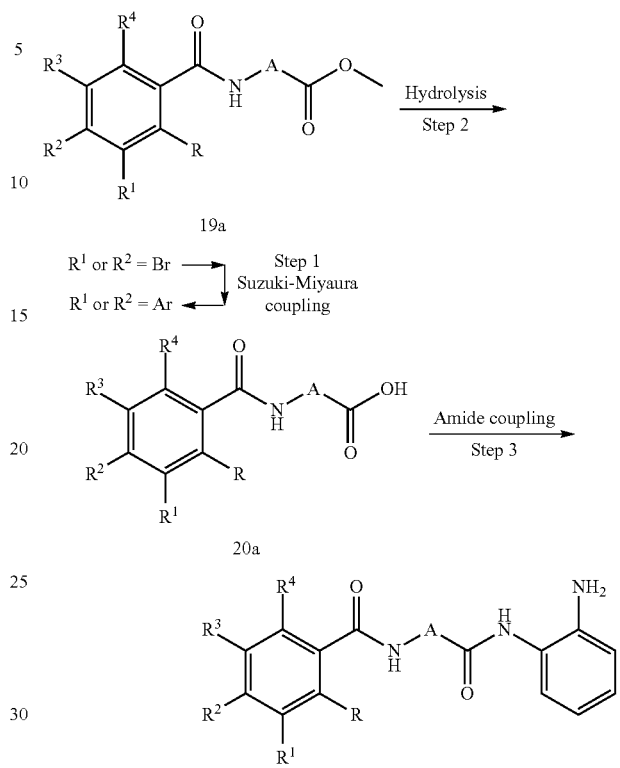

<Reaction Scheme 6> wherein, A, R, and $R^1$ to $R^4$ are defined above.

In another embodiment, in case B is NH and Z is —OH in formula (I), the amide compound of formula (1j) may be prepared by the method illustrated in Reaction Scheme 7.

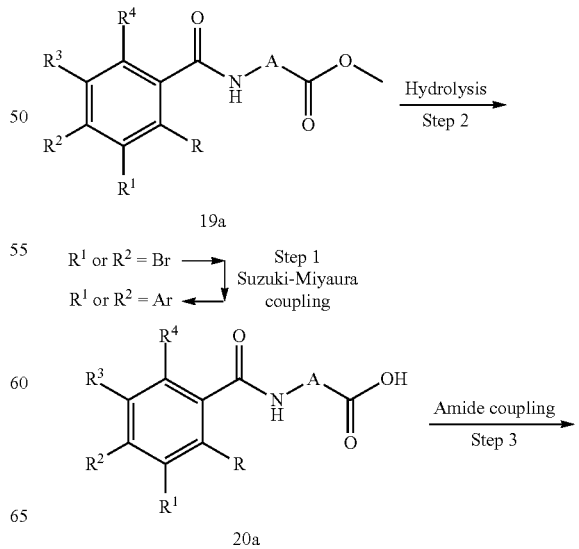

<Reaction Scheme 7> wherein, A, R, $R^1$ to $R^4$ are defined above.

Also, as shown in Reaction Scheme 6, the amide compound of formula (1i) may be prepared by introducing an aryl group to the compound of formula (19a) obtained in step (1) by Suzuki-Miyaura coupling reaction; subjecting the resulting product to hydrolysis to obtain the compound of formula (20a); and conducting an amide coupling reaction of the compound of formula (20a).

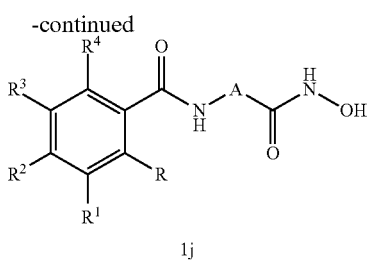

wherein, A, R, and $R^1$ to $R^4$ are defined above.

The amide compound of formulae (1k) and (1l) may be prepared by the method illustrated in Reaction Scheme 8.

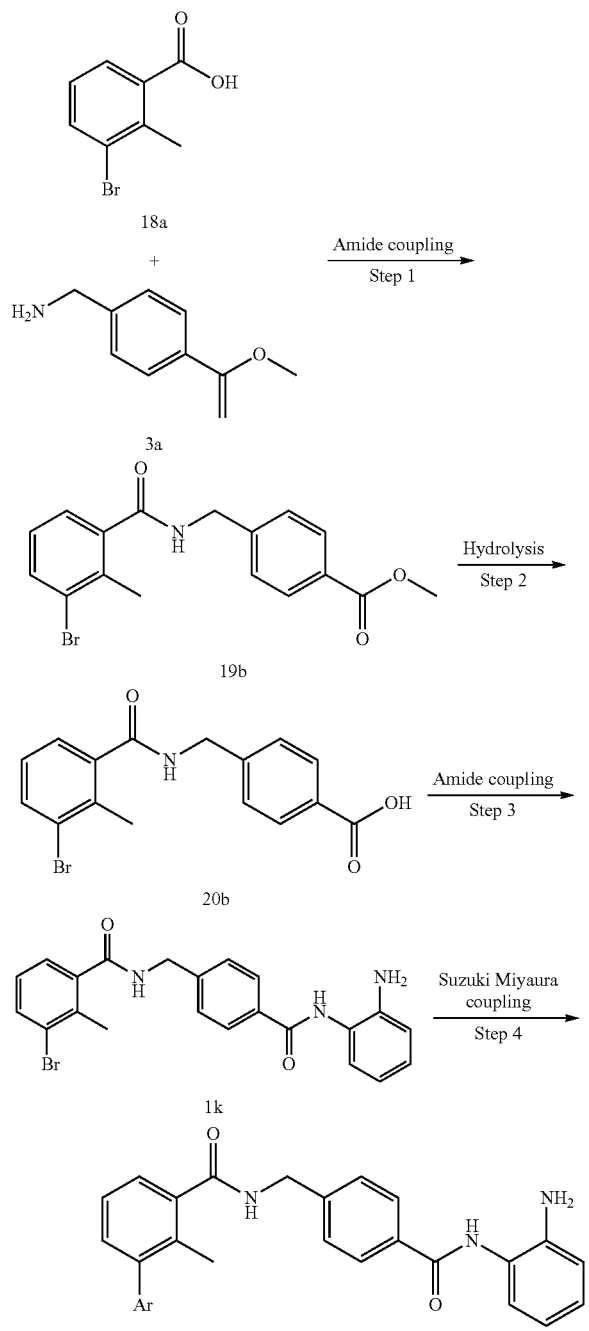

The pharmaceutically acceptable salt of the amide compound of formula (I) of the present invention can be prepared by a conventional method well-known in the art.

The pharmaceutically acceptable salt of the present invention can be prepared by dissolving the amide compound of formula (I) in a water-miscible organic solvent, such as acetone, methanol, ethanol, and acetonitrile, adding an excess amount of an organic acid or an inorganic acid with a water-soluble solvent to induce the precipitation of the salt, removing the solvent or the excess acid, and drying.

The amide compound of formula (I) of the present invention includes all hydrates and solvates thereof.

The amide compound of formula (I) and the pharmaceutically acceptable salt thereof prepared by the method of the present invention are effective in stimulating the transcription activity of Runx2 and the expression level of alkaline phosphatase to facilitate bone formation and inhibit bone loss.

Accordingly, the present invention provides an enhancer for the transcription activity of Runx2 or the expression of alkaline phosphatase.

Further, the present invention provides a pharmaceutical composition for preventing or treating a bone disorder, which comprises the amide compound of formula (I) or pharmaceutically acceptable salts thereof as an active ingredient.

The bone disorders include all disorders caused by decrease in bone formation and increase in bone loss, such as, but not limited to, osteoporosis, bone fracture, periodontal disease, osteodystrophy, Paget's disease, bone metastasis, and rheumatoid arthritis.

The pharmaceutical composition comprising the amide compound of formula (I) or the pharmaceutically acceptable salt thereof according to the present invention, upon being clinically applied, can be administered orally or parenterally and used in a pharmaceutical formulation common in the art.

The pharmaceutical composition may be formulated into a pharmaceutical preparation using a filler, an expander, a binder, a humectant, a disintegrator, a diluent such as a surfactant, or an excipient.

Solid preparations for oral administration can be prepared by mixing at least one of the amide compounds of the present invention with one or more excipients selected from starch, calcium carbonate, sucrose, lactose, and gelatin. In addition to the simple excipient, a lubricant such as magnesium stearate or talc may also be used.

Examples of liquid preparations for oral administration include suspensions, liquid solutions, emulsions, and syrups. The liquid preparations may contain a simple diluent such as water or liquid paraffin, and various excipients, such as humectants, sweetening agents, aromatic agents, and preservatives.

Examples of preparations for parenteral administration include sterilized aqueous solutions, non-liquid solutions, suspensions, emulsions, freeze-dried preparations, and suppositories. The non-liquid solutions and suspensions may be prepared using propylene glycol, polyethylene glycol, vegetable oils such as olive oil, and injectable esters such as ethyloleate. Bases for the suppositories may include Witepsol, Macrogol, Tween-61, cacao butter, laurin fat and glycerogelatin.

The dosage of the pharmaceutical composition for preventing or treating a bone disorder of the subject invention may vary depending on the conditions of the subject to be treated, including age, body weight, sex, administration route, health state, and disease severity, which typically is administered at a dose from 0.1 to 1,000 mg per day, preferably from 1 to 500 mg per day for an adult weighing 70 kg in a single dose or in divided doses per day at constant time intervals.

The following preparative examples and examples illustrate the embodiments of the present invention in more detail. However, the following preparative examples and examples of the present invention are merely examples, and the present invention is not limited thereto.

Example 1

Preparation of N-(2-aminophenyl)-4-((4-bromo-5,6-dimethoxy-1-oxoisoindolin-2-yl)methyl)benzamide Step 1: Preparation of methyl 4-(aminomethyl)benzoate hydrochloride

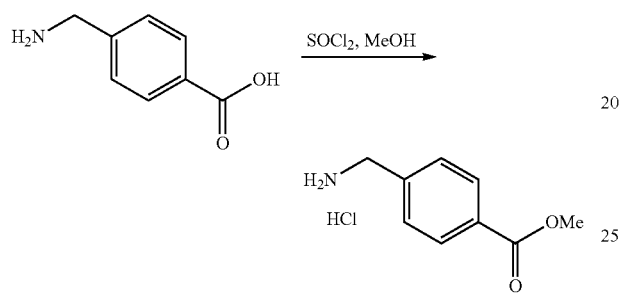

4-Aminomethylbenzoic acid (2.0 g, 13 mmol) was dissolved in MeOH (5.0 mL), thionylchloride (2.9 mL, 3 equiv.) was slowly added thereto at 0° C. and fluxed for 24 hrs. The mixture thus obtained was distilled under a reduced pressure to remove the solvent and thionyl chloride, and dried under vacuum to obtain the title compound (2.7 g, 99%).

$^1$H NMR (300 MHz, D$_2$O): δ 7.93 (d, 2H, J=8.4 Hz), 7.41 (d, 2H, J=8.4 Hz), 4.12 (s, 2H), 3.79 (s, 3H).

Step 2: Preparation of methyl 4-((4-bromo-5,6-dimethoxy-1-oxoisoindolin-2-yl)methyl)-benzoate

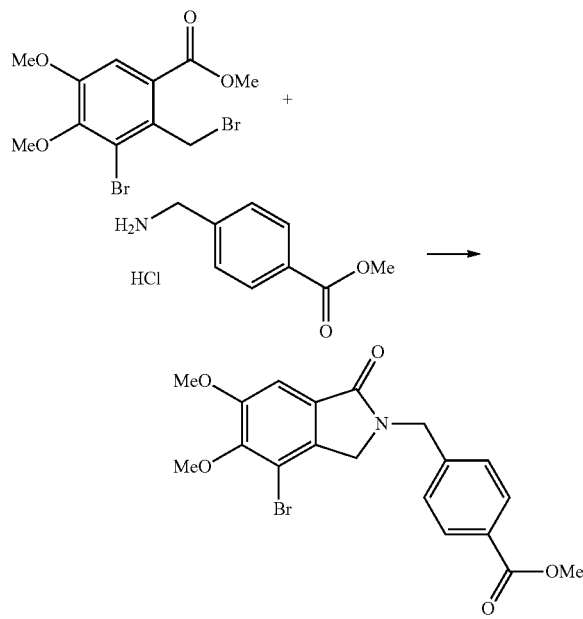

Methyl 3-bromo-2-(bromomethyl)-4,5-dimethoxybenzoate (1.5 g, 4.1 mmol) and methyl 4-(aminomethyl)benzoate hydrochloride (1.6 g, 2 equiv.) in the step 1 were dissolved in a mixture of THF and distilled water (mixture ratio=4:1 (v/v), 10 mL). Triethyl amine (1.7 mL, 3 equiv.) was added thereto and stirred at room temperature for 1 night. The reaction proceeded until no methyl 3-bromo-2-(bromomethyl)-4,5-dimethoxybenzoate was detectable by thin-layer chromatography (TLC). The resulting mixture thus obtained was distilled under a reduced pressure to remove THF. The resulting material was dissolved in ethyl acetate and washed with saturated sodium bicarbonate solution and the distilled water. The isolated organic layer was collected, dried over anhydrous MgSO$_4$, and distilled under a reduced pressure to remove solvent. The resulting residue was subjected to a silica gel column chromatography (EtOAc/hexane=1:1) to obtain the title compound (1.6 g, 93%).

$^1$H NMR (300 MHz, CDCl$_3$): δ 8.02 (d, 2H, J=8.1 Hz), 7.39 (s, 1H), 7.36 (d, 2H, J=8.1 Hz), 4.85 (s, 2H), 4.13 (s, 2H), 3.95 (s, 3H), 3.91 (s, 6H).

Step 3: Preparation of 4-((4-Bromo-5,6-dimethoxy-1-oxoisoindolin-2-yl)methyl)benzoic acid

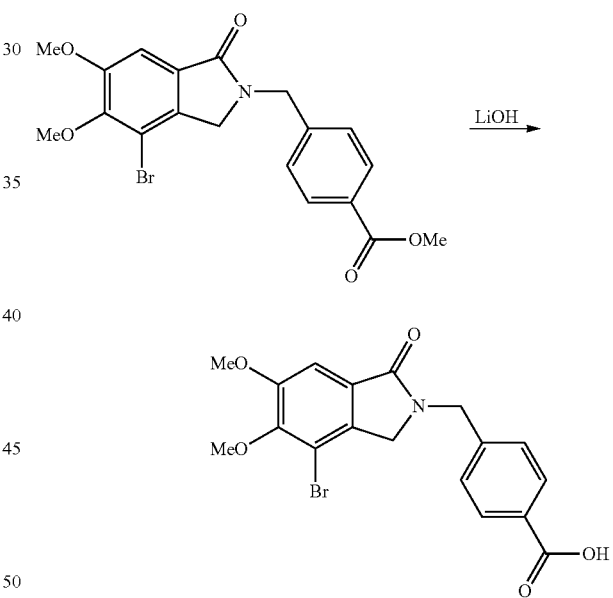

Methyl 4-((4-bromo-5,6-dimethoxy-1-oxoisoindolin-2-yl)methyl)benzoate (500 mg, 1.19 mmol) in the step 2 and lithium hydroxide monohydrate (199 mg, 4.76 mmol, 4 equiv.) were dissolved in a mixture of THF and distilled water (mixture ratio=2:1 (v/v), 10 mL), and stirred at room temperature for 1 night. The reaction proceeded until no starting material is detectable by TLC. The resulting mixture thus obtained was distilled under a reduced pressure to remove THF. The resulting material was dissolved in distilled water and 1N HCl was added thereto to be pH 2. White precipitates thus obtained were filtered and dried under vacuum to obtain the title compound (380 mg, 78%).

$^1$H NMR (300 MHz, DMSO-d$_6$): δ 7.90 (d, 2H, J=8.4 Hz), 7.37 (s, 1H), 7.36 (d, 2H, J=8.1 Hz), 4.78 (s, 2H), 4.23 (s, 2H), 3.91 (s, 3H), 3.79 (s, 3H).

Step 4: Preparation of N-(2-aminophenyl)-4-((4-bromo-5,6-dimethoxy-1-oxoisoindolin-2-yl)methyl) benzamide

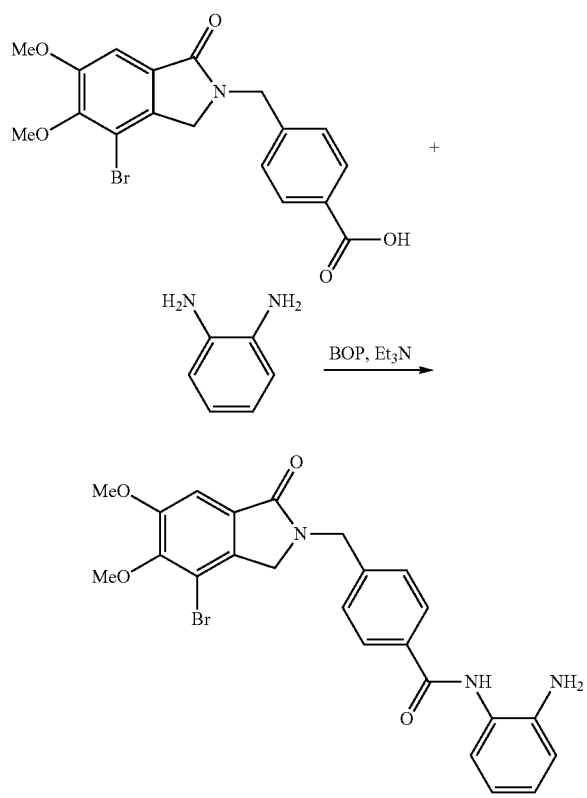

4-((4-Bromo-5,6-dimethoxy-1-oxoisoindolin-2-yl)methyl)benzoic acid (380 mg, 0.92 mmol) in the step 3, 1,2-phenylene diamine (199 mg, 1.84 mmol, 2 equiv.), and BOP (610 mg, 1.38 mmol, 1.5 equiv.) were dissolved in DMF (4 mL). Triethylamine (0.25 mL, 1.8 mmol, 2 equiv.) was added thereto, and stirred at room temperature for 1 night. The reaction proceeded until no starting material is detectable by TLC. The resulting mixture thus obtained was distilled under a reduced pressure to remove DMF. The resulting material was dissolved in methylene chloride and washed with saturated sodium bicarbonate solution. The isolated organic layer was collected, dried over anhydrous MgSO$_4$, and distilled under a reduced pressure to remove solvent. The resulting residue was subjected to a silica gel column chromatography (EtOAc/hexane=9:1) to obtain the title compound (135 mg, 29%).

$^1$H NMR (300 MHz, DMSO-d$_6$): δ 9.63 (s, 1H), 7.94 (d, 2H, J=8.1 Hz), 7.39 (d, 2H, J=8.1 Hz), 7.38 (s, 1H), 7.13 (d, 1H, J=7.2 Hz), 6.95 (td, 1H, J=7.2 Hz, 1.5 Hz), 6.75 (dd, 1H, J=8.1 Hz, 1.2 Hz), 6.58 (t, 1H, J=7.8 Hz), 4.88 (brs, 2H), 4.80 (s, 2H), 4.22 (s, 2H), 3.91 (s, 3H), 3.79 (s, 3H).

Example 2

Preparation of N-(2-aminophenyl)-4-((5,6-dimethoxy-1-oxo-4-phenylisoindolin-2-yl)methyl)benzamide

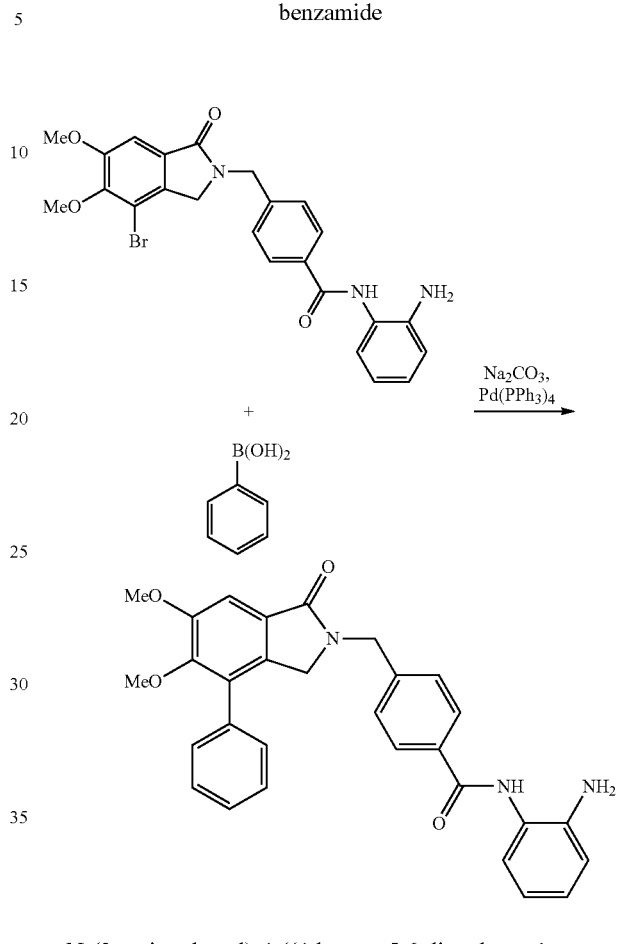

N-(2-aminophenyl)-4-((4-bromo-5,6-dimethoxy-1-oxoisoindolin-2-yl)methyl)benzamide (60 mg, 0.12 mmol) in Example 1, phenyl boronic acid (22 mg, 0.18 mmol, 1.5 equiv.), tetrakis(triphenyl-phosphino)palladium (8.4 mg, 0.0073 mmol, 6 mol %) and sodium carbonate (38 mg, 0.36 mmol, 3 equiv.) were dissolved in a mixture of dioxane and the distilled water (mixture ratio=4:1 (v/v), 5.0 mL) and the resulting solution was reacted at 150° C. under microwave for 15 mins. The resulting material thus obtained was diluted with ethyl acetate (EtOAc), dried over anhydrous MgSO$_4$, and filtered with Celite. The filtrates were distilled under a reduced pressure to remove the solvent and the resulting residue was subjected to a silica gel column chromatography (EtOAc) to obtain the title compound (55 mg, 92%).

$^1$H NMR (300 MHz, DMSO-d$_6$): δ 9.60 (s, 1H), 7.90 (d, 2H, J=8.1 Hz), 7.45-7.32 (m, 8H), 7.11 (d, 1H, J=6.9 Hz), 6.94 (td, 1H, J=7.2 Hz, 1.5 Hz), 6.74 (dd, 1H, J=7.8 Hz, 1.2 Hz), 6.56 (td, 1H, J=7.5 Hz, 1.2 Hz) 4.86 (brs, 2H), 4.73 (s, 2H), 4.09 (s, 2H), 3.93 (s, 3H), 3.56 (s, 3H).

Example 3

Preparation of N-(2-aminophenyl)-4-((5,6-dimethoxy-4-(3,5-dimethylphenyl)-1-oxoisoindolon-2-yl)methyl)benzamide The procedure of Example 2 was repeated except for using 3,5-dimethylphenyl boronic acid instead of phenyl boronic acid to obtain the title compound (90%).

¹H NMR (300 MHz, DMSO-d₆): δ 9.59 (s, 1H), 7.90 (d, 2H, J=8.1 Hz), 7.35 (s, 1H), 7.33 (d, 2H, J=8.1 Hz), 7.11 (d, 1H, J=7.2 Hz), 6.99-6.91 (m, 4H), 6.74 (dd, 1H, J=8.1 Hz, 1.5 Hz), 6.55 (td, 1H, J=8.1 Hz, 1.2 Hz), 4.86 (brs, 2H), 4.74 (s, 2H), 4.07 (s, 2H), 3.92 (s, 3H), 3.55 (s, 3H), 2.26 (s, 6H).

Example 4

Preparation of N-(2-aminophenyl)-4-((5,6-dimethoxy-1-oxo-4-(pyridin-3-yl)isoindolin-2-yl)methyl)benzamide The procedure of Example 2 was repeated except for using pyridin-3-yl-3-boronic acid instead of phenyl boronic acid to obtain the title compound (93%).

¹H NMR (300 MHz, DMSO-d₆): δ 9.60 (s, 1H), 8.60 (d, 1H, J=1.5 Hz) 8.57 (dd, 1H, J=4.8 Hz, 1.5 Hz), 7.91 (d, 2H, J=8.1 Hz), 7.85 (dt, 1H, J=8.1 Hz, 1.8 Hz), 7.47 (m, 1H), 7.43 (s, 1H), 7.35 (d, 2H, J=8.1 Hz), 7.11 (d, 1H, J=7.5 Hz), 6.94 (t, 1H, J=7.8 Hz), 6.75 (dd, 1H, J=8.1 Hz, 1.5 Hz), 6.59 (t, 1H, J=6.3 Hz), 4.85 (brs, 2H), 4.74 (s, 2H), 4.17 (s, 2H) 3.94 (s, 3H), 3.60 (s, 3H).

Example 5

Preparation of N-(2-aminophenyl)-4-((5,6-dimethoxy-4-(4-methoxyphenyl)-1-oxoisoindolin-2-yl)methyl)benzamide The procedure of Example 2 was repeated except for using 4-methoxyphenyl boronic acid instead of phenyl boronic acid to obtain the title compound (91%).

¹H NMR (300 MHz, DMSO-d₆): δ 9.60 (s, 1H), 7.91 (d, 2H, J=8.1 Hz), 7.35-7.30 (m, 5H), 7.11 (d, 1H, J=7.8 Hz), 6.99-6.92 (m, 3H), 6.74 (dd, 1H, J=8.1 Hz, 1.2 Hz), 6.56 (td, 1H, J=7.8 Hz, 1.2 Hz), 4.86 (brs, 2H), 4.74 (s, 2H), 4.10 (s, 2H), 3.91 (s, 3H), 3.76 (s, 3H), 3.54 (s, 3H).

Example 6

Preparation of N-(2-aminophenyl)-4-((4-(4-(trifluoromethyl)phenyl)-5,6-dimethoxy-1-oxoisoindolin-2-yl)methyl)benzamide The procedure of Example 2 was repeated except for using 4-(trifluoromethyl)phenyl boronic acid instead of phenyl boronic acid to obtain the title compound (92%).

¹H NMR (300 MHz, DMSO-d₆): δ 9.61 (s, 1H), 7.91 (d, 2H, J=8.1 Hz) 7.79 (d, 2H, J=8.4 Hz), 7.63 (d, 2H, J=8.4 Hz), 7.43 (s, 1H), 7.34 (d, 2H, J=8.1 Hz), 7.11 (d, 1H, J=7.2 Hz), 6.94 (td, 1H, J=8.7 Hz, 1.5 Hz), 6.75 (dd, 1H, J=8.1 Hz, 1.2 Hz), 6.56 (t, 1H, J=8.4 Hz), 4.85 (brs, 2H), 4.73 (s, 2H), 4.14 (s, 2H), 3.94 (s, 3H), 3.59 (s, 3H).

Example 7

Preparation of N-(2-aminophenyl)-4-((5,6-dimethoxy-4-(3,4-dimethoxyphenyl)-1-oxoisoindolin-2-yl)methyl)benzamide The procedure of Example 2 was repeated except for using 3,4-dimethoxyphenyl boronic acid instead of phenyl boronic acid to obtain the title compound (94%).

¹H NMR (300 MHz, DMSO-d₆): δ 9.59 (s, 1H), 7.90 (d, 2H, J=8.1 Hz), 7.37-7.33 (m, 3H), 7.11 (d, 1H, J=7.8 Hz), 6.99-6.88 (m, 4H), 6.74 (dd, 1H, J=8.1 Hz, 1.5 Hz), 6.56 (t, 1H, J=6.6 Hz), 4.85 (brs, 2H), 4.74 (s, 2H), 4.12 (s, 2H), 3.92 (s, 3H), 3.76 (s, 3H), 3.71 (s, 3H), 3.58 (s, 3H).

Example 8

Preparation of N-(2-aminophenyl)-4-((5,6-dimethoxy-1-oxo-4-(pyrimidin-5-yl)isoindolin-2-yl)methyl)benzamide The procedure of Example 2 was repeated except for using pyrimidin-5-yl-5-boronic acid instead of phenyl boronic acid to obtain the title compound (92%).

¹H NMR (300 MHz, DMSO-d₆): δ 9.61 (s, 1H), 9.20 (s, 1H), 8.90 (s, 2H), 7.91 (d, 2H, J=8.1 Hz), 7.47 (s, 1H), 7.36 (d, 2H, J=8.1 Hz), 7.11 (d, 1H, J=7.8 Hz), 6.94 (t, 1H, J=7.8 Hz), 6.75 (d, 1H, J=7.8 Hz), 6.56 (t, 1H, J=7.5 Hz), 4.85 (brs, 2H), 4.74 (s, 2H), 4.28 (s, 2H), 3.96 (s, 3H), 3.65 (s, 3H).

Example 9

Preparation of N-(2-aminophenyl)-4-((4-bromo-1-oxoisoindolin-2-yl)methyl)benzamide

Step 1: Preparation of methyl 4-((4-bromo-1-oxoisoindolin-2-yl)methyl benzoate The procedure of the step 2 in Example 1 was repeated except for using methyl 3-bromo-2-(bromomethyl)benzoate instead of methyl 3-bromo-2-(bromomethyl)-4,5-dimethoxybenzoate to obtain the title compound (95%).

¹H NMR (300 MHz, CDCl₃): δ 8.03 (d, 2H, J=8.1 Hz), 7.86 (d, 1H, J=7.5 Hz), 7.67 (d, 1H, J=8.1 Hz), 7.42 (s, 1H), 7.38 (d, 1H, J=7.8 Hz), 7.26 (s, 1H), 4.87 (s, 2H), 4.20 (s, 2H), 3.91 (s, 3H).

Step 2: Preparation of 4-((4-bromo-1-oxoisoindolin-2-yl)methyl)benzoic acid The procedure of the Step 3 in Example 1 was repeated except that methyl 4-((4-bromo-1-oxoisoindolin-2-yl)methyl)benzoate obtained in the step 1 of Example 9 instead of methyl 4-((4-bromo-5,6-dimethoxy-1-oxoisoindolin-2-yl)methyl)benzoate, and lithium hydroxide monohydrate (5 equiv.) were used and the reaction was conducted for 7 hrs, to obtain the title compound (93%).

¹H NMR (300 MHz, DMSO-d₆): δ 7.92 (d, 2H, J=8.1 Hz), 7.83 (d, 1H, J=7.8 Hz), 7.77 (d, 1H, J=6.9 Hz), 7.50 (t, 1H, J=7.5 Hz), 7.41 (d, 2H, J=8.4 Hz), 4.82 (s, 2H), 4.35 (s, 2H).

Step 3: Preparation of N-(2-aminophenyl)-4-((4-bromo-1-oxoisoindolin-2-yl)methyl)benzamide The procedure of the Step 4 in Example 1 was repeated except for using 4-((4-bromo-1-oxoisoindolin-2-yl)methyl) benzoic acid obtained in the step 2 of Example 9 instead of 4-((4-bromo-5,6-dimethoxy-1-oxoisoindolin-2-yl)methyl) benzoic acid, and 1,2-phenylene diamine (1.5 equiv.) to obtain the title compound (69%).

¹H NMR (300 MHz, DMSO-d₆): δ 9.65 (s, 1H), 7.97 (d, 2H, J=8.1 Hz), 7.84 (d, 1H, J=7.8 Hz), 7.78 (d, 1H, J=7.5 Hz), 7.51 (t, 1H, J=7.8 Hz), 7.44 (d, 2H, J=8.1 Hz), 7.15 (d, 1H,

J=7.8 Hz), 6.97 (t, 1H, J=7.8 Hz), 6.77 (d, 1H, J=7.5 Hz), 6.59 (t, 1H, J=7.2 Hz), 4.89 (brs, 2H), 4.83 (s, 2H), 4.34 (s, 2H).

Example 10

Preparation of N-(2-aminophenyl)-4-((1-oxo-4-(pyrimidin-5-yl)isoindolin-2-yl)methyl)benzamide The procedure of Example 2 was repeated except for using N-(2-aminophenyl)-4-((4-bromo-1-oxoisoindolin-2-yl)methyl)benzamide in Example 9 instead of N-(2-aminophenyl)-4-((4-bromo-5,6-dimethoxy-1-oxoisoindolin-2-yl)methyl)benzamide, and pyrimidin-5-yl-5-boronic acid instead of phenyl boronic acid to obtain the title compound (68%).

$^1$H NMR (300 MHz, DMSO-$d_6$): δ 9.64 (s, 1H), 9.24 (s, 1H), 9.08 (s, 2H), 7.95 (d, 2H, J=8.1 Hz), 7.89-7.82 (m, 2H), 7.71 (t, 1H, J=7.5 Hz), 7.43 (d, 2H, J=8.1 Hz), 7.14 (d, 1H, J=7.8 Hz), 6.96 (td, 1H, J=8.7 Hz, 1.2 Hz), 6.77 (d, 1H, J=8.1 Hz), 6.59 (t, 1H, J=7.5 Hz), 4.87 (brs, 2H), 4.82 (s, 2H), 4.67 (s, 2H).

Example 11

Preparation of N-(2-aminophenyl)-4-((1-oxo-4-phenylisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide to obtain the title compound (58%).

$^1$H NMR (300 MHz, DMSO-$d_6$): δ 9.62 (s, 1H), 7.94 (d, 2H, J=8.1 Hz), 7.78 (dd, 1H, J=6.9 Hz, 1.8 Hz), 7.69-7.62 (m, 2H), 7.57 (d, 2H, J=7.2 Hz), 7.47 (t, 2H, J=6.9 Hz), 7.43-7.40 (m, 3H), 7.13 (d, 1H, J=7.8 Hz), 6.96 (t, 1H, J=6.9 Hz), 6.76 (d, 1H, J=8.1 Hz), 6.58 (t, 1H, J=7.2 Hz), 4.87 (brs, 2H), 4.82 (s, 2H), 4.54 (s, 2H).

Example 12

Preparation of N-(2-aminophenyl)-4-((4-(3,5-dimethylphenyl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 3,5-dimethylphenyl boronic acid instead of phenyl boronic acid to obtain the title compound (84%).

$^1$H NMR (300 MHz, DMSO-$d_6$): δ 9.61 (s, 1H), 7.93 (d, 2H, J=8.1 Hz), 7.77-7.74 (m, 1H), 7.63-7.61 (m, 2H), 7.39 (d, 2H, J=8.4 Hz), 7.15-7.12 (m, 3H), 7.04 (s, 1H), 6.96 (td, 1H, J=8.1 Hz, 1.5 Hz), 6.76 (dd, 1H, J=7.8 Hz, 1.2 Hz), 6.58 (t, 1H, J=6.9 Hz), 4.86 (brs, 2H), 4.83 (s, 2H), 4.52 (s, 2H), 2.31 (s, 6H).

Example 13

Preparation of N-(2-aminophenyl)-4-((4-(4-(trifluoromethyl)phenyl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-(4-bromo-5,6-dimethoxy-1-oxoisoindolin-2-yl)methyl)benzamide, and 4-(trifluoromethyl)phenyl boronic acid instead of phenyl boronic acid to obtain the title compound (85%).

$^1$H NMR (300 MHz, DMSO-$d_6$): δ 9.63 (s, 1H), 7.95 (d, 2H, J=8.4 Hz), 7.88-7.79 (m, 5H), 7.76-7.66 (m, 2H), 7.41 (d, 2H, J=8.1 Hz), 7.13 (d, 1H, J=7.8 Hz), 6.96 (td, 1H, J=8.7 Hz, 1.5 Hz), 6.76 (d, 1H, J=7.5 Hz), 6.58 (t, 1H, J=7.5 Hz), 4.87 (brs, 2H), 4.82 (s, 2H), 4.57 (s, 2H).

Example 14

Preparation of N-(2-aminophenyl)-4-((1-oxo-4-(pyridin-3-yl)isoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and pyridin-3-yl-3-boronic acid instead of phenyl boronic acid to obtain the title compound (93%).

$^1$H NMR (300 MHz, DMSO-$d_6$): δ 9.63 (s, 1H), 8.80 (d, 1H, J=2.4 Hz), 8.62 (dd, 1H, J=4.5 Hz, 1.2 Hz), 8.03 (dt, 1H, J=6.0 Hz, 1.8 Hz), 7.94 (d, 2H, J=8.1 Hz), 7.83 (d, 1H, J=7.2 Hz), 7.75 (d, 1H, J=6.6 Hz), 7.68 (t, 1H, J=7.2 Hz), 7.51 (m, 1H), 7.42 (d, 2H, J=8.4 Hz), 7.13 (d, 1H, J=7.5 Hz), 6.96 (t, 1H, J=7.5 Hz), 6.76 (d, 1H, J=7.8 Hz), 6.58 (t, 1H, J=7.8 Hz), 4.87 (brs, 2H), 4.82 (s, 2H), 4.59 (s, 2H).

Example 15

Preparation of N-(2-aminophenyl)-4-((4-(4-methoxyphenyl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 4-methoxyphenyl boronic acid instead of phenyl boronic acid to obtain the title compound (90%).

$^1$H NMR (300 MHz, DMSO-$d_6$): δ 9.61 (s, 1H), 7.92 (d, 2H, J=8.1 Hz) 7.71 (dd, 1H, J=6.6 Hz, 2.1 Hz), 7.63-7.56 (m, 2H), 7.49 (d, 2H, J=8.7 Hz), 7.39 (d, 2H, J=8.4 Hz), 7.11 (d, 1H, J=7.2 Hz), 7.01 (d, 2H, J=8.7 Hz), 6.94 (td, 1H, J=8.4 Hz, 1.2 Hz), 6.74 (d, 1H, J=7.5 Hz), 6.56 (t, 1H, J=7.8 Hz), 4.85 (brs, 2H), 4.80 (s, 2H), 4.50 (s, 2H), 3.77 (s, 3H).

Example 16

Preparation of N-(2-aminophenyl)-4-((4-(3,4-dimethoxyphenyl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 3,4-dimethoxyphenyl boronic acid instead of phenyl boronic acid to obtain the title compound (91%).

$^1$H NMR (300 MHz, DMSO-$d_6$): δ 9.60 (s, 1H), 7.92 (d, 2H, J=8.1 Hz), 7.71 (d, 1H, J=7.8 Hz), 7.66 (d, 1H, J=7.2 Hz), 7.61-7.52 (m, 1H), 7.39 (d, 2H, J=8.1 Hz), 7.12-7.05 (m, 3H), 7.02-7.00 (m, 1H), 6.94 (td, 1H, J=8.7 Hz, 1.5 Hz), 6.74 (dd,

1H, J=7.8 Hz, 1.2 Hz), 6.56 (t, 1H, J=7.8 Hz), 4.86 (brs, 2H), 4.80 (s, 2H), 4.51 (s, 2H), 3.77 (s, 3H), 3.76 (s, 3H).

Example 17

Preparation of N-(2-aminophenyl)-4-((4-(3,5-difluorophenyl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 3,5-difluorophenyl boronic acid instead of phenyl boronic acid to obtain the title compound (82%).
$^1$H NMR (300 MHz, DMSO-$d_6$): δ 9.62 (s, 1H), 7.93 (d, 2H, J=8.4 Hz), 7.81 (dd, 1H, J=7.2 Hz, 1.2 Hz), 7.72 (dd, 1H, J=7.8 Hz, 1.2 Hz), 7.64 (t, 1H, J=7.5 Hz), 7.42-7.26 (m, 5H), 7.11 (d, 1H, J=6.9 Hz), 6.94 (td, 1H, J=8.1 Hz, 1.5 Hz), 6.75 (dd, 1H, J=7.8 Hz, 1.2 Hz), 6.56 (td, 1H, J=7.8 Hz, 1.5 Hz), 4.85 (s, 2H), 4.80 (s, 2H), 4.59 (s, 2H).

Example 18

Preparation of N-(2-aminophenyl)-4-((4-(3-aminophenyl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 3-aminophenyl boronic acid instead of phenyl boronic acid, to obtain the title compound (81%).
$^1$H NMR (300 MHz, DMSO-$d_6$): δ 9.61 (s, 1H), 7.94 (d, 2H, J=8.1 Hz), 7.73-7.71 (m, 1H), 7.59 (d, 1H, J=2.7 Hz), 7.58 (s, 1H), 7.39 (d, 2H, J=8.1 Hz), 7.10 (q, 2H, J=8.1 Hz), 6.95 (td, 1H, J=8.7 Hz, 1.5 Hz), 6.75 (dd, 1H, J=8.1 Hz, 1.2 Hz), 6.68-6.67 (m, 1H), 6.64 (d, 1H, J=7.8 Hz), 6.59-6.56 (m, 2H), 5.19 (brs, 2H), 4.86 (brs, 2H), 4.81 (s, 2H), 4.47 (s, 2H).

Example 19

Preparation of N-(2-aminophenyl)-4-((4-(benzo[d][1,3]dioxol-6-yl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and benzo[d][1,3]dioxol-5-yl-5-boronic acid instead of phenyl boronic acid, to obtain the title compound (37%).
$^1$H NMR (300 MHz, DMSO-$d_6$): δ 9.62 (s, 1H), 7.93 (d, 2H, J=8.1 Hz), 7.72 (dd, 1H, J=6.6 Hz, 2.1 Hz), 7.63-7.56 (m, 2H), 7.40 (d, 2H, J=8.1 Hz), 7.17 (s, 1H), 7.12 (d, 1H, J=6.9 Hz), 7.00 (s, 2H), 6.95 (td, 1H, J=8.7 Hz, 1.5 Hz), 6.75 (dd, 1H, J=7.8 Hz, 1.2 Hz), 6.57 (td, 1H, J=7.5 Hz, 1.2 Hz), 6.05 (s, 2H), 4.86 (s, 2H), 4.81 (s, 2H), 4.51 (s, 2H).

Example 20

Preparation of N-(2-aminophenyl)-4-[4-(4-cyanophenyl)-1-oxo-2,3-dihydro-1H-isoindol-2-yl]methylbenzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 4-cyanophenyl boronic acid instead of phenyl boronic acid, to obtain the title compound (66%).
$^1$H NMR (300 MHz, DMSO-$d_6$): δ 9.63 (s, 1H), 7.94 (dd, 3H, J=8.4 Hz, 3.0 Hz), 7.85-7.65 (m, 6H), 7.40 (d, 2H, J=8.1 Hz), 7.12 (d, 1H, J=7.5 Hz), 6.95 (td, 1H, J=8.1 Hz, 1.5 Hz), 6.76 (dd, 1H, J=7.8 Hz, 0.9 Hz), 6.58 (td, 1H, J=7.8 Hz, 1.2 Hz), 4.86 (brs, 2H), 4.81 (s, 2H), 4.57 (s, 2H).

Example 21

Preparation of N-(2-aminophenyl)-4-((4-(naphthalen-2-yl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and naphthalen-2-yl-2-boronic acid instead of phenyl boronic acid, to obtain the title compound (68%).
$^1$H NMR (300 MHz, DMSO-$d_6$): δ 9.60 (s, 1H), 8.12 (s, 1H), 8.03-7.91 (m, 5H), 7.82-7.77 (m, 2H), 7.74-7.66 (m, 2H), 7.58-7.52 (m, 2H), 7.41 (d, 2H, J=8.4 Hz), 7.11 (d, 1H, J=7.2 Hz), 6.94 (td, 1H, J=8.1 Hz, 1.2 Hz), 6.75 (dd, 1H, J=7.8 Hz, 1.2 Hz), 6.56 (td, 1H, J=7.8 Hz, 1.2 Hz), 4.84 (brs, 2H), 4.83 (s, 2H), 4.62 (s, 2H).

Example 22

Preparation of N-(2-aminophenyl)-4-((4-(6-methoxypyridin-3-yl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 6-methoxypyridin-3-yl-3-boronic acid instead of phenyl boronic acid, to obtain the title compound (68%).
$^1$H NMR (300 MHz, DMSO-$d_6$): δ 9.62 (s, 1H), 8.38 (d, 1H, J=2.1 Hz), 7.94 (dd, 3H, J=8.7 Hz, 2.4 Hz), 7.77 (dd, 1H, J=7.2 Hz, 1.5 Hz), 7.70-7.60 (m, 2H), 7.41 (d, 2H, J=8.1 Hz), 7.12 (d, 1H, J=7.8 Hz), 6.98-6.91 (m, 2H), 6.76 (dd, 1H, J=8.1 Hz, 1.5 Hz), 6.58 (td, 1H, J=7.5 Hz, 1.2 Hz), 4.86 (brs, 2H), 4.81 (s, 2H), 4.55 (s, 2H), 3.88 (s, 3H).

Example 23

Preparation of N-(2-aminophenyl)-4-[4-(3-acetamidophenyl)-1-oxo-2,3-dihydro-1H-isoindol-2-yl]methylbenzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 3-acetamidophenyl boronic acid instead of phenyl boronic acid, to obtain the title compound (54%).
$^1$H NMR (300 MHz, DMSO-$d_6$): δ 10.0 (s, 1H), 9.61 (s, 1H), 7.93 (d, 2H, J=8.1 Hz), 7.77-7.76 (m, 2H), 7.64 (d, 2H, J=4.2 Hz), 7.57 (d, 1H, J=9.3 Hz), 7.38 (t, 3H, J=8.1 Hz), 7.22 (d, 1H, J=8.1 Hz), 7.12 (d, 1H, J=7.2 Hz), 6.95 (t, 1H, J=6.6

Hz), 6.75 (d, 1H, J=7.5 Hz), 6.57 (t, 1H, J=6.9 Hz), 4.85 (brs, 2H), 4.82 (s, 2H), 4.50 (s, 2H), 2.94 (s, 3H)

Example 24

Preparation of N-(2-aminophenyl)-4-((4-(3-fluoro-4-methoxyphenyl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 3-fluoro-4-methoxyphenyl boronic acid instead of phenyl boronic acid, to obtain the title compound (51%).

$^1$H NMR (300 MHz, DMSO-d$_6$): δ 9.62 (s, 1H), 7.94 (d, 2H, J=8.1 Hz), 7.74 (d, 1H, J=6.9 Hz), 7.67-7.58 (m, 2H), 7.49 (dd, 1H, J=12.6 Hz, 2.1 Hz), 7.41 (d, 2H, J=8.1 Hz), 7.35 (dd, 1H, J=9.3 Hz, 1.2 Hz), 7.24 (t, 1H, J=8.7 Hz), 7.12 (d, 1H, J=7.8 Hz), 6.95 (t, 1H, J=7.5 Hz), 6.77 (d, 1H, J=8.1 Hz), 6.57 (t, 1H, J=7.8 Hz), 4.86 (brs, 2H), 4.81 (s, 2H), 4.54 (s, 2H), 3.86 (s, 3H)

Example 25

Preparation of N-(2-aminophenyl)-4-[1-oxo-4-(4-phenylphenyl)-2,3-dihydro-1H-isoindol-2-yl]methylbenzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and (4-phenylphenyl)boronic acid instead of phenyl boronic acid, to obtain the title compound (81%).

$^1$H NMR (300 MHz, DMSO-d$_6$): δ 9.61 (s, 1H), 7.93 (d, 2H, J=8.1 Hz), 7.79-7.65 (m, 9H), 7.48 (t, 2H, J=7.8 Hz), 7.42-7.37 (m, 3H), 7.12 (d, 1H, J=8.0 Hz), 6.94 (td, 1H, J=7.7 Hz, 1.4 Hz), 6.74 (d, 1H, J=8.0 Hz), 6.56 (td, 1H, J=7.4 Hz, 1.3 Hz), 4.85 (brs, 2H), 4.83 (s, 2H), 4.59 (s, 2H)

Example 26

Preparation of 3-[2-(4-[(2-aminophenyl)carbamoyl]phenylmethyl)-1-oxo-2,3-dihydro-1H-isoindol-4-yl]benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 3-carbamoylphenyl boronic acid instead of phenyl boronic acid, to obtain the title compound (73%).

$^1$H NMR (300 MHz, DMSO-d$_6$): δ 9.61 (s, 1H), 8.03 (s, 1H), 7.94 (t, 3H, J=6.3 Hz), 7.79 (d, 1H, J=6.3 Hz), 7.72 (d, 1H, J=6.6 Hz), 7.67-7.63 (m, 3H), 7.40 (d, 3H, J=8.1 Hz), 7.12 (d, 1H, J=7.5 Hz), 6.95 (t, 1H, J=8.1 Hz), 6.75 (dd, 1H, J=7.8 Hz, 1.2 Hz), 6.57 (t, 1H, J=7.5 Hz), 4.85 (brs, 2H), 4.81 (s, 2H), 4.55 (s, 2H).

Example 27

Preparation of N-(2-aminophenyl)-4-((4-(3-fluoro-4-methylphenyl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 3-fluoro-4-methylphenyl boronic acid instead of phenyl boronic acid, to obtain the title compound (38%).

$^1$H NMR (300 MHz, DMSO-d$_6$): δ 9.62 (s, 1H), 7.93 (d, 2H, J=8.1 Hz), 7.77 (d, 1H, J=6.9 Hz), 7.69-7.60 (m, 2H), 7.41 (d, 2H, J=7.8 Hz), 7.36 (d, 2H, J=7.5 Hz), 7.30 (d, 1H, J=7.8 Hz), 7.12 (d, 1H, J=7.8 Hz), 6.95 (t, 1H, J=7.8 Hz), 6.75 (d, 1H, J=7.2 Hz), 6.57 (t, 1H, J=7.8 Hz), 4.86 (brs, 2H), 4.81 (s, 2H), 4.55 (s, 2H), 2.26 (s, 3H).

Example 28

Preparation of 4-((4-(4-tert-butylphenyl)-1-oxoisoindolin-2-yl)methyl)-N-(2-aminophenyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 4-tert-butylphenyl boronic acid instead of phenyl boronic acid, to obtain the title compound (58%).

$^1$H NMR (300 MHz, DMSO-d$_6$): δ 9.61 (s, 1H), 7.94 (d, 2H, J=8.1 Hz), 7.75 (dd, 1H, J=6.9 Hz, 1.5 Hz), 7.67-7.62 (m, 2H), 7.49 (s, 4H), 7.41 (d, 2H, J=8.4 Hz), 7.12 (d, 1H, J=7.8 Hz), 6.95 (t, 1H, J=7.2 Hz), 6.75 (d, 1H, J=7.8 Hz), 6.57 (t, 1H, J=7.5 Hz), 4.86 (brs, 2H), 4.81 (s, 2H), 4.53 (s, 2H), 1.30 (s, 9H).

Example 29

Preparation of N-(2-aminophenyl)-4-((1-oxo-4-(4-phenoxyphenyl)isoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2-yl)methyl)benzamide, and 4-phenoxyphenyl boronic acid instead of phenyl boronic acid, to obtain the title compound (42%).

$^1$H NMR (300 MHz, DMSO-d$_6$): δ 9.62 (s, 1H), 7.94 (d, 2H, J=8.1 Hz), 7.75 (d, 1H, J=6.9 Hz), 7.68-7.56 (m, 5H), 7.41 (t, 3H, J=7.8 Hz), 7.19 (d, 1H, J=6.9 Hz), 7.12 (d, 1H, J=7.5 Hz), 7.07 (d, 4H, J=6.6 Hz), 6.95 (t, 1H, J=7.2 Hz), 6.75 (d, 1H, J=8.1 Hz), 6.57 (t, 1H, J=7.2 Hz), 4.87 (brs, 2H), 4.82 (s, 2H), 4.54 (s, 2H).

Example 30

Preparation of N-(2-aminophenyl)-4-((4-(4-fluorophenyl)-1-oxoisoindolin-2-yl)methyl)benzamide The procedure of Example 2 was repeated except for using N-(2-aminophenyl)-4-((4-bromo-1-oxoisoindolin-2-yl)methyl)benzamide obtained in Example 9 instead of N-(2-aminophenyl)-4-((4-bromo-5,6-dimethoxy-1-oxoisoindolin-2- yl)methyl)benzamide, and 4-fluorophenyl boronic acid instead of phenyl boronic acid, to obtain the title compound (29%).

$^1$H NMR (300 MHz, DMSO-d$_6$): δ 9.61 (s, 1H), 7.93 (d, 2H, J=8.1 Hz), 7.76 (dd, 1H, J=6.3 Hz, 2.1 Hz), 7.66-7.59 (m, 4H), 7.40 (d, 2H, J=8.1 Hz), 7.30 (t, 2H, J=9.0 Hz), 7.12 (d, 1H, J=6.9 Hz), 6.95 (td, 1H, J=8.1 Hz, 1.5 Hz), 6.75 (dd, 1H, J=8.1 Hz, 0.9 Hz), 6.57 (td, 1H, J=7.8 Hz, 1.2 Hz), 4.85 (brs, 2H), 4.80 (s, 2H), 4.78 (s, 2H).

Example 31

Preparation of N-(2-aminophenyl)-6-(5,6-dimethoxy-1-oxo-4-phenylisoindolin-2-yl)hexanamide Step 1: Preparation of methyl 6-(4-bromo-5,6-dimethoxy-1-oxoisoindolin-2-yl)hexanoate

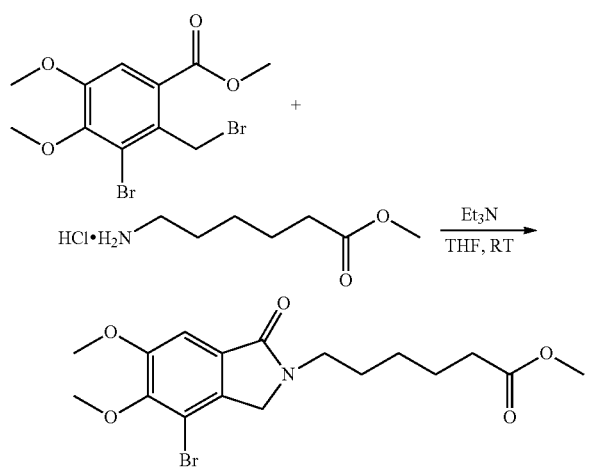

The procedure of the step 2 in Example 1 was repeated except that methyl 6-aminohexanoate hydrochloride instead of methyl 4-(aminomethyl)benzoate hydrochloride, and triethylamine (2.4 equiv.) were used and the reaction was conducted for 20 hrs, to obtain the title compound (98%).

$^1$H NMR (300 MHz, CDCl$_3$): δ 7.34 (s, 1H), 4.22 (s, 2H), 3.93 (s, 3H), 3.92 (s, 3H), 3.66 (s, 3H), 3.61 (t, 2H, J=7.395 Hz), 2.32 (t, 2H, J=7.38 Hz), 2.01-1.94 (m, 2H), 1.71-1.64 (m, 4H), 1.42-1.36 (m, 2H).

Step 2: Preparation of methyl 6-(5,6-dimethoxy-1-oxo-4-phenylisoindolin-2-yl)hexanoate

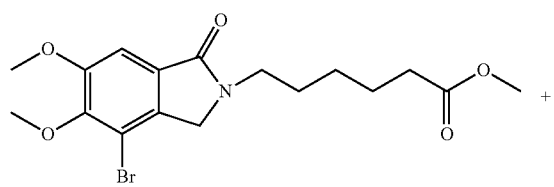

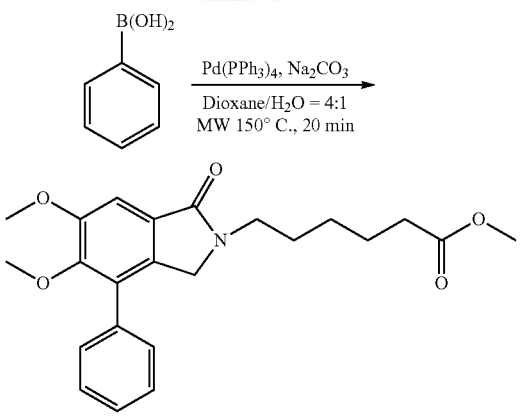

The procedure of Example 2 was repeated except that methyl 6-(4-bromo-5,6-dimethoxy-1-oxoisoindolin-2-yl) hexanoate obtained in the step 1 of Example 31 instead of N-(2-aminophenyl)-4-((4-bromo-5,6-dimethoxy-1-oxoisoindolin-2-yl)methyl)benzamide, and Na$_2$CO$_3$ (2 equiv.) were used and the reaction was conducted for 20 mins, to obtain the title compound (67%).

$^1$H NMR (300 MHz, CDCl$_3$): δ 7.42-7.30 (m, 5H), 7.19 (s, 1H), 4.05 (s, 2H), 3.89 (s, 3H), 3.56 (s, 3H), 3.54 (s, 3H), 3.48 (t, 2H, J=7.27 Hz), 2.22 (t, 2H, J=7.44 Hz), 1.60-1.52 (m, 4H), 1.20-1.24 (m, 2H)

Step 3: Preparation of 6-(5,6-dimethoxy-1-oxo-4-phenylisoindolin-2-yl)hexanoic acid

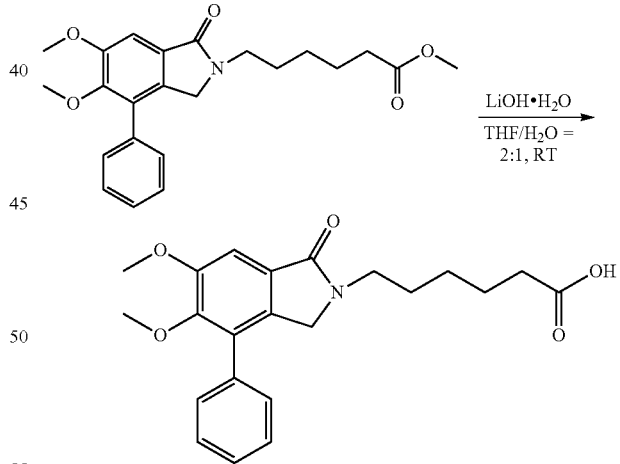

The procedure of the step 3 in Example 1 was repeated except that methyl 6-(1-oxo-4-phenylisoindolin-2-yl)hexanoate obtained in the step 2 of Example 31 instead of methyl 4-((4-bromo-5,6-dimethoxy-1-oxoisoindolin-2-yl)methyl) benzoate, and LiOH.H$_2$O (2 equiv.) were used and the reaction was conducted for 3 hrs, to obtain the title compound quantitatively.

$^1$H NMR (300 MHz, CDCl$_3$): δ 7.49-7.42 (m, 6H), 4.12 (s, 2H), 3.93 (s, 3H), 3.61 (s, 3H), 3.56 (t, 2H, J=7.275 Hz), 2.33 (t, 2H, J=7.395 Hz), 1.68-1.60 (m, 4H), 1.40-1.31 (m, 2H)

Step 4: Preparation of N-(2-aminophenyl)-6-(5,6-dimethoxy-1-oxo-4-phenylisoindolin-2-yl)hexanamide

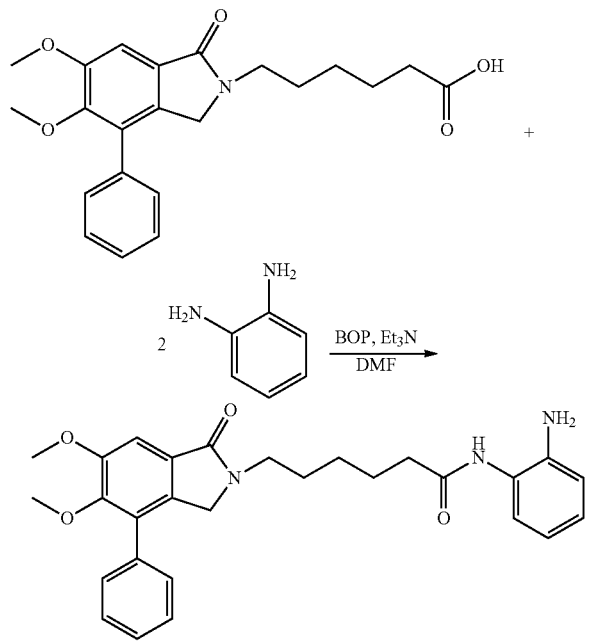

The procedure of the step 4 in Example 1 was repeated except for using 6-(5,6-dimethoxy-1-oxo-4-phenylisoindolin-2-yl)hexanoic acid obtained in the step 3 of Example 31 instead of 4-((4-bromo-5,6-dimethoxy-1-oxoisoindolin-2-yl)methyl)benzoic acid, to obtain the title compound (60%).

$^1$H NMR (300 MHz, CDCl$_3$): δ 7.54 (s, 1H), 7.49-7.37 (m, 5H), 7.30 (s, 1H), 7.19 (d, 1H, J=7.53 Hz), 7.03 (t, 1H, J=7.635 Hz), 6.77 (d, 2H, J=7.44 Hz), 4.12 (s, 2H), 3.96 (s, 2H), 3.92 (s, 3H), 3.61-3.56 (m, 5H), 2.40 (t, 2H, J=7.35 Hz), 1.83-1.77 (m, 2H), 1.68-1.63 (m, 2H), 1.44-1.38 (m, 2H)

Example 32

Preparation of N-(2-aminophenyl)-6-(5,6-dimethoxy-4-(3,5-dimethylphenyl)-1-oxoisoindolin-2-yl)hexanamide

Step 1: Preparation of methyl 6-(4-(3,5-dimethylphenyl)-5,6-dimethoxy-1-oxoisoindolin-2-yl)hexanoate

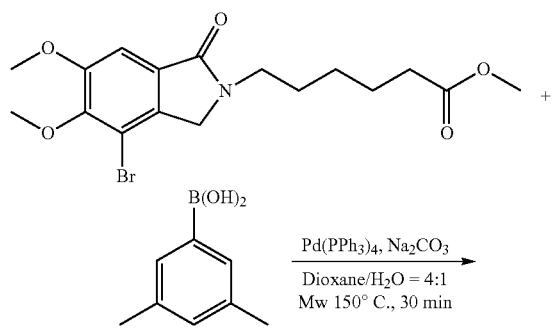

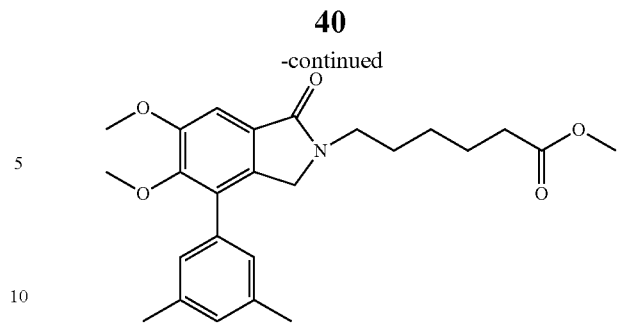

The procedure of Example 2 was repeated except for using methyl 6-(4-bromo-5,6-dimethoxy-1-oxoisoindolin-2-yl)hexanoate obtained in the step 4 of Example 31 instead of N-(2-aminophenyl)-4-((4-bromo-5,6-dimethoxy-1-oxoisoindolin-2-yl)methyl)benzamide, 3,5-dimethylphenyl boronic acid instead of phenyl boronic acid, 10 mol % of tetrakis(triphenyl-phosphino)palladium, and Na$_2$CO$_3$ (2 equiv.) to obtain the title compound (95%).

$^1$H NMR (300 MHz, CDCl$_3$): δ 7.33 (s, 1H), 6.99 (s, 1H), 6.94 (s, 2H), 4.05 (s, 2H), 3.91 (s, 3H), 3.60 (s, 6H), 3.51 (t, 2H, J=7.26 Hz), 2.33 (s, 6H), 2.25 (t, 2H, J=7.425 Hz), 1.63-1.55 (m, 4H), 1.33-1.21 (m, 2H)

Step 2: Preparation of 6-(4-(3,5-dimethylphenyl)-5,6-dimethoxy-1-oxoisoindolin-2-yl)hexanoic acid

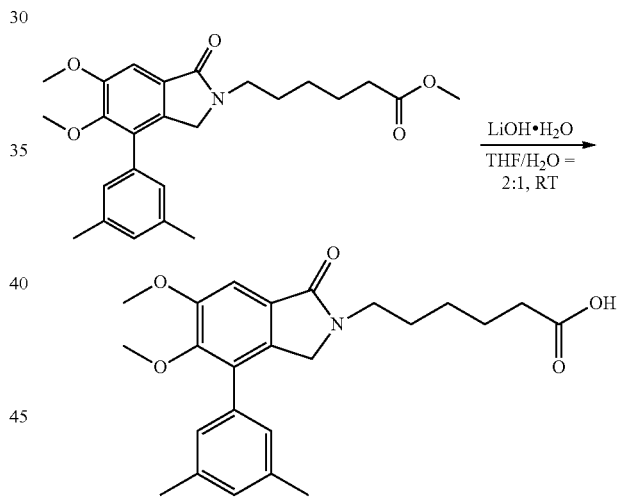

The procedure of the step 3 in Example 1 was repeated except that methyl 6-(4-(3,5-dimethylphenyl)-5,6-dimethoxy-1-oxoisoindolin-2-yl)hexanoate obtained in the step 1 of Example 32 instead of methyl 4-((4-bromo-5,6-dimethoxy-1-oxoisoindolin-2-yl)methyl)benzoate, and LiOH.H$_2$O (2 equiv.) were used and the reaction was conducted for 3 hrs, to obtain the title compound (97%).

$^1$H NMR (300 MHz, CDCl$_3$): δ7.39 (s, 1H), 7.03 (s, 1H), 6.07 (s, 2H), 4.10 (s, 2H), 3.95 (s, 3H), 3.63 (s, 3H), 3.56 (t, 2H, J=7.275 Hz), 2.37-2.31 (m, 10H), 1.68-1.59 (m, 4H), 1.40-1.31 (m, 2H)

Step 3: Preparation of N-(2-aminophenyl)-6-(5,6-dimethoxy-4-(3,5-dimethylphenyl)-1-oxoisoindolin-2-yl)hexanamide The procedure of the step 4 in Example 1 was repeated except for using 6-(4-(3,5-dimethylphenyl)-5,6-dimethoxy- 1-oxoisoindolin-2-yl)hexanoic acid obtained in the step 2 of Example 32 instead of 4-((4-bromo-5,6-dimethoxy-1-oxoisoindolin-2-yl)methyl)benzoic acid, to obtain the title compound (52%).

$^1$H NMR (300 MHz, CDCl$_3$): δ 7.50 (s, 1H), 7.28 (s, 1H), 7.19 (d, 1H, J=7.8 Hz), 7.03 (s, 2H), 6.97 (s, 2H), 6.77 (d, 2H, J=7.56 Hz), 4.10 (s, 2H), 3.95 (s, 2H), 3.93 (s, 3H), 3.63 (s, 3H), 3.59 (t, 2H, J=6.99 Hz), 2.41 (t, 2H, J=6.78 Hz), 2.37 (s, 6H), 1.83-1.78 (m, 2H), 1.68-1.64 (m, 2H), 1.44-1.39 (m, 2H)

Example 33

Preparation of N-(2-aminophenyl)-6-(5,6-dimethoxy-1-oxo-4-(pyridin-3-yl)isoindolin-2-yl) hexanamide Step 1: Preparation of methyl 6-(5,6-dimethoxy-1-oxo-4-(pyridin-3-yl)isoindolin-2-yl)hexanoate The procedure of Example 2 was repeated except for using methyl 6-(4-bromo-5,6-dimethoxy-1-oxoisoindolin-2-yl)hexanoate obtained in the step 1 of Example 31 instead of N-(2-aminophenyl)-4-((4-bromo-5,6-dimethoxy-1-oxoisoindolin-2-yl)methyl)benzamide, 3-pyridyl boronic acid acid instead of phenyl boronic acid, 10 mol % of tetrakis (triphenyl-phosphino)palladium, and Na$_2$CO$_3$ (2 equiv.), to obtain the title compound (53%).

$^1$H NMR (300 MHz, CDCl$_3$): δ 8.66 (s, 1H), 7.76 (d, 1H, J=7.5 Hz), 7.66 (dd, 1H, J=7.47 Hz, 11.34 Hz), 7.47-7.39 (m, 2H), 4.14 (s, 2H), 3.96 (s, 3H), 3.64 (s, 3H), 3.63 (s, 3H), 3.56 (t, 2H, J=7.2 Hz), 2.29 (t, 2H, J=7.32 Hz), 1.63-1.59 (m, 4H), 1.39-1.29 (m, 2H)

Step 2: Preparation of 6-(5,6-dimethoxy-1-oxo-4-(pyridin-3-yl)isoindolin-2-yl)hexanoic acid The procedure of the step 3 in Example 1 was repeated except that methyl 6-(5,6-dimethoxy-1-oxo-4-(pyridin-3-yl) isoindolin-2-yl)hexanoate obtained in the step 1 of Example 33 instead of methyl 4-((4-bromo-5,6-dimethoxy-1-oxoisoindolin-2-yl)methyl)benzoate, and LiOH.H$_2$O (2 equiv.) were used and the reaction was conducted for 4 hrs, to obtain the title compound (55%).

$^1$H NMR (300 MHz, CDCl$_3$): δ 9.16 (s, 1H), 8.81 (s, 1H), 8.56 (m, 1H), 8.02 (s, 1H), 7.55 (s, 1H), 4.61 (s, 2H), 4.00 (s, 3H), 3.69 (s, 3H), 3.65-3.60 (m, 2H), 2.40 (m, 2H), 1.86-1.77 (m, 4H), 1.65-1.50 (m, 2H)

Step 3: Preparation of N-(2-aminophenyl)-6-(5,6-dimethoxy-1-oxo-4-(pyridin-3-yl)isoindolin-2-yl) hexanamide The procedure of the step 4 in Example 1 was repeated except for using 6-(5,6-dimethoxy-1-oxo-4-(pyridin-3-yl) isoindolin-2-yl)hexanoic acid obtained in the step 2 of Example 33 instead of 4-((4-bromo-5,6-dimethoxy-1-oxoisoindolin-2-yl)methyl)benzoic acid, to obtain the title compound (85%).

$^1$H NMR (300 MHz, DMSO-d$_6$): δ 9.03 (s, 1H), 8.63 (d, 1H, J=2.16 Hz), 8.60 (dd, 1H, J=4.83 Hz, 1.14 Hz), 7.89-7.86 (m, 1H), 7.49 (q, 1H, J=4.22 Hz), 7.34 (s, 1H), 7.06 (d, 1H, J=7.41 Hz), 6.85 (t, 1H, J=7.5 Hz), 6.67 (d, 1H, J=7.89 Hz), 6.47 (t, 1H, J=7.455 Hz), 4.76 (s, 2H), 4.25 (s, 2H), 3.92 (s, 3H), 3.59 (s, 3H), 3.45 (t, 2H, J=7.125 Hz), 2.26 (t, 2H, J=7.275 Hz), 1.58-1.54 (m, 4H), 1.26-1.23 (m, 2H)

Example 34

Preparation of N-(2-aminophenyl)-6-(4-(3,5-difluorophenyl)-5,6-dimethoxy-1-oxoisoindolin-2-yl)hexanamide Step 1: Preparation of methyl 6-(4-(3,5-difluorophenyl)-5,6-dimethoxy-1-oxoisoindolin-2-yl)hexanoate The procedure of Example 2 was repeated expect for using methyl 6-(4-bromo-5,6-dimethoxy-1-oxoisoindolin-2-yl) hexanoate obtained in the Step 1 of Example 31 instead of N-(2-aminophenyl)-4-((4-bromo-5,6-dimethoxy-1-oxoisoindolin-2-yl)methyl)benzamide, 3,5-difluorophenyl boronic acid instead of phenyl boronic acid, 10 mol % of tetrakis(triphenyl-phosphino)palladium, and Na$_2$CO$_3$ (2 equiv.), to obtain the title compound (47%).

$^1$H NMR (300 MHz, CDCl$_3$): δ 7.39 (s, 1H), 6.92-6.82 (s, 3H), 4.11 (s, 2H), 3.94 (s, 3H), 3.65 (s, 3H), 3.62 (s, 3H), 3.55 (t, 2H, J=7.2 Hz), 2.28 (t, 2H, J=7.365 Hz), 1.69-1.57 (m, 4H), 1.38-1.26 (m, 2H).

Step 2: Preparation of 6-(4-(3,5-difluorophenyl)-5,6-dimethoxy-1-oxoisoindolin-2-yl)hexanoic acid The procedure of the Step 3 in Example 1 was repeated except that methyl 6-(4-(3,5-difluorophenyl)-5,6-dimethoxy-1-oxoisoindolin-2-yl)hexanoate obtained in the step 1 instead of methyl 4-((4-bromo-5,6-dimethoxy-1-oxoisoindolin-2-yl)methyl)benzoate, and LiOH.H$_2$O (2 equiv.) were used and the reaction was conducted for 3 hrs, to obtain the title compound quantitatively.

$^1$H NMR (300 MHz, CDCl$_3$): δ 7.42 (s, 1H), 6.94-6.86 (m, 3H), 4.13 (s, 2H), 3.96 (s, 3H), 3.67 (s, 3H), 3.58 (t, 2H, J=7.26 Hz), 2.35 (t, 2H, J=7.335 Hz), 1.70-1.62 (m, 4H), 1.41-1.35 (m, 2H).

Step 3: Preparation of N-(2-aminophenyl)-6-(4-(3,5-difluorophenyl)-5,6-dimethoxy-1-oxoisoindolin-2-yl)hexanamide The procedure of the step 4 in Example 1 was repeated except for using 6-(4-(3,5-difluorophenyl)-5,6-dimethoxy-1-oxoisoindolin-2-yl)hexanoic acid obtained in the step 2 instead of 4-((4-bromo-5,6-dimethoxy-1-oxoisoindolin-2-yl)methyl)benzoic acid, to obtain the title compound (29%)

$^1$H NMR (300 MHz, CDCl$_3$): δ 7.53 (s, 1H), 7.32 (s, 1H), 7.18 (d, 1H, J=7.62 Hz), 7.05-7.00 (m, 1H), 6.94-6.87 (m, 3H), 6.77 (dd, 2H, J=7.455 Hz, 1.815 Hz), 4.14 (s, 2H), 3.96-3.89 (m, 5H), 3.67 (s, 3H), 3.61 (t, 2H, J=5.76 Hz), 2.42 (t, 2H, J=5.775 Hz), 1.83-1.74 (m, 2H), 1.70-1.63 (m, 2H), 1.44-1.39 (m, 2H).

Example 35

Preparation of N-(2-aminophenyl)-6-(4-(4-(trifluoromethyl)phenyl)-5,6-dimethoxy-1-oxoisoindolin-2-yl)hexanamide Step 1: Preparation of methyl 6-(5,6-dimethoxy-1-oxo-4-(4-(trifluoromethyl)phenyl)isoindolin-2-yl) hexanoate The procedure of Example 2 was repeated except for using methyl 6-(4-bromo-5,6-dimethoxy-1-oxoisoindolin-2-yl) hexanoate obtained in the step 1 of Example 31 instead of N-(2-aminophenyl)-4-((4-bromo-5,6-dimethoxy-1-oxoisoindolin-2-yl)methyl)benzamide, 4-trifluoromethylphenyl boronic acid instead of phenyl boronic acid, 10 mol % of tetrakis(triphenyl-phosphino)palladium, and Na$_2$CO$_3$ (2 equiv.), to obtain the title compound (83%).

$^1$H NMR (300 MHz CDCl$_3$): δ 7.75-7.47 (m, 4H), 7.43 (s, 1H), 4.12 (s, 2H), 3.97 (s, 3H), 3.64 (s, 6H), 3.57 (t, 2H, J=7.185 Hz), 2.30 (t, 2H, J=7.32 Hz), 1.72-1.60 (m, 4H), 1.40-1.31 (m, 2H).

Step 2: Preparation of 6-(5,6-dimethoxy-1-oxo-4-(4-(trifluoromethyl)phenyl)isoindolin-2-yl)hexanoic acid The procedure of the Step 3 in Example 1 was repeated except that methyl 6-(5,6-dimethoxy-1-oxo-4-(4-(trifluoromethyl)phenyl)isoindolin-2-yl)hexanoate obtained in the step 1 of Example 35 instead of methyl 4-((4-bromo-5,6-dimethoxy-1-oxoisoindolin-2-yl)methyl)benzoate, and LiOH.H$_2$O (2 equiv.) were used and the reaction was conducted for 16 hrs, to obtain the title compound (99%).

$^1$H NMR (300 MHz, CDCl$_3$): δ 7.73 (d, 2H, J=8.04 Hz), 7.52 (d, 2H, J=7.74 Hz), 7.43 (s, 1H), 4.11 (s, 2H), 3.97 (s, 3H), 3.64 (s, 3H), 3.56 (t, 2H, J=7.305 Hz), 2.34 (t, 2H, J=7.365 Hz), 1.67-1.63 (m, 4H), 1.39-1.31 (m, 2H).

Step 3: Preparation of N-(2-aminophenyl)-6-(4-(4-(trifluoromethyl)phenyl)-5,6-dimethoxy-1-oxoisoindolin-2-yl)hexanamide The procedure of the step 4 of Example 1 was repeated except for using 6-(5,6-dimethoxy-1-oxo-4-(4-(trifluoromethyl)phenyl)isoindolin-2-yl)hexanoic acid obtained in the step 2 of Example 35 instead of 4-((4-bromo-5,6-dimethoxy-1-oxoisoindolin-2-yl)methyl)benzoic acid, to obtain the title compound (13%).

$^1$H NMR (300 MHz, DMSO-d$_6$): δ 9.04 (s, 1H), 7.83-7.79 (m, 2H), 7.69-7.65 (m, 2H), 7.34 (s, 1H), 7.06 (d, 1H, J=7.8 Hz), 6.85 (t, 1H, J=7.56 Hz), 6.67 (d, 1H, J=8.01 Hz), 6.47 (t, 1H, J=7.485 Hz), 4.76 (s, 2H), 4.22 (s, 2H), 3.92 (s, 3H), 3.59 (s, 3H), 3.44 (t, 2H, J=7.02 Hz), 2.26 (t, 2H, J=7.305 Hz), 1.60-1.51 (m, 4H), 1.31-1.20 (m, 2H).

Example 36

Preparation of N-(2-aminophenyl)-6-(4-bromo-1-oxoisoindolin-2-yl)hexanamide

Step 1: Preparation of methyl 6-(4-bromo-1-oxoisoindolin-2-yl)hexanoate

The procedure of the step 2 in Example 1 was repeated except that methyl 3-bromo-2-(bromomethyl)benzoate instead of methyl 3-bromo-2-(bromomethyl)-4,5-dimethoxybenzoate, methyl 6-aminohexanoate hydrochloride instead of methyl 4-(aminomethyl)benzoate hydrochloride, triethylamine (2.4 equiv.), and THF as a solvent were used and the reaction was conducted for 20 hrs, to obtain the title compound (99%).

$^1$H NMR (300 MHz, CDCl$_3$): δ 7.79 (d, 1H, J=7.5 Hz), 7.65 (d, 1H, J=7.92 Hz), 7.36 (t, 1H, J=7.71 Hz), 4.29 (s, 2H), 3.67-3.61 (m, 5H), 2.32 (t, 2H, J=7.425 Hz), 1.74-1.64 (m, 4H), 1.43-1.36 (m, 2H).

Step 2: Preparation of 6-(4-bromo-1-oxoisoindolin-2-yl)hexanoic acid

The procedure of the Step 3 in Example 1 was repeated except for using methyl 6-(4-bromo-1-oxoisoindolin-2-yl)hexanoate obtained in the step 1 of Example 36 instead of methyl 4-((4-bromo-5,6-dimethoxy-1-oxoisoindolin-2-yl)methyl)benzoate, and LiOH.H$_2$O (2 equiv.), to obtain the title compound quantitatively.

$^1$H NMR (300 MHz, CDCl$_3$): δ 7.80 (d, 1H, J=7.5 Hz), 7.65 (d, 1H, J=7.92 Hz), 7.36 (t, 1H, J=7.725 Hz), 4.30 (s, 2H), 3.64 (t, 2H, J=7.305 Hz), 2.37 (t, 2H, J=7.38 Hz), 1.77-1.65 (m, 4H), 1.47-1.39 (m, 2H).

Step 3: Preparation of N-(2-aminophenyl)-6-(4-bromo-1-oxoisoindolin-2-yl)hexanamide The procedure of the Step 4 in Example 1 was repeated except for using 6-(4-bromo-1-oxoisoindolin-2-yl)hexanoic acid obtained in the step 2 of Example 36 instead of 4-((4-bromo-5,6-dimethoxy-1-oxoisoindolin-2-yl)methyl)benzoic acid, to obtain the title compound (89%).

$^1$H NMR (300 MHz, DMSO-d$_6$): δ 9.06 (s, 1H), 7.79 (d, 1H, J=7.89 Hz), 7.68 (d, 1H, J=6.99 Hz), 7.45 (t, 1H, J=7.68 Hz), 7.08 (d, 1H, J=7.83 Hz), 6.86 (t, 1H, J=7.62 Hz), 6.68 (d, 1H, J=7.98 Hz), 6.48 (t, 1H, J=7.53 Hz), 4.78 (s, 2H), 4.41 (s, 3H), 3.53 (t, 2H, J=7.08 Hz), 2.29 (t, 2H, J=7.305 Hz), 1.67-1.59 (m, 4H), 1.32-1.27 (m, 2H).

Example 37

Preparation of N-(2-aminophenyl)-6-(1-oxo-4-phenylisoindolin-2-yl)hexanamide

The procedure of Example 2 was repeated except for using N-(2-aminophenyl)-6-(4-bromo-1-oxoisoindolin-2-yl)hexanamide obtained in Example 36 instead of N-(2-aminophenyl)-4-((4-bromo-5,6-dimethoxy-1-oxoisoindolin-2-yl)methyl)benzamide, to obtain the title compound (95%).

$^1$H NMR (300 MHz, DMSO-d$_6$): δ 9.07 (s, 1H), 7.71-760 (m, 5H), 7.52-7.40 (m, 3H), 7.08 (d, 1H, J=7.89 Hz), 6.86 (t, 1H, J=7.62 Hz), 6.68 (d, 1H, J=7.98 Hz), 6.48 (t, 1H, J=7.515 Hz), 4.78 (s, 2H), 4.62 (s, 2H), 3.53 (t, 2H, J=7.035 Hz), 2.29 (t, 2H, J=7.365 Hz), 1.66-1.59 (m, 4H), 1.33-1.31 (m, 2H).

Example 38

Preparation of N-(2-aminophenyl)-6-(1-oxo-4-(pyridin-3-yl)isoindolin-2-yl)hexanamide The procedure of Example 2 was repeated except for using N-(2-aminophenyl)-6-(4-bromo-1-oxoisoindolin-2-yl)hexanamide obtained in Example 36 instead of N-(2-aminophenyl)-4-((4-bromo-5,6-dimethoxy-1-oxoisoindolin-2-yl)methyl)benzamide, and 3-pyridinyl boronic acid instead of phenyl boronic acid, to obtain the title compound (94%).

$^1$H NMR (300 MHz, DMSO-d$_6$): δ 9.05 (s, 1H), 8.83 (d, 1H, J=2.22 Hz), 8.63 (dd, 1H, J=4.815 Hz, 1.695 Hz), 8.08-8.04 (m, 1H), 7.74-7.70 (m, 2H), 7.63 (d, 1H, J=7.62 Hz), 7.52 (dd, 1H, J=7.905 Hz, 4.575 Hz), 7.06 (d, 1H, J=8.1 Hz), 6.85 (t, 1H, J=7.53 Hz), 6.67 (d, 1H, J=8.04 Hz), 6.47 (t, 1H, J=7.53 Hz), 4.76 (s, 1203H), 4.64 (s, 2H), 3.52 (t, 2H, J=6.885 Hz), 2.28 (t, 2H, J=7.56 Hz), 1.66-1.57 (m, 4H), 1.33-1.27 (m, 2H).

Example 39

Preparation of N-hydroxy-6-(4-(2,4-dimethoxyphenyl)-1-oxoisoindolin-2-yl)hexanamide

Step 1: Preparation of 6-amino-N-(benzyloxy)hexanamide

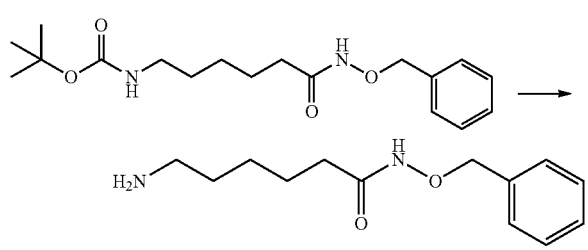

N-(benzyloxy)-6-(BOC-amino)hexanamide (5.65 g, 16.8 mmol) was dissolved in methylene chloride (40 mL), and the resulting solution thus obtained was cooled at 0° C. The trifluoroacetic acid (2.5 mL, 34 mmol, 2.0 eq.) was added thereto slowly and stirred at room temperature for 24 hrs. The reaction proceeded until no starting material was detectable by TLC. The resulting reaction mixture thus obtained was distilled under a reduced pressure to remove the solvent and thus obtained the title compound quantitatively.

The N-(benzyloxy)-6-(BOC-amino)hexanamide was prepared according to the method described in the document [Lee, B. H. et al. J. Med. Chem. 1985, 28(30, 317-323).

$^1$H NMR (300 MHz, CDCl$_3$): δ 11.01 (s, 1H), 8.05 (s, 2H), 7.22-7.17 (m, 3H), 4.71 (s, 2H), 2.68 (s, 2H), 1.93 (s, 2H), 1.54-1.25 (m, 6H), 1.07 (s, 2H).

Step 2: Preparation of N-(benzyloxy)-6-(4-bromo-1-oxoisoindolin-2-yl)hexanamide

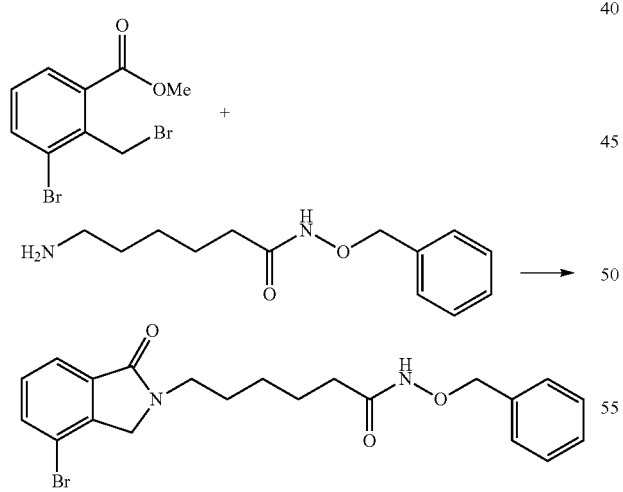

The procedure of the step 2 in Example 1 was repeated except that methyl 3-bromo-2-(bromomethyl)benzoate instead of methyl 3-bromo-2-(bromomethyl)-4,5-dimethoxybenzoate, and 6-amino-N-(benzyloxy)hexanamide (1.5 equiv.) obtained in the step 1 of Example 39 instead of methyl 4-(aminomethyl)benzoate hydrochloride were used and the reaction was conducted for 17 hrs, to obtain the title compound (90%).

$^1$H NMR (300 MHz, CDCl$_3$): δ 8.45 (s, 1H), 7.76 (d, 1H, J=7.5 Hz), 7.65 (dd, 1H, J=7.9, 0.8 Hz), 7.36-7.32 (m, 6H), 4.89 (s, 2H), 4.28 (s, 2H), 3.61 (t, 2H, J=7.1 Hz), 2.08 (s, 2H), 1.74-1.64 (m, 4H), 1.41-1.31 (m, 2H).

Step 3: Preparation of N-(benzyloxy)-6-(4-(2,4-dimethoxyphenyl)-1-oxoisoindolin-2-yl)hexanamide

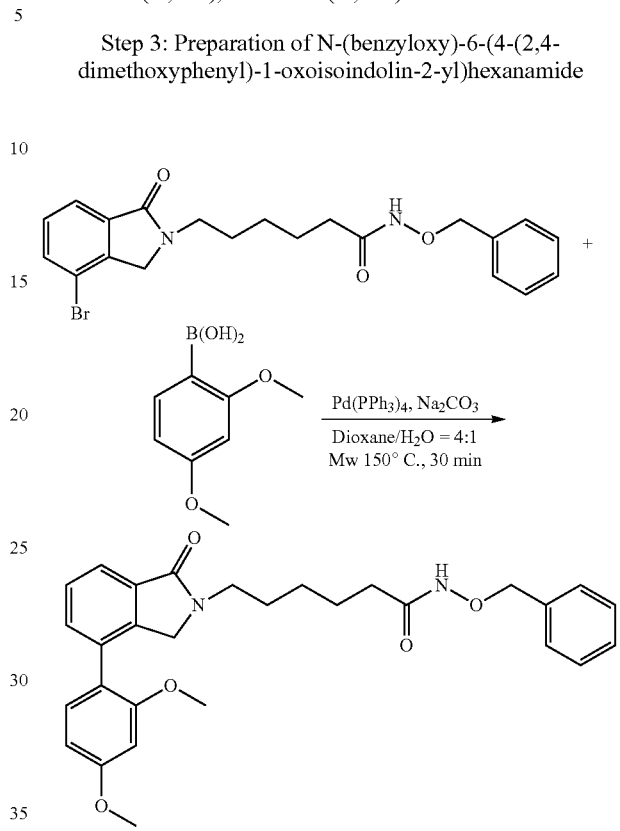

The procedure of Example 2 was repeated except that N-(benzyloxy)-6-(4-bromo-1-oxoisoindolin-2-yl)hexanamide obtained in the Step 2 of Example 39 instead of N-(2-aminophenyl)-4-((4-bromo-5,6-dimethoxy-1-oxoisoindolin-2-yl)methyl)benzamide, 2,4-dimethoxyphenyl boronic acid (3.0 equiv.) instead of phenyl boronic acid, 4 mol % of tetrakis(triphenylphosphin) palladium, and Na$_2$CO$_3$ (2 equiv.) were used and the reaction was conducted for 10 mins, to obtain the title compound (39%).

$^1$H NMR (300 MHz, CDCl$_3$): δ 7.74 (s, 1H), 7.44-7.38 (m, 2H), 7.33-7.24 (m, 5H), 7.19 (s, 1H), 7.08 (d, 1H, J=8.91 Hz), 6.54-6.51 (m, 2H), 4.77 (s, 2H), 4.17 (s, 2H), 3.80 (s, 3H), 3.70 (s, 3H), 3.52-3.48 (m, 2H), 2.03-1.97 (m, 2H), 1.59-1.53 (m, 4H), 1.27-1.19 (m, 2H).

Step 4: Preparation of 6-(4-(2,4-dimethoxyphenyl)-1-oxoisoindolin-2-yl)-N-hydroxyhexanamide

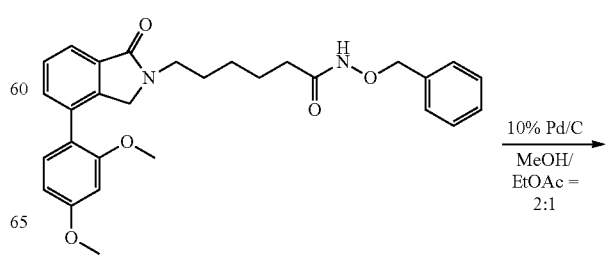

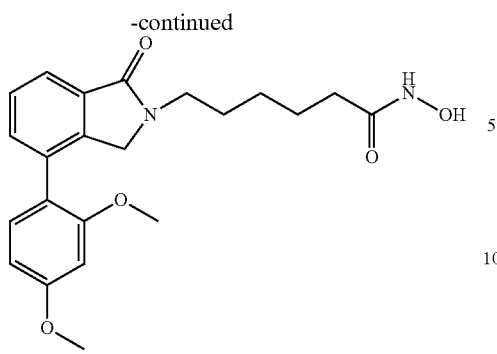

N-(benzyloxy)-6-(4-(2,4-dimethoxyphenyl)-1-oxoisoindolin-2-yl)hexanamide (22 mg, 0.045 mmol) in the Step 3 of Example 39 was dissolved in a mixture solvent of MeOH and EtOAc (mixture ratio=2:1 (v/v), 10 ml). 10% of Pd/C (2.2 mg) was added thereto and the reaction proceeded at room temperature for 5 hrs in state of the connected with hydrogen balloon. The resulting mixture thus obtained was filtered with Celite, and the filtrates were distilled under a reduced pressure to remove the solvent and obtained the title compound quantitatively.

$^1$H NMR (300 MHz, DMSO-d$_6$): δ 10.29 (s, 1H), 8.65 (s, 1H), 7.60 (d, 1H, J=7.26 Hz), 7.49 (t, 1H, J=7.5 Hz), 7.42 (d, 1H, J=7.32 Hz), 6.68 (s, 1H), 6.61 (dd, 2H, J=1.96 Hz, 8.44 Hz), 4.25 (s, 1H), 3.80 (s, 3H), 3.73 (s, 3H), 3.45 (t, 2H, J=6.78 Hz), 2.01-1.87 (m, 2H), 1.57-1.43 (m, 4H), 1.23-1.16 (m, 2H).

Example 40

Preparation of N-hydroxy-6-(4-(3,4-dimethoxyphenyl)-1-oxoisoindolin-2-yl)hexanamide Step 1: Preparation of N-(benzyloxy)-6-(4-(3,4-dimethoxyphenyl)-1-oxoisoindolin-2-yl)hexanamide The procedure of Example 2 was repeated except that N-(benzyloxy)-6-(4-bromo-1-oxoisoindolin-2-yl)hexanamide obtained in the Step 2 of Example 39 instead of N-(2-aminophenyl)-4-((4-bromo-5,6-dimethoxy-1-oxoisoindolin-2-yl)methyl)benzamide, 3,4-dimethoxyphenyl boronic acid instead of phenyl boronic acid, 4 mol % of tetrakis (triphenylphosphin) palladium, and Na$_2$CO$_3$ (2 equiv.) were used and the reaction was performed for 10 mins, to obtain the title compound (50%).

$^1$H NMR (300 MHz, CDCl$_3$): δ 7.77 (s, 1H), 7.52-7.51 (m, 2H), 7.36-7.32 (m, 5H), 7.03-6.95 (m, 3H), 4.87 (s, 2H), 4.41 (s, 2H), 3.93 (s, 3H), 3.92 (s, 3H), 3.58 (t, 2H, J=6.48 Hz), 2.05 (t, 2H, J=6.645 Hz), 1.65-1.62 (m, 4H), 1.37-1.32 (m, 2H).

Step 2: Preparation of N-hydroxy-6-(4-(3,4-dimethoxyphenyl)-1-oxoisoindolin-2-yl)hexanamide The procedure of the step 4 in Example 39 was repeated except that N-(benzyloxy)-6-(4-(3,4-dimethoxyphenyl)-1-oxoisoindolin-2-yl)hexanamide obtained in the Step 1 of Example 40 instead of N-(benzyloxy)-6-(4-(2,4-dimethoxyphenyl)-1-oxoisoindolin-2-yl)hexanamide was used and the reaction was performed for 15 hrs, to obtain the title compound (81%).

$^1$H NMR (300 MHz, DMSO-d$_6$): δ 7.63-7.54 (m, 3H), 7.14-7.03 (m, 3H), 6.65 (s, 1H), 4.75 (s, 1H), 4.57 (s, 2H), 3.80 (s, 3H), 3.79 (s, 3H), 3.51-3.44 (m, 2H), 2.33-2.25 (m, 2H), 1.62-1.40 (m, 4H), 1.28-1.17 (m, 2H).

Example 41

Preparation of N-hydroxy-6-(4-(3,5-dimethylphenyl)-1-oxoisoindolin-2-yl)hexanamide Step 1: Preparation of N-(benzyloxy)-6-(4-(3,5-dimethylphenyl)-1-oxoisoindolin-2-yl)hexanamide The procedure of Example 2 was repeated except that N-(benzyloxy)-6-(4-bromo-1-oxoisoindolin-2-yl)hexanamide obtained in the step 2 of Example 39 instead of N-(2-aminophenyl)-4-((4-bromo-5,6-dimethoxy-1-oxoisoindolin-2-yl)methyl)benzamide, 3,5-dimethylphenyl boronic acid instead of phenyl boronic acid, 4 mol % of tetrakis (triphenyl phosphin) palladium, and Na$_2$CO$_3$ (2 equiv.) were used and the reaction was performed for 10 mins, to obtain the title compound (45%).

$^1$H NMR (300 MHz, CDCl$_3$): δ 7.78 (s, 1H), 7.52-7.51 (m, 2H), 7.36-7.35 (m, 5H), 7.05 (s, 2H), 4.88 (s, 2H), 4.41 (s, 2H), 3.58 (t, 2H, J=5.025 Hz), 2.39 (s, 6H), 2.09-2.06 (m, 2H), 1.68-1.60 (m, 4H), 1.37-1.30 (m, 2H)

Step 2: Preparation of N-hydroxy-6-(4-(3,5-dimethylphenyl)-1-oxoisoindolin-2-yl)hexanamide The procedure of the step 4 in Example 39 was repeated except that N-(benzyloxy)-6-(4-(3,5-dimethylphenyl)-1-oxoisoindolin-2-yl) obtained in the step 1 of Example 41 instead of N-(benzyloxy)-6-(4-(2,4-dimethoxyphenyl)-1-oxoisoindolin-2-yl)hexanamide was used and the reaction was performed for 3.5 hrs, to obtain the title compound (47%).

$^1$H NMR (300 MHz, DMSO-d$_6$): δ 7.72 (s, 1H), 7.56 (s, 2H), 7.45-7.41 (m, 2H), 7.08 (s, 2H), 6.88 (s, 1H), 4.45 (s, 2H), 3.46 (t, 2H, J=5.19 Hz), 1.92-1.90 (m, 2H), 1.58-1.45 (m, 4H), 1.24-1.18 (m, 2H).

Example 42

Preparation of 6-(4-(3,5-difluorophenyl)-1-oxoisoindolin-2-yl)-N-hydroxyhexanamide Step 1: Preparation of N-(benzyloxy)-6-(4-(3,5-difluorophenyl)-1-oxoisoindolin-2-yl)hexanamide The procedure of Example 2 was repeated except that N-(benzyloxy)-6-(4-bromo-1-oxoisoindolin-2-yl)hexanamide obtained in the step 2 of Example 39 instead of N-(2-aminophenyl)-4-((4-bromo-5,6-dimethoxy-1-oxoisoindolin-2-yl)methyl)benzamide, 3,5-difluorophenyl boronic acid instead of phenyl boronic acid, 4 mol % of tetrakis(triphenyl phosphin) palladium, and Na$_2$CO$_3$ (2 equiv.) were used and the reaction was performed for 20 mins, to obtain the title compound (92%).

$^1$H NMR (300 MHz, CDCl$_3$): δ 7.80 (s, 1H), 7.64-7.62 (m, 1H), 7.49-7.40 (m, 3H), 7.20 (s, 1H), 6.93 (d, 2H, J=6.93 Hz), 6.81 (t, 1H, J=8.19 Hz), 4.74 (s, 2H), 4.34 (s, 2H), 3.55 (t, 2H, J=6.615 Hz), 2.02-1.94 (m, 2H), 1.65-1.58 (m, 4H), 1.28-1.20 (m, 2H).

Step 2: Preparation of 6-(4-(3,5-difluorophenyl)-1-oxoisoindolin-2-yl)-N-hydroxyhexanamide The procedure of the step 4 in Example 39 was repeated except that N-(benzyloxy)-6-(4-(3,5-difluorophenyl)-1-oxoisoindolin-2-yl)hexanamide obtained in the step 1 instead of N-(benzyloxy)-6-(4-(2,4-dimethoxyphenyl)-1-oxoisoindolin-2-yl)hexanamide was used and the reaction was performed for 20 hrs, to obtain the title compound (84%).

$^1$H NMR (300 MHz, DMSO-d$_6$): δ 7.70 (t, 1H, J=7.5 Hz), 7.63-7.59 (m, 1H), 7.56-7.52 (m, 1H), 7.41-7.38 (m, 1H), 7.34-7.27 (m, 1H), 6.65 (s, 1H), 4.75 (s, 2H), 4.63 (s, 2H), 3.50-3.43 (m, 2H), 1.88 (t, 2H, J=6.15 Hz), 1.60-1.43 (m, 4H), 1.27-1.17 (m, 2H).

Example 43

Preparation of N-hydroxy-6-(1-oxo-4-(pyridin-3-yl) isoindolin-2-yl)hexanamide

Step 1: Preparation of N-(benzyloxy)-6-(1-oxo-4-(pyridin-3-yl)isoindolin-2-yl)hexanamide The procedure of Example 2 was repeated except that N-(benzyloxy)-6-(4-bromo-1-oxoisoindolin-2-yl)hexanamide obtained in the step 2 of Example 39 instead of N-(2-aminophenyl)-4-((4-bromo-5,6-dimethoxy-1-oxoisoindolin-2-yl)methyl)benzamide, 3-pyridinyl boronic acid instead of phenyl boronic acid, 4 mol % of tetrakis(triphenyl phosphin) palladium, and Na$_2$CO$_3$ (2 equiv.) were used and the reaction was performed for 10 mins, to obtain the title compound (73%).

$^1$H NMR (300 MHz, CDCl$_3$): δ 9.11 (s, 1H), 8.90-8.55 (m, 2H), 7.93-7.80 (m, 2H), 7.57-7.43 (m, 4H), 7.34-7.20 (m, 4H), 4.79 (s, 2H), 4.38 (s, 2H), 3.52 (m, 2H), 2.04-1.98 (m, 2H), 1.68-1.52 (m, 4H), 1.28-1.20 (m, 2H).

Step 2: Preparation of N-hydroxy-6-(1-oxo-4-(pyridin-3-yl)isoindolin-2-yl)hexanamide The procedure of the step 4 in Example 39 was repeated except that N-(benzyloxy)-6-(1-oxo-4-(pyridin-3-yl)isoindolin-2-yl)hexanamide obtained in the step 1 of Example 43 instead of N-(benzyloxy)-6-(4-(2,4-dimethoxyphenyl)-1-oxoisoindolin-2-yl)hexanamide was used, and the reaction was performed for 4.5 hrs, to obtain the title compound (80%).

$^1$H NMR (300 MHz, DMSO-d$_6$): δ 8.72 (s, 1H), 8.52 (d, 1H, J=4.14 Hz), 7.97 (d, 1H, J=8.07 Hz), 7.63-7.51 (m, 3H), 7.42 (t, 1H, J=6.105 Hz), 7.21 (s, 1H), 4.58 (s, 1H), 4.52 (s, 2H), 3.39-3.33 (m, 2H), 1.77 (t, 2H, J=6.825 Hz), 1.49-1.34 (m, 4H), 1.16-1.07 (m, 2H).

Example 44

Preparation of 6-(4-(4-(trifluoromethyl)phenyl)-1-oxoisoindolin-2-yl)-N-hydroxyhexanamide Step 1: Preparation of N-(benzyloxy)-6-(1-oxo-4-(4-(trifluoromethyl)phenyl)isoindolin-2-yl)hexanamide The procedure of Example 2 was repeated except that N-(benzyloxy)-6-(4-bromo-1-oxoisoindolin-2-yl)hexanamide obtained in the step 2 of Example 39 instead of N-(2-aminophenyl)-4-((4-bromo-5,6-dimethoxy-1-oxoisoindolin-2-yl)methyl)benzamide, 4-(trifluoromethyl)phenyl boronic acid instead of phenyl boronic acid, 10 mol % of tetrakis(triphenylphosphin) palladium, and Na$_2$CO$_3$ (2 equiv.) were used and the reaction was performed for 20 mins, to obtain the title compound (72%).

$^1$H NMR (300 MHz, CDCl$_3$): δ 7.88-7.86 (m, 1H), 7.77-7.74 (m, 2H), 7.72-7.63 (m, 1H), 7.60-7.56 (m, 4H), 7.50-7.42 (m, 1H), 7.36 (m, 4H), 4.88 (s, 2H), 4.41 (s, 2H), 3.61 (t, 2H, J=7.08 Hz), 2.10-2.03 (m, 2H), 1.72-1.60 (m, 4H), 1.39-1.30 (m, 2H).

Step 2: Preparation of 6-(4-(4-(trifluoromethyl)phenyl)-1-oxoisoindolin-2-yl)-N-hydroxyhexanamide The procedure of the Step 4 in Example 39 was repeated except that N-(benzyloxy)-6-(1-oxo-4-(4-(trifluoromethyl) phenyl)isoindolin-2-yl)hexanamide in the step 1 of Example 44 instead of N-(benzyloxy)-6-(4-(2,4-dimethoxyphenyl)-1-oxoisoindolin-2-yl)hexanamide, was used and the reaction was performed for 25 hrs, to obtain the title compound (90%).

$^1$H NMR (300 MHz, DMSO-d$_6$): δ 7.87 (s, 2H), 7.76-7.52 (m, 5H), 7.20 (s, 1H), 6.67 (s, 1H), 4.63 (s, 2H), 3.50 (t, 2H, J=7.005 Hz), 2.02 (t, 2H, J=7.44 Hz), 1.63-1.46 (m, 4H), 1.29-1.23 (m, 2H).

Example 45

Preparation of N-(2-amino-5-(thiophen-2-yl)phenyl)-4-((4-bromo-1-oxoisoindolin-2-yl)methyl)benzamide Step 1: Preparation of tert-butyl 2-(4-((4-bromo-1-oxoisoindolin-2-yl)methyl)benzamido)-4-(thiophen-2-yl)phenylcarbamate

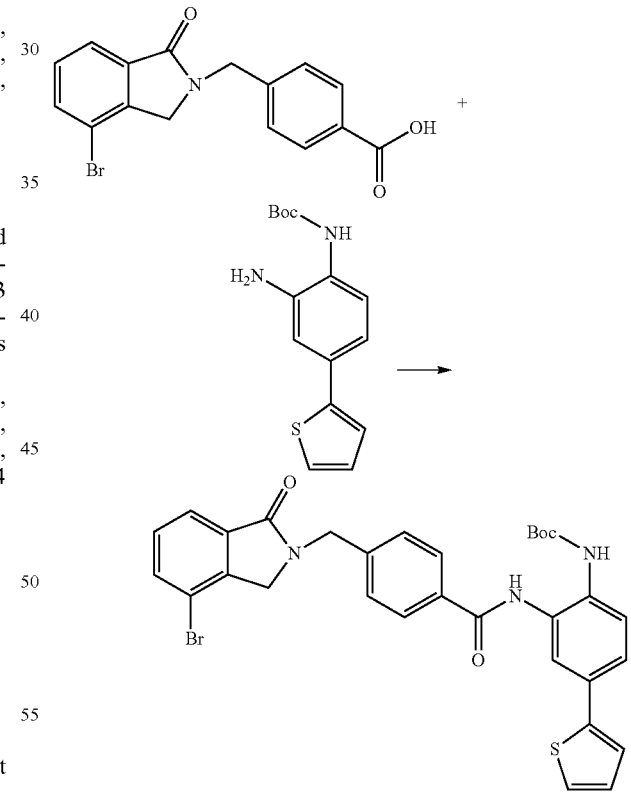

The procedure of the step 4 in Example 1 was repeated except that 4-((4-bromo-1-oxoisoindolin-2-yl)methyl)benzoic acid obtained in the step 2 of Example 9 instead of 4-((4-bromo-5,6-dimethoxy-1-oxoisoindolin-2-yl)methyl) benzoic acid, and tert-butyl 2-amino-4-(thiophen-2-yl)phenylcarbamate (1.5 equiv.) instead of 1,2-phenylenediamine were used and the reaction was performed for 24 hrs, to obtain the title compound (47%).

The tert-butyl 2-amino-4-(thiophen-2-yl)phenylcarbamate was prepared according to the method disclosed in document [D. J. Witter et al., Bioorg. Med. Chem. Lett. 18 (2008), 726-731].

$^1$H NMR (300 MHz, CDCl$_3$): δ 9.60 (s, 1H), 8.51 (d, 1H, J=7.8 Hz), 8.32 (d, 1H, J=7.5 Hz), 8.21 (d, 2H, J=7.8 Hz), 7.81-7.78 (m, 3H), 7.66 (dd, 1H, J=8.1, 1.2 Hz), 7.52 (d, 2H, J=7.2 Hz), 7.31 (d, 2H, J=7.5 Hz), 7.20-7.16 (m, 1H), 5.21 (s, 2H), 4.80 (s, 2H), 4.62 (s, 2H), 1.61 (s, 9H).

Step 2: Preparation of N-(2-amino-5-(thiophen-2-yl)phenyl)-4-((4-bromo-1-oxoisoindolin-2-yl)methyl)benzamide

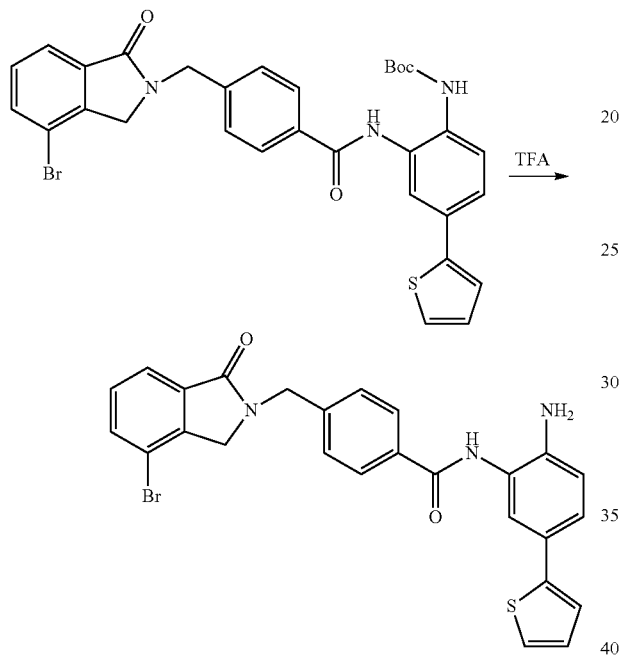

The procedure of the step 1 in Example 39 was repeated except that tert-butyl 2-(4-((4-bromo-1-oxoisoindolin-2-yl)methyl)benzamido)-4-(thiophen-2-yl)phenyl carbamate obtained in the step 1 of Example 45 instead of N-(benzyloxy)-6-(BOC-amino)hexanamide, and a mixture solvent of CH$_2$Cl$_2$ and trifluoroacetic acid (mixture ratio=1:1 (v/v)) were used and the reaction was performed for 3 hrs, to obtain the title compound (99%).

$^1$H NMR (300 MHz, CDCl$_3$): δ 9.60 (s, 1H), 8.51 (d, 1H, J=7.8 Hz), 8.32 (d, 1H, J=7.5 Hz), 8.21 (d, 2H, J=7.8 Hz), 7.81-7.78 (m, 3H), 7.66 (dd, 1H, J=8.1, 1.2 Hz), 7.52 (d, 2H, J=7.2 Hz), 7.31 (d, 2H, J=7.5 Hz), 7.20-7.16 (m, 1H), 5.21 (s, 2H), 4.80 (s, 2H), 4.62 (s, 2H).

Example 46

Preparation of N-(2-amino-5-(thiophen-2-yl)phenyl)-4-((1-oxo-4-(pyrimidin-5-yl)isoindolin-2-yl)methyl)benzamide Step 1: Preparation of tert-butyl 2-(4-((1-oxo-4-(pyrimidin-5-yl)isoindolin-2-yl)methyl)benzamido)-4-(thiophen-2-yl)phenylcarbamate The procedure of Example 2 was repeated except that tert-butyl 2-(4-((4-bromo-1-oxoisoindolin-2-yl)methyl)benzamido)-4-(thiophen-2-yl)phenyl carbamate obtained in the step 1 of Example 45 instead of N-(2-aminophenyl)-4-((4-bromo-5,6-dimethoxy-1-oxoisoindolin-2-yl)methyl)benzamide, and pyrimidin-5-yl-5-boronic acid instead of phenyl boronic acid were used and the reaction was performed for 20 mins, to obtain the title compound (52%).

$^1$H NMR (300 MHz, CDCl$_3$): δ 9.60 (s, 1H), 8.51 (d, 1H, J=7.8 Hz), 8.32 (d, 1H, J=7.5 Hz), 8.21-8.15 (m, 3H), 7.81-7.78 (m, 3H), 7.66 (dd, 1H, J=8.1, 1.2 Hz), 7.52 (d, 2H, J=7.2 Hz), 7.31 (d, 2H, J=7.5 Hz), 7.20-7.16 (m, 1H), 7.02 (s, 1H), 5.21 (s, 2H), 4.80 (s, 2H), 4.62 (s, 2H), 4.02 (s, 3H), 4.01 (s, 3H), 1.54 (s, 9H).

Step 2: Preparation of N-(2-amino-5-(thiophen-2-yl)phenyl)-4-((1-oxo-4-(pyrimidin-5-yl)isoindolin-2-yl)methyl)benzamide The procedure of the Step 1 in Example 39 was repeated except that tert-butyl 2-(4-((1-oxo-4-(pyrimidin-5-yl)isoindolin-2-yl)methyl)benzamido)-4-(thiophen-2-yl)phenylcarbamate obtained in the step 1 of Example 46 instead of N-(benzyloxy)-6-(BOC-amino)hexanamide, and a mixture of CH$_2$Cl$_2$ and trifluoroacetic acid (mixture ratio=1:1 (v/v)) were used and the reaction was performed for 3 hrs, to obtain the title compound (99%).

$^1$H NMR (300 MHz, CDCl$_3$): δ 9.60 (s, 1H), 8.51 (d, 1H, J=7.8 Hz), 8.32 (d, 1H, J=7.5 Hz), 8.21 (d, 2H, J=7.8 Hz), 8.01 (s, 1H), 8.00-7.91 (m, 2H), 7.81-7.78 (m, 3H), 7.66 (dd, 1H, J=8.1, 1.2 Hz), 7.52 (d, 2H, J=7.2 Hz), 7.31 (d, 2H, J=7.5 Hz), 7.20-7.16 (m, 1H), 5.21 (s, 2H), 4.80 (s, 2H), 4.62 (s, 2H).

Example 47

Preparation of N-(2-amino-5-(thiophen-2-yl)phenyl)-6-(1-oxo-4-(pyrimidin-5-yl)isoindolin-2-yl)hexanamide Step 1: Preparation of tert-Butyl 2-(6-(4-bromo-1-oxoisoindolin-2-yl)hexaneamido)-4-thiophen-2-yl)phenylcarbamate The procedure of the Step 4 in Example 1 was repeated except that 6-(4-bromo-1-oxoisoindolin-2-yl)hexanoic acid obtained in the step 2 of Example 36 instead of 4-((4-bromo-5,6-dimethoxy-1-oxoisoindolin-2-yl)methyl)benzoic acid, and tert-butyl 2-amino-4-(thiophen-2-yl)phenyl carbamate (1.5 equiv.) instead of 1,2-phenylene diamine were used and the reaction was performed for 24 hrs, to obtain the title compound (33%).

$^1$H NMR (300 MHz, CDCl$_3$): δ 9.60 (s, 1H), 8.51 (d, 1H, J=7.8 Hz), 8.32 (d, 1H, J=7.5 Hz), 7.81-7.78 (m, 3H), 7.66 (dd, 1H, J=8.1, 1.2 Hz), 7.20-7.16 (m, 1H), 7.02 (s, 1H), 5.21 (s, 2H), 4.80 (s, 2H), 4.62 (s, 2H), 4.02 (s, 3H), 4.01 (s, 3H), 3.52-3.48 (m, 2H), 2.42-2.41 (m, 2H), 1.82-1.69 (m, 2H), 1.67-1.66 (m, 2H), 1.53-1.51 (m, 2H), 1.55 (s, 9H).

Step 2: Preparation of tert-butyl 2-(6-(1-oxo-4-(pyrimidin-5-yl)isoindolin-2-yl)hexane amido)-4-(thiophen-2-yl)phenyl carbamate The procedure of Example 2 was repeated except that tert-butyl 2-(6-(4-bromo-1-oxoisoindolin-2-yl)hexanamido)-4-(thiophen-2-yl)phenylcarbamate obtained in the step 1 of Example 47 instead of N-(2-aminophenyl)-4-((4-bromo-5,6-dimethoxy-1-oxoisoindolin-2-yl)methyl)benzamide, and pyrimidin-5-yl-5-boronic acid instead of phenyl boronic acid were used and the reaction was performed for 20 mins, to obtain the title compound (56%).

$^1$H NMR (300 MHz, CDCl$_3$): δ 9.60 (s, 1H), 8.51 (d, 1H, J=7.8 Hz), 8.32 (d, 1H, J=7.5 Hz), 8.21-8.15 (m, 3H), 7.81-7.78 (m, 3H), 7.66 (dd, 1H, J=8.1, 1.2 Hz), 7.52 (d, 2H, J=7.2 Hz), 7.31 (d, 2H, J=7.5 Hz), 7.20-7.16 (m, 1H), 7.02 (s, 1H), 5.21 (s, 2H), 4.80 (s, 2H), 4.62 (s, 2H), 4.02 (s, 3H), 4.01 (s, 3H), 1.55 (s, 9H).

Step 3: Preparation of N-(2-amino-5-(thiophen-2-yl)phenyl)-6-(1-oxo-4-(pyrimidin-5-yl)isoindolin-2-yl)hexanamide The procedure of the Step 1 in Example 39 was repeated except that tert-butyl 2-(6-(1-oxo-4-(pyrimidin-5-yl)isoindolin-2-yl)hexanamido)-4-(thiophen-2-yl)phenylcarbamate obtained in the step 2 of Example 47 instead of N-(benzyloxy)-6-(BOC-amino)hexanamide, and a mixture of CH$_2$Cl$_2$ and trifluoroacetic acid (mixture ratio=1:1 (v/v)) were used and the reaction was performed for 3 hrs, to obtain the title compound (98%).

$^1$H NMR (300 MHz, CDCl$_3$): δ 9.60 (s, 1H), 8.51 (d, 1H, J=7.8 Hz), 8.32 (d, 1H, J=7.5 Hz), 8.06 (s, 1H), 7.98-7.90 (m, 2H), 7.81-7.78 (m, 3H), 7.66 (dd, 1H, J=8.1, 1.2 Hz), 7.20-7.16 (m, 1H), 7.02 (s, 1H), 5.21 (s, 2H), 4.80 (s, 2H), 4.62 (s, 2H), 4.02 (s, 3H), 4.01 (s, 3H), 3.52-3.48 (m, 2H), 2.42-2.41 (m, 2H), 1.82-1.69 (m, 2H), 1.67-1.66 (m, 2H), 1.53-1.51 (m, 2H).

Example 48

Preparation of N-(2-amino-5-(thiophen-2-yl)phenyl)-4-((5,6-dimethoxy-1-oxo-4-(pyridin-3-yl)isoindolin-2-yl)methyl)benzamide

Step 1: Preparation of tert-Butyl 2-(4-((4-bromo-5,6-dimethoxy-1-oxoisoindolin-2-yl)methyl)benzamido)-4-(thiophen-2-yl)phenylcarbamate The procedure of the Step 4 in Example 1 was repeated except that 1.5 equiv. of tert-butyl 2-amino-4-(thiophen-2-yl)phenylcarbamate instead of 1,2-phenylene diamine, and the reaction was performed for 24 hrs, to obtain the title compound (42%).

$^1$H NMR (300 MHz, CDCl$_3$): δ 9.60 (s, 1H), 8.51 (d, 1H, J=7.8 Hz), 8.32 (d, 1H, J=7.5 Hz), 7.81-7.78 (m, 3H), 7.66 (dd, 1H, J=8.1, 1.2 Hz), 7.52 (d, 2H, J=7.2 Hz), 7.31 (d, 2H, J=7.5 Hz), 7.20-7.16 (m, 1H), 7.02 (s, 1H), 5.21 (s, 2H), 4.80 (s, 2H), 4.62 (s, 2H), 4.02 (s, 3H), 4.01 (s, 3H), 1.54 (s, 9H)

Step 2: Preparation of tert-butyl 2-(4-((5,6-dimethoxy-1-oxo-4-(pyridin-3-251)isoindolin-2-yl)methyl)benzamido)-4-(thiophen-2-yl)phenylcarbamate The procedure of Example 2 was repeated except that tert-butyl 2-(4-((4-bromo-5,6-dimethoxy-1-oxoisoindolin-2-yl)methyl)benzamido)-4-(thiophen-2-yl)phenyl carbamate obtained in the Step 1 of Example 48 instead of N-(2-aminophenyl)-4-((4-bromo-5,6-dimethoxy-1-oxoisoindolin-2-yl)methyl)benzamide, and 3-pyridyl boronic acid instead of phenyl boronic acid and the reaction was performed for 20 mins, to obtain the title compound (46%).

$^1$H NMR (300 MHz, CDCl$_3$): δ 9.60 (s, 1H), 8.51 (d, 1H, J=7.8 Hz), 8.32 (d, 1H, J=7.5 Hz), 8.21-8.15 (m, 3H), 7.81-7.78 (m, 3H), 7.66 (dd, 1H, J=8.1, 1.2 Hz), 7.52 (d, 2H, J=7.2 Hz), 7.31 (d, 2H, J=7.5 Hz), 7.20-7.16 (m, 1H), 7.02 (s, 1H), 5.21 (s, 2H), 4.80 (s, 2H), 4.62 (s, 2H), 4.02 (s, 3H), 4.01 (s, 3H), 1.61 (s, 9H)

Step 3: Preparation of N-(2-amino-5-(thiophen-2-yl)phenyl)-4-((5,6-dimethoxy-1-oxo-4-(pyridin-3-yl)isoindolin-2-yl)methyl)benzamide The procedure of the Step 1 in Example 39 was repeated except that tert-butyl 2-(4-((5,6-dimethoxy-1-oxo-4-(pyridin-3-yl)isoindolin-2-yl)methyl)benzamido)-4-(thiophen-2-yl)phenylcarbamate in the Step 2 of Example 48 instead of N-(benzyloxy)-6-(BOC-amino)hexanamide and a mixture of CH$_2$Cl$_2$ and trifluoroacetic acid (mixture ratio=1:1 (v/v)) were used, and the reaction was performed for 3 hrs, to obtain the title compound (99%).

$^1$H NMR (300 MHz, CDCl$_3$): δ9.60 (s, 1H), 8.51 (d, 1H, J=7.8 Hz), 8.32 (d, 1H, J=7.5 Hz), 8.21-8.15 (m, 3H), 7.81-7.78 (m, 3H), 7.66 (dd, 1H, J=8.1, 1.2 Hz), 7.52 (d, 2H, J=7.2 Hz), 7.31 (d, 2H, J=7.5 Hz), 7.20-7.16 (m, 1H), 7.02 (s, 1H), 5.21 (s, 2H), 4.80 (s, 2H), 4.62 (s, 2H), 4.02 (s, 3H), 4.01 (s, 3H).

Example 49

Preparation of N-hydroxy-6-(1-oxo-5-phenylisoindolin-2-yl)hexanamide

Step 1: Preparation of N-(benzyloxy)-6-(5-bromo-1-oxoisoindolin-2-yl)hexanamide

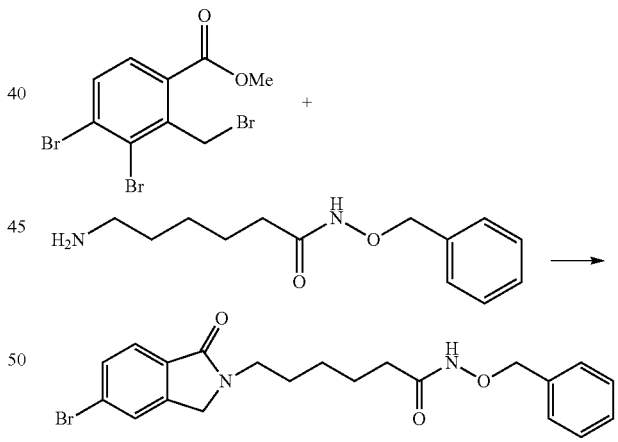

The procedure of the Step 2 in Example 39 was repeated except for using methyl 4-bromo-2-(bromomethyl)benzoate instead of methyl 3-bromo-2-(bromomethyl)benzoate, to obtain the title compound (46%).

The methyl 4-bromo-2-(bromomethyl)benzoate was prepared according to the method described in the document [Lee, Hyu Ji et al. Bioorganic & Medicinal Chemistry Letters (2008), 18(5), 1628-1631].

$^1$H NMR (300 MHz, CDCl$_3$): δ 9.3 (s, 1H), 7.63-7.54 (m, 3H), 7.34-7.28 (m, 5H), 4.87 (s, 2H), 4.31 (s, 2H), 3.53 (t, J=6.8 Hz, 2H), 2.07 (s, 2H), 1.65-1.60 (m, 4H), 1.36-1.26 (m, 2H).

Step 2: Preparation of N-(benzyloxy)-6-(1-oxo-5-phenylisoindolin-2-yl)hexanamide

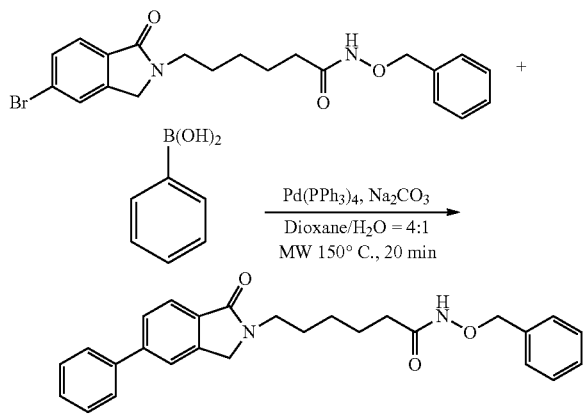

The procedure of Example 2 was repeated except that N-(benzyloxy)-6-(5-bromo-1-oxoisoindolin-2-yl)hexanamide obtained in the Step 1 of Example 49 instead of N-(2-aminophenyl)-4-((4-bromo-5,6-dimethoxy-1-oxoisoindolin-2-yl)methyl)benzamide and 10 mol % of tetrakis (triphenyl phosphin) palladium(0), and Na$_2$CO$_3$ (2 equiv.) were used, and the reaction was performed for 20 mins, to obtain the title compound (83%).

$^1$H NMR (300 MHz, CDCl$_3$): δ 7.77-7.74 (m, 1H), 7.58-7.50 (m, 5H), 7.41-7.23 (m, 8H), 4.81 (s, 2H), 4.32 (s, 2H), 3.50 (t, 2H, J=5.94 Hz), 2.05-1.95 (m, 2H), 1.65-1.55 (m, 4H), 1.30-1.20 (m, 2H).

Step 3: Preparation of N-hydroxy-6-(1-oxo-5-phenylisoindolin-2-yl)hexanamide

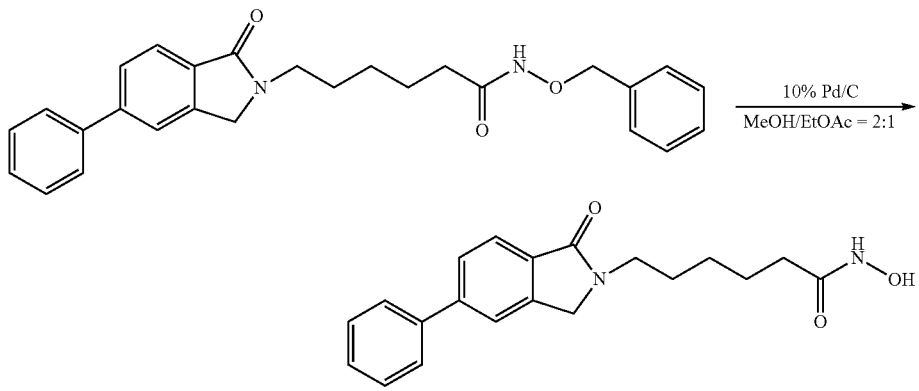

The procedure of the step 4 of Example 39 was repeated except that N-(benzyloxy)-6-(1-oxo-5-phenylisoindolin-2-yl)hexanamide obtained in the Step 2 of Example 49 instead of N-(benzyloxy)-6-(4-(2,4-dimethoxyphenyl)-1-oxoisoindolin-2-yl)hexanamide was used, and the reaction was performed for 10 hrs, to obtain the title compound (22.5 mg, 68%).

$^1$H NMR (300 MHz, DMSO-d$_6$): δ 10.32 (s, 1H), 8.66 (s, 1H), 7.85 (s, 1H), 7.74-7.69 (m, 2H), 7.63-7.38 (m, 5H), 4.50 (s, 2H), 3.50 (t, 2H, J=5.595 Hz), 1.93 (t, 2H, J=7.185 Hz), 1.63-1.46 (m, 4H), 1.28-1.20 (m, 2H).

Example 50

Preparation of N-hydroxy-6-(5-(2,4-dimethoxyphenyl)-1-oxoisoindolin-2-yl)hexanamide Step 1: Preparation of N-(benzyloxy)-6-(5-(2,4-dimethoxyphenyl)-1-oxoisoindolin-2-yl)hexanamide The procedure of Example 2 was repeated except that N-(benzyloxy)-6-(5-bromo-1-oxoisoindolin-2-yl)hexanamide obtained in the Step 1 of Example 49 instead of N-(2-aminophenyl)-4-((4-bromo-5,6-dimethoxy-1-oxoisoindolin-2-yl)methyl)benzamide, 2,4-dimethoxyphenyl boronic acid instead of phenyl boronic acid, 9 mol % of tetrakis (triphenyl-phosphino)palladium, and sodium carbonate (2 equiv.) were used, and the reaction for 10 mins under microwave was repeated twice, to obtain the title compound (17%).

$^1$H NMR (300 MHz, CDCl$_3$): δ 7.83-7.74 (m, 2H), 7.69-7.57 (m, 2H), 7.56-7.51 (m, 2H), 7.36 (m, 4H), 6.59-6.53 (m, 2H), 4.89 (s, 2H), 4.38 (s, 2H), 3.86 (s, 3H), 3.80 (s, 3H), 3.60 (t, 2H, J=6.57 Hz), 2.05-2.00 (m, 2H), 1.71-1.64 (m, 4H), 1.36-1.30 (m, 2H).

Step 2: Preparation of N-hydroxy-6-(5-(2,4-dimethoxyphenyl)-1-oxoisoindolin-2-yl)hexanamide The procedure of the Step 4 in Example 39 was repeated except that N-(benzyloxy)-6-(5-(2,4-dimethoxyphenyl)-1-oxoisoindolin-2-yl)hexanamide obtained in the Step 1 of Example 50 instead of N-(benzyloxy)-6-(4-(2,4-dimethoxyphenyl)-1-oxoisoindolin-2-yl)hexanamide was used, and the reaction was performed for 16 hrs, to obtain the title compound (66%).

$^1$H NMR (300 MHz, Acetone-d$_6$): δ 7.59-7.38 (m, 5H), 6.54-6.48 (m, 1H), 5.93 (s, 1H), 4.80 (s, 1H), 4.35 (s, 2H), 3.72 (s, 3H), 3.69 (s, 3H), 3.46 (t, 2H, J=7.08 Hz), 2.04 (t, 2H, J=7.335 Hz), 1.60-1.45 (m, 4H), 1.30-1.20 (m, 2H).

Example 51

Preparation of N-hydroxy-6-(5-(3,4-dimethoxyphenyl)-1-oxoisoindolin-2-yl)hexanamide Step 1: Preparation of N-(benzyloxy)-6-(5-(3,4-dimethoxyphenyl)-1-oxoisoindolin-2-yl)hexanamide The procedure of Example 2 was repeated except that N-(benzyloxy)-6-(5-bromo-1-oxoisoindolin-2-yl)hexanamide obtained in the Step 1 of Example 49 instead of N-(2-aminophenyl)-4-((4-bromo-5,6-dimethoxy-1-oxoisoindolin-2-yl)methyl)benzamide, 3,4-dimethoxyphenyl boronic acid instead of phenyl boronic acid, 10 mol % of tetrakis(triphenyl-phosphino)palladium, and sodium carbonate (2 equiv.) were used, and the reaction for 10 min under microwave was repeated, to obtain the title compound (71%).

$^1$H NMR (300 MHz, CDCl$_3$): δ 7.82 (d, 1H, J=7.74 Hz), 7.62-7.58 (m, 3H), 7.37-7.31 (m, 5H), 7.15 (d, 1H, J=8.25 Hz), 7.10 (s, 1H), 6.98 (d, 1H, J=8.31 Hz), 4.71 (s, 2H), 4.39 (s, 2H), 3.95 (s, 3H), 3.92 (s, 3H), 3.59 (t, 2H, J=6.51 Hz), 2.10-2.05 (m, 2H), 1.70-1.62 (m, 4H), 1.37-1.30 (m, 2H).

Step 2: Preparation of N-hydroxy-6-(5-(3,4-dimethoxyphenyl)-1-oxoisoindolin-2-yl)hexanamide The procedure of the step 4 in Example 39 was repeated except that N-(benzyloxy)-6-(5-(3,4-dimethoxyphenyl)-1-oxoisoindolin-2-yl)hexanamide obtained in the Step 1 of Example 51 instead of N-(benzyloxy)-6-(4-(2,4-dimethoxyphenyl)-1-oxoisoindolin-2-yl)hexanamide was used and the reaction was performed for 1 hr, to obtain the title compound (47%).

$^1$H NMR (300 MHz, DMSO-d$_6$): δ 8.43 (s, 1H), 7.77 (s, 1H), 7.64 (dd, 1H, J=7.875 Hz, 21.345 Hz), 7.20-7.14 (m, 2H), 6.99 (d, 1H, J=8.13 Hz), 6.61 (s, 1H), 4.42 (s, 2H), 3.78 (s, 3H), 3.72 (s, 3H), 3.43 (t, 2H, J=6.63 Hz), 1.95 (t, 2H, J=7.29 Hz), 1.55-1.40 (m, 4H), 1.20-1.15 (m, 2H).

Example 52

Preparation of N-hydroxy-6-(5-(3,5-dimethylphenyl)-1-oxoisoindolin-2-yl)hexanamide Step 1: Preparation of N-(benzyloxy)-6-(5-(3,5-dimethylphenyl)-1-oxoisoindolin-2-yl)hexanamide The procedure of Example 2 was repeated except that N-(benzyloxy)-6-(5-bromo-1-oxoisoindolin-2-yl)hexanamide obtained in the Step 1 of Example 49 instead of N-(2-aminophenyl)-4-((4-bromo-5,6-dimethoxy-1-oxoisoindolin-2-yl)methyl)benzamide, 3,5-dimethylphenyl boronic acid instead of phenyl boronic acid, 10 mol % of tetrakis(triphenyl-phosphino)palladium, and sodium carbonate (2 equiv.) were used, and the reaction for 10 min under microwave was repeated twice, to obtain the title compound (81%).

$^1$H NMR (300 MHz, CDCl$_3$): δ 7.77-7.74 (m, 1H), 7.57-7.53 (m, 2H), 7.30-7.25 (m, 5H), 7.19 (s, 1H), 7.13 (s, 2H), 6.96 (s, 1H), 4.82 (s, 2H), 4.32 (s, 2H), 3.52 (t, 2H, J=6.585 Hz), 2.07-2.00 (m, 2H), 1.65-1.55 (m, 4H), 1.30-1.21 (m, 2H).

Step 2: Preparation of N-hydroxy-6-(5-(3,5-dimethylphenyl)-1-oxoisoindolin-2-yl)hexanamide The procedure of the step 4 in Example 39 was repeated except that N-(benzyloxy)-6-(5-(3,5-dimethylphenyl)-1-oxoisoindolin-2-yl)hexanamide obtained in the Step 1 of Example 52 instead of N-(benzyloxy)-6-(4-(2,4-dimethoxyphenyl)-1-oxoisoindolin-2-yl)hexanamide was used, and the reaction was performed for 16 hrs, to obtain the title compound (65%).

$^1$H NMR (300 MHz, DMSO-d$_6$): δ 10.30 (s, 1H), 8.48 (s, 1H), 7.81 (s, 1H), 7.73-7.70 (m, 2H), 7.31 (s, 2H), 7.03 (s, 1H), 4.48 (s, 2H), 3.52-3.47 (m, 2H), 2.33 (s, 6H), 1.93 (t, 2H, J=7.2 Hz), 1.60-1.47 (m, 4H). 1.27-1.17 (m, 2H).

Example 53

Preparation of 6-(5-(3,5-difluorophenyl)-1-oxoisoindolin-2-yl)-N-hydroxyhexanamide Step 1: Preparation of N-(benzyloxy)-6-(5-(3,5-difluorophenyl)-1-oxoisoindolin-2-yl)hexanamide The procedure of Example 2 was repeated except that N-(benzyloxy)-6-(5-bromo-1-oxoisoindolin-2-yl)hexanamide obtained in the Step 1 of Example 49 instead of N-(2-aminophenyl)-4-((4-bromo-5,6-dimethoxy-1-oxoisoindolin-2-yl)methyl)benzamide, and 3,5-difluorophenyl boronic acid instead of phenyl boronic acid were used, and the reaction was performed for 20 mins, to obtain the title compound (81%).

$^1$H NMR (300 MHz, CDCl$_3$): δ 7.89-7.88 (m, 1H), 7.74-7.70 (m, 1H), 7.69-7.66 (m, 2H), 7.65-7.64 (m, 2H), 7.56-7.51 (m, 2H), 7.41-7.36 (m, 4H), 4.99 (s, 2H), 4.67 (s, 2H), 3.72 (t, 2H, J=6.2 Hz), 2.22-2.02 (m, 2H), 2.15-2.12 (m, 2H), 1.89-1.70 (m, 4H), 1.43-1.40 (m, 2H).

Step 2: Preparation of 6-(5-(3,5-difluorophenyl)-1-oxoisoindolin-2-yl)-N-hydroxyhexanamide The procedure of the Step 4 in Example 39 was repeated except that N-(benzyloxy)-6-(5-(3,5-difluorophenyl)-1-oxoisoindolin-2-yl)hexanamide obtained in the Step 1 of Example 53 instead of N-(benzyloxy)-6-(4-(2,4-dimethoxyphenyl)-1-oxoisoindolin-2-yl)hexanamide was used, and the reaction was performed for 6 hrs, to obtain the title compound (67%).

$^1$H NMR (300 MHz, Acetone-d$_6$): δ 7.78 (s, 1H), 7.68 (d, 1H, J=3.84 Hz), 7.60-7.37 (m, 4H), 7.27 (d, 1H, J=4.68 Hz), 6.98-6.91 (m, 1H), 4.43 (s, 2H), 3.48 (t, 2H, J=7.095 Hz), 2.04 (t, 2H, J=7.38 Hz), 1.61-1.50 (m, 4H), 1.28-1.22 (m, 2H).

Example 54

Preparation of N-hydroxy-6-(1-oxo-5-(pyridin-3-yl)isoindolin-2-yl)hexanamide

Step 1: Preparation of N-(benzyloxy)-6-(1-oxo-5-(pyridin-3-yl)isoindolin-2-yl)hexanamide The procedure of Example 2 was repeated except that N-(benzyloxy)-6-(5-bromo-1-oxoisoindolin-2-yl)hexanamide obtained in the Step 1 of Example 49 instead of N-(2-aminophenyl)-4-((4-bromo-5,6-dimethoxy-1-oxoisoindolin-2-yl)methyl)benzamide, and 3-pyridyl boronic acid instead of phenyl boronic acid were used, and the reaction was performed for 20 mins, to obtain the title compound (76%).

$^1$H NMR (300 MHz, CDCl$_3$): δ 8.11-8.06 (m, 1H), 8.01-7.09 (m, 1H), 7.78-7.72 (m, 1H), 7.70-7.69 (m, 2H), 7.52-7.50 (m, 2H), 7.26-7.21 (m, 2H), 7.11-7.06 (m, 4H), 5.01 (s, 2H), 4.86 (s, 2H), 3.88 (t, 2H, J=6.2 Hz), 2.21-2.14 (m, 2H), 2.13-2.10 (m, 2H), 1.89-1.77 (m, 4H), 1.40-1.36 (m, 2H)

Step 2: Preparation of N-hydroxy-6-(1-oxo-5-(pyridin-3-yl)isoindolin-2-yl)hexanamide The procedure of the step 4 in Example 39 was repeated except that N-(benzyloxy)-6-(1-oxo-5-(pyridin-3-yl)isoindolin-2-yl)hexanamide obtained in the Step 1 of Example 54 instead of N-(benzyloxy)-6-(4-(2,4-dimethoxyphenyl)-1-oxoisoindolin-2-yl)hexanamide was used, and the reaction was performed for 19 hrs, to obtain the title compound (40%).

$^1$H NMR (300 MHz, DMSO-d$_6$): δ 10.35-10.31 (m, 1H), 8.93 (s, 1H), 8.60 (d, 1H, J=4.62 Hz), 8.13 (d, 1H, J=7.95 Hz), 7.93 (s, 1H), 7.79 (dd, 2H, J=7.905 Hz, 20.475 Hz), 7.53-7.50 (m, 1H), 7.33 (s, 1H), 4.52 (s, 2H), 3.53-3.45 (m, 2H), 1.95-1.88 (m, 2H), 1.61-1.46 (m, 4H), 1.26-1.17 (m, 2H).

Example 55

Preparation of 6-(5-(4-(trifluoromethyl)phenyl)-1-oxoisoindolin-2-yl)-N-hydroxyhexanamide Step 1: Preparation of N-(benzyloxy)-6-(5-(trifluoro-4-methylphenyl)-1-oxoisoindolin-2-yl)hexanamide The procedure of Example 2 was repeated except that N-(benzyloxy)-6-(5-bromo-1-oxoisoindolin-2-yl)hexanamide obtained in the Step 1 of Example 49 instead of N-(2-aminophenyl)-4-((4-bromo-5,6-dimethoxy-1-oxoisoindolin-2-yl)methyl)benzamide, 4-(trifluoromethyl)phenyl boronic acid instead of phenyl boronic acid, 10 mol % of tetrakis(triphenyl-phosphino)palladium, and sodium carbonate (2 equiv.) were used, and the reaction was performed for 20 min under microwave, to obtain the title compound (76%).

$^1$H NMR (300 MHz, CDCl$_3$): δ 7.89-7.87 (m, 1H), 7.74-7.64 (m, 6H), 7.56-7.50 (m, 2H), 7.41-7.30 (m, 4H), 4.89 (s, 2H), 4.43 (s, 2H), 3.61 (t, 2H, J=5.895 Hz), 2.15-2.05 (m, 2H), 1.75-1.60 (m, 4H), 1.40-1.30 (m, 2H).

Step 2: Preparation of 6-(5-(4-(trifluoromethyl)phenyl)-1-oxoisoindolin-2-yl)-N-hydroxyhexanamide The procedure of the step 4 in Example 39 was repeated except that N-(benzyloxy)-6-(5-(trifluoro-4-methylphenyl)-1-oxoisoindolin-2-yl)hexanamide obtained in the Step 1 of Example 55 instead of N-(benzyloxy)-6-(4-(2,4-dimethoxyphenyl)-1-oxoisoindolin-2-yl)hexanamide was used, and the reaction was performed for 13 hrs, to obtain the title compound (49%).

$^1$H NMR (300 MHz, DMSO-d$_6$): δ 10.35 (s, 1H), 7.97-7.76 (m, 6H), 7.22 (s, 1H), 6.68 (s, 1H), 4.54 (s, 2H), 3.52 (t, 2H, J=6.735 Hz), 2.06-1.92 (m, 2H), 1.65-1.47 (m, 4H), 1.29-1.20 (m, 2H).

Example 56

Preparation of N-(2-aminophenyl)-4-((5-bromo-1-oxoisoindolin-2-yl)methyl)benzamide Step 1: Preparation of Methyl 4-((5-bromo-1-oxoisoindolin-2-yl)methyl)benzoate The procedure of the step 2 in Example 1 was repeated except that methyl 4-bromo-2-(bromomethyl)benzoate instead of methyl 3-bromo-2-(bromomethyl)-4,5-dimethoxybenzoate, and triethyl amine (1.2 equiv.) were used, and the reaction was performed for 6 hrs, to obtain the title compound (92%).

$^1$H NMR (300 MHz, CDCl$_3$): δ 7.72 (d, 1H, J=7.5 Hz), 7.66-7.58 (m, 4H), 7.35 (d, 1H, J=7.8 Hz), 7.34 (s, 1H), 5.12 (s, 2H), 4.88 (s, 2H), 4.01 (s, 3H).

Step 2: Preparation of 4-((5-Bromo-1-oxoisoindolin-2-yl)methyl)benzoic acid

The procedure of the step 3 in Example 1 was repeated except that methyl 4-((5-bromo-1-oxoisoindolin-2-yl)methyl)benzoate obtained in the Step 1 of Example 56 instead of methyl 4-((4-bromo-5,6-dimethoxy-1-oxoisoindolin-2-yl)methyl)benzoate, and LiOH.H$_2$O (2 equiv.) were used, and the reaction was performed for 5 hrs, to obtain the title compound (99%).

$^1$H NMR (300 MHz, CDCl$_3$): δ 7.72 (d, 1H, J=7.5 Hz), 7.66-7.58 (m, 4H), 7.34 (d, 1H, J=7.8 Hz), 7.30 (s, 1H), 5.11 (s, 2H), 5.00 (s, 2H).

Step 3: Preparation of N-(2-aminophenyl)-4-((5-bromo-1-oxoisoindolin-2-yl)methyl)benzamide The procedure of the step 4 in Example 1 was repeated except that 4-((5-bromo-1-oxoisoindolin-2-yl)methyl)benzoic acid obtained in the Step 2 of Example 56 instead of 4-((4-bromo-5,6-dimethoxy-1-oxoisoindolin-2-yl)methyl) benzoic acid, and 1,2-phenylene diamine (1.5 equiv.) were used, and the reaction was performed for 24 hrs, to obtain the title compound (62%).

$^1$H NMR (300 MHz, CDCl$_3$): δ 7.89 (d, 2H, J=8.0 Hz), 7.79 (d, 2H, J=7.8 Hz), 7.76 (s, 1H), 7.63 (d, 1H, J=7.8 Hz), 7.58 (s, 1H), 7.40-7.38 (m, 2H), 7.30-7.28 (m, 1H), 7.08 (t, 1H, J=8.1 Hz), 6.88-6.87, J=7.5 Hz), 4.86 (s, 2H), 4.28 (s, 2H).

Example 57

Preparation of N-(2-aminophenyl)-4-((1-oxo-5-phenylisoindolin-2-yl)methyl)benzamide The procedure of Example 2 was repeated except that N-(2-aminophenyl)-4-((5-bromo-1-oxoisoindolin-2-yl)methyl)benzamide obtained in Example 56 instead of N-(2-aminophenyl)-4-((4-bromo-5,6-dimethoxy-1-oxoisoindolin-2-yl)methyl)benzamide was used, and the reaction was performed for 20 mins, to obtain the title compound (72%).

$^1$H NMR (300 MHz, CDCl$_3$): δ 8.19 (s, 1H), 7.94-7.87 (m, 2H), 7.83-7.80 (m, 1H), 7.67-7.63 (m, 3H), 7.57-7.47 (m, 3H), 7.46-7.41 (m, 3H), 7.38-7.36 (m, 2H), 7.07 (t, 1H, J=7.0 Hz), 6.82 (d, 2H, J=6.8 Hz), 4.85 (s, 2H), 4.33 (s, 2H).

Example 58

Preparation of N-(2-aminophenyl)-4-((1-oxo-5-(pyrimidin-5-yl)isoindolin-2-yl)methyl)benzamide The procedure of Example 2 was repeated except that N-(2-aminophenyl)-4-((5-bromo-1-oxoisoindolin-2-yl)methyl)benzamide obtained in Example 56 instead of N-(2-aminophenyl)-4-((4-bromo-5,6-dimethoxy-1-oxoisoindolin-2-yl)methyl)benzamide, and pyrimidin-5-yl-5-boronic acid instead of phenyl boronic acid were used, and the reaction was performed for 20 mins, to obtain the title compound (55%).

$^1$H NMR (300 MHz, CDCl$_3$): δ 9.25 (s, 1H), 9.00 (s, 1H), 8.97 (s, 2H), 8.11 (s, 1H), 8.03 (d, 1H, J=8.0 Hz), 7.90 (d, 2H, J=8.2 Hz), 7.70 (d, 1H, J=7.9 Hz), 7.62 (s, 1H), 7.41 (d, 2H, J=8.3 Hz), 7.31 (d, 1H, J=7.9 Hz), 7.07 (t, 1H, J=7.5 Hz), 6.84 (d, 2H, J=8.0 Hz), 4.89 (s, 2H), 4.41 (s, 2H).

Example 59

Preparation of N-(2-aminophenyl)-4-((5-(4-(trifluoromethyl)phenyl)-1-oxoisoindolin-2-yl)methyl)benzamide The procedure of Example 2 was repeated except that N-(2-aminophenyl)-4-((5-bromo-1-oxoisoindolin-2-yl)methyl)benzamide obtained in Example 56 instead of N-(2-aminophenyl)-4-((4-bromo-5,6-dimethoxy-1-oxoisoindolin-2-yl)methyl)benzamide, and 4-(trifluoromethyl)phenyl boronic acid instead of phenyl boronic acid were used, and the reaction was performed for 20 mins, to obtain the title compound (47%).

$^1$H NMR (300 MHz, CDCl$_3$): δ 7.99 (d, 1H, J=8.2 Hz), 7.91 (d, 1H, J=8.4 Hz), 7.71-7.69 (m, 4H), 7.66-7.65 (m, 1H), 7.62-7.60 (m, 1H), 7.55-7.52 (m, 2H), 7.49-7.43 (m, 4H), 7.33 (d, 1H, J=7.8 Hz), 7.08 (t, 1H, J=7.5 Hz), 6.85 (d, 2H, J=7.8 Hz), 4.89 (s, 2H), 4.37 (s, 2H).

Example 60

Preparation of N-(2-aminophenyl)-4-((5-(3,5-difluorophenyl)-1-oxoisoindolin-2-yl)methyl)benzamide The procedure of Example 2 was repeated except that N-(2-aminophenyl)-4-((5-bromo-1-oxoisoindolin-2-yl)methyl)benzamide obtained in Example 56 instead of N-(2-aminophenyl)-4-((4-bromo-5,6-dimethoxy-1-oxoisoindolin-2-yl)methyl)benzamide, and 3,5-difluorophenyl boronic acid instead of phenyl boronic acid were used, and the reaction was performed for 20 mins, to obtain the title compound (64%).

$^1$H NMR (300 MHz, CDCl$_3$): δ 8.22 (s, 1H), 7.95-7.88 (m, 2H), 7.67-7.61 (m, 3H), 7.55-7.52 (m, 2H), 7.46 (dd, 2H, J=7.2, 1.1 Hz), 7.38 (d, 2H, J=7.5 Hz), 7.33 (d, 1H, J=7.5 Hz), 7.11-7.07 (m, 2H), 6.84-6.81 (m, 2H), 4.85 (s, 2H), 4.34 (s, 2H).

Example 61

Preparation of N-(2-aminophenyl)-4-((1-oxo-5-(pyridin-3-yl)isoindolin-2-yl)methyl)benzamide The procedure of Example 2 was repeated except that N-(2-aminophenyl)-4-((5-bromo-1-oxoisoindolin-2-yl)methyl)benzamide obtained in Example 56 instead of N-(2-aminophenyl)-4-((4-bromo-5,6-dimethoxy-1-oxoisoindolin-2-yl)methyl)benzamide, and 3-pyridyl boronic acid instead of phenyl boronic acid were used, and the reaction was performed for 20 mins, to obtain the title compound (59%).

$^1$H NMR (300 MHz, CDCl$_3$): δ 8.85 (s, 1H), 8.63 (d, 1H, J=8.1 Hz), 8.17 (s, 1H), 7.98 (d, 1H, J=7.5 Hz), 7.90 (d, 2H, J=7.8 Hz), 7.68 (d, 2H, 7.8 Hz), 7.60 (s, 1H), 7.55 (d, 1H, J=7.5 Hz), 7.45 (dd, 1H, J=4.5, 1.2 Hz), 7.40 (d, 3H, J=8.2 Hz), 7.32 (d, 1H, J=8.4 Hz), 7.07 (t, 1H, J=7.5 Hz), 6.84 (d, 2H, J=8.1 Hz), 4.88 (s, 2H), 4.37 (s, 2H).

Example 62

Preparation of N-(2-aminophenyl)-4-((5-(3,5-dimethylphenyl)-1-oxoisoindolin-2-yl)methyl)benzamide The procedure of Example 2 was repeated except that N-(2-aminophenyl)-4-((5-bromo-1-oxoisoindolin-2-yl)methyl)benzamide obtained in Example 56 instead of N-(2-aminophenyl)-4-((4-bromo-5,6-dimethoxy-1-oxoisoindolin-2-yl)methyl)benzamide, and 3,5-dimethylphenyl boronic acid instead of phenyl boronic acid were used, and the reaction was performed for 20 mins, to obtain the title compound (46%).

$^1$H NMR (300 MHz, CDCl$_3$): δ 8.08 (s, 1H), 7.90-7.88 (m, 4H), 7.66 (d, 1H, J=8.1 Hz), 7.57 (s, 1H), 7.40 (d, 3H, J=8.4 Hz), 7.32 (d, 1H, J=8.1 Hz), 7.20 (s, 2H), 7.08-7.06 (m, 2H), 6.84 (d, 2H, J=7.5 Hz), 4.87 (s, 2H), 4.33 (s, 2H), 2.38 (s, 6H).

Example 63

Preparation of N-(2-aminophenyl)-4-(5-(4-methoxyphenyl)-1-oxoisoindolin-2-yl)methyl)benzamide The procedure of Example 2 was repeated except that N-(2-aminophenyl)-4-((5-bromo-1-oxoisoindolin-2-yl)methyl)benzamide obtained in Example 56 instead of N-(2-aminophenyl)-4-((4-bromo-5,6-dimethoxy-1-oxoisoindolin-2-yl)methyl)benzamide, and 4-methoxyphenyl boronic acid instead of phenyl boronic acid were used, and the reaction was performed for 20 mins, to obtain the title compound (32%).

$^1$H NMR (300 MHz, CDCl$_3$): δ 7.90 (t, 2H, J=8.1 Hz), 7.69-7.65 (m, 4H), 7.54 (d, 3H, J=8.2 Hz), 7.47 (dd, 3H, J=6.8, 1.8 Hz), 7.41 (d, 1H, J=7.5 Hz), 7.34 (d, 1H, J=8.2 Hz), 7.08 (t, 1H, J=7.5 Hz), 6.98 (d, 1H, J=7.8 Hz), 6.86-6.83 (m, 2H), 4.89 (s, 2H), 4.33 (s, 2H), 3.86 (s, 3H).

Example 64

Preparation of N-(2-aminophenyl)-4-((5-(3,4-dimethoxyphenyl)-1-oxoisoindolin-2-yl)methyl)benzamide The procedure of Example 2 was repeated except that N-(2-aminophenyl)-4-((5-bromo-1-oxoisoindolin-2-yl)methyl)benzamide obtained in Example 56 instead of N-(2-aminophenyl)-4-((4-bromo-5,6-dimethoxy-1-oxoisoindolin-2-yl)methyl)benzamide, and 3,4-dimethoxyphenyl boronic acid instead of phenyl boronic acid were used, and the reaction was performed for 20 mins, to obtain the title compound (52%).

$^1$H NMR (300 MHz, CDCl$_3$): δ 7.94 (d, 1H, J=8.0 Hz), 7.91 (d, 1H, J=7.8 Hz), 7.68-7.66 (m, 2H), 7.63 (d, 1H, J=8.1 Hz), 7.57-7.52 (m, 2H), 7.48-7.44 (m, 3H), 7.33 (d, 1H, J=8.1 Hz), 7.16 (dd, 1H, J=7.8, 1.2 Hz), 7.10-7.08 (m, 2H), 6.96 (d, 1H, J=8.1 Hz), 6.88-6.84 (m, 2H), 4.90 (s, 2H), 4.35 (s, 2H), 3.95 (s, 3H), 3.93 (s, 3H).

Example 65

Preparation of N-(2-aminophenyl)-4-[5-(4-cyanophenyl)-1-oxo-2,3-dihydro-1H-isoindol-2-yl]methylbenzamide The procedure of Example 2 was repeated except that N-(2-aminophenyl)-4-((5-bromo-1-oxoisoindolin-2-yl)methyl)benzamide in Example 56 instead of N-(2-aminophenyl)-4-((4-bromo-5,6-dimethoxy-1-oxoisoindolin-2-yl)methyl)benzamide, and 4-cyanophenyl boronic acid instead of phenyl boronic acid were used, and the reaction was performed for 20 mins, to obtain the title compound (59%).

$^1$H NMR (300 MHz, CDCl$_3$): δ 8.00 (d, 1H, J=8.0 Hz), 7.90-7.88 (m, 2H), 7.79-7.77 (m, 2H), 7.72-7.70 (m, 2H), 7.61 (s, 1H), 7.54 (d, 2H, J=7.8 Hz), 7.52-7.45 (m, 2H), 7.34 (d, 1H, J=7.5 Hz), 7.11 (t, 1H, J=7.8 Hz), 6.90-6.88 (m, 4H), 4.91 (s, 2H), 4.39 (s, 2H).

Example 66

Preparation of N-(2-aminophenyl)-4-((5-(benzo[d][1,3]dioxol-6-yl)-1-oxoisoindolin-2-yl)methyl)benzamide The procedure of Example 2 was repeated except that N-(2-aminophenyl)-4-((5-bromo-1-oxoisoindolin-2-yl)methyl)benzamide obtained in Example 56 instead of N-(2-aminophenyl)-4-((4-bromo-5,6-dimethoxy-1-oxoisoindolin-2-yl)methyl)benzamide, and benzo[d][1,3]dioxol-5-yl-5-boronic acid instead of phenyl boronic acid were used, and the reaction was performed for 20 mins, to obtain the title compound (43%).

$^1$H NMR (300 MHz, CDCl$_3$): δ 7.92-7.90 (m, 4H), 7.63 (dd, 1H, J=8.1 Hz, 1.2 Hz), 7.52 (s, 1H), 7.44 (d, 2H, J=8.5 Hz), 7.34 (d, 1H, J=8.0 Hz), 7.11-7.08 (m, 3H), 6.89-6.86 (m, 3H), 6.02 (s, 2H), 4.89 (s, 2H), 4.34 (s, 2H), 3.86 (s, 2H).

Example 67

Preparation of N-(2-aminophenyl)-4-((5-(naphthalen-2-yl)-1-oxoisoindolin-2-yl)methyl)benzamide The procedure of Example 2 was repeated except that N-(2-aminophenyl)-4-((5-bromo-1-oxoisoindolin-2-yl)methyl)benzamide obtained in Example 56 instead of N-(2-aminophenyl)-4-((4-bromo-5,6-dimethoxy-1-oxoisoindolin-2-yl)methyl)benzamide, and naphthalen-2-yl-2-boronic acid instead of phenyl boronic acid were used, and the reaction was performed for 20 mins, to obtain the title compound (61%).

$^1$H NMR (300 MHz, CDCl$_3$): δ 8.00 (s, 1H), 7.99-7.97 (m, 5H), 7.80-7.78 (m, 2H), 7.66-7.61 (m, 2H), 7.55-7.53 (m, 2H), 7.38 (d, 2H, J=8.1 Hz), 7.10 (d, 1H, J=7.5 Hz), 6.89 (td, 1H, J=8.0, 1.2 Hz), 6.79 (dd, 1H, J=7.8, 1.2 Hz), 6.65 (td, 1H, J=8.0, 1.1 Hz), 4.88 (s, 2H), 4.67 (s, 2H).

Example 68

Preparation of N-(2-aminophenyl)-4-((3-bromo-2-methylbenzamido)methyl)benzamide

Step 1: Preparation of methyl 4-((3-bromo-2-methylbenzamido)methyl)benzoate

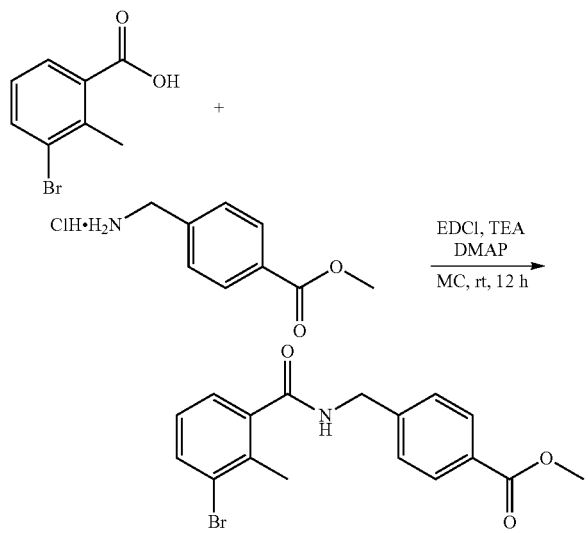

1.0 g of 3-bromo-2-methylbenzoic acid (4.65 mmol), 1.87 g of methyl 4-(aminomethyl)benzoate hydrochloride (9.3 mmol), 1-ethyl-3-(3-dimethylaminopropyl)-carbodiimide hydrochloride (EDCI; 1.07 g (5.58 mmol)), and dimethylaminopyridine (DMAP; 56 mg, 0.46 mmol) were dissolved in 50 mL of methylene chloride. 1.90 mL of tryethylamine (3 equiv.) was added dropwise thereto, and stirred at room temperature overnight.

50 mL of saturated sodium bicarbonate was added to the resulting mixture, extracted with methylene chloride (3×75 mL), and the separated organic layer was dried over anhydrous magnesium sulfate. The residue was subjected to column chromatography (hexane:ethyl acetate=1:1, v/v) to obtain the title compound (886 mg, 52%).

$^1$H NMR (300 MHz, CDCl$_3$): δ 8.04 (d, 2H, J=8.1 Hz), 7.61 (d, 1H, J=7.8 Hz), 7.43 (d, 2H, J=8.1 Hz), 7.30 (d, 1H, J=7.5 Hz), 7.08 (t, 1H, J=7.8 Hz), 6.08 (brs, 1H), 4.69 (d, 2H, J=6.0 Hz), 3.93 (s, 3H), 2.49 (s, 3H).

Step 2: Preparation of 4-((3-bromo-2-methylbenzamido)methyl)benzoate

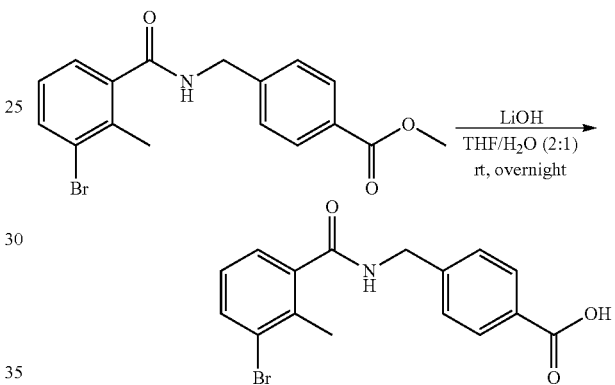

Methyl 4-((3-bromo-2-methylbenzamido)methyl)benzoate obtained in step 1 (950 mg, 2.62 mmol) and lithium hydroxide monohydrate (550 mg, 13.1 mmol) were dissolved in 10 mL of tetrahydrofuran (THF)/H$_2$O (2:1) and stirred at room temperature for 12 hours. The resulting mixture was subjected to thin layer chromatography to monitor the amount of methyl 4-((3-bromo-2-methylbenzamido)methyl) benzoate consumed. THF was removed under a reduced pressure and 1N HCl was added dropwise to the residue to adjust its pH to 2. The resulting white solid thus obtained was filtered and dried to obtain the title compound (887 mg, 97%).

$^1$H NMR (300 MHz, DMSO-d$_6$): δ 8.99 (t, 1H, J=6.0 Hz), 7.91 (d, 2H, J=8.1 Hz), 7.66 (d, 1H, J=6.9 Hz), 7.44 (d, 2H, J=8.4 Hz), 7.35 (d, 1H, J=6.6 Hz), 7.19 (t, 1H, J=7.8 Hz), 4.49 (d, 2H, J=6.0 Hz), 2.32 (s, 3H).

Step 3: Preparation of N-(2-aminophenyl)-4-((3-bromo-2-methylbenzamido) methyl)benzamide

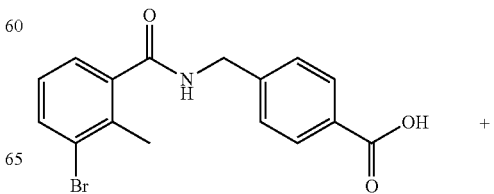

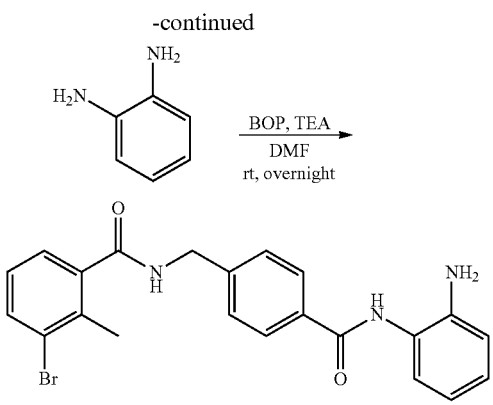

Phenylenediamine (217 mg, 2.01 mmol), 1H-benzothiazol-1-yloxytris-(dimethylamino)phosphonium hexafluorophosphate (BOP; 667 mg, 1.51 mmol) and triethyl amine (203 mg, 2.01 mmol) were dissolved in 3 mL of DMF. 350 mg of the 4-((3-bromo-2-methylbenzamido)methyl)benzoate obtained in step 2 (1.01 mmol) was added thereto and stirred at room temperature overnight. The resulting mixture was subjected to thin layer chromatography to monitor the amount of 4-((3-bromo-2-methylbenzamido)methyl)benzoate consumed, and DMF was removed under a reduced pressure. 50 mL of saturated sodium bicarbonate was added to the resulting mixture, extracted with methylene chloride (3×75 mL) and the separated organic layer was dried over anhydrous magnesium sulfate. The residue was dissolved in methylene chloride and n-pentane was added thereto. The resulting solid thus obtained was filtered and washed with ethanol to obtain the title compound (231 mg, 52%).

$^1$H NMR (300 MHz, DMSO-$d_6$): δ 9.63 (s, 1H), 9.01 (t, 1H, J=6.0 Hz), 7.95 (d, 2H, J=8.1 Hz), 7.67 (dd, 1H, J=8.1 Hz, 1.2 Hz), 7.45 (d, 2H, J=8.1 Hz), 7.35 (dd, 1H, J=7.5 Hz, 1.2 Hz), 7.21 (d, 1H, J=7.8 Hz), 7.15 (dd, 1H, J=7.8 Hz, 2.7 Hz), 6.96 (td, 1H, J=8.1 Hz, 1.2 Hz), 6.77 (dd, 1H, J=8.1 Hz, 1.5 Hz), 6.58 (td, 1H, J=7.2 Hz, 1.2 Hz), 4.88 (brs, 2H), 4.50 (d, 2H, J=6.0 Hz), 2.34 (s, 3H).

Example 69

Preparation of N-(2-aminophenyl)-4-((2-methyl-3-phenyl-benzamido)methyl)benzamide

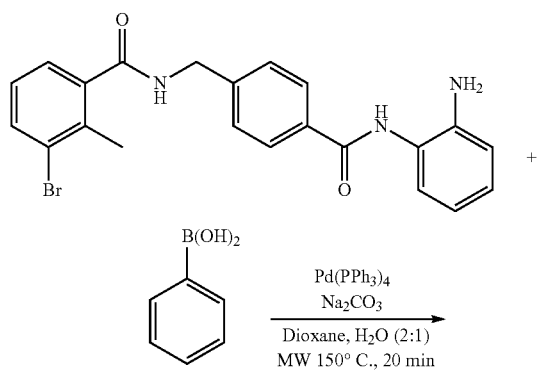

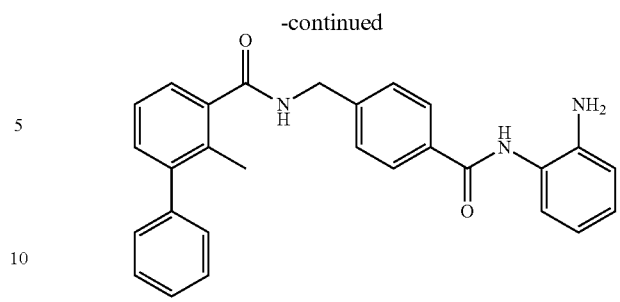

45 mg of N-(2-aminophenyl)-4-((3-bromo-2-methylbenzamido) methyl)benzamide obtained in Example 68 (0.103 mmol), phenyl boronic acid (19 mg, 0.154 mmol), tetrakis (triphenylphosphin)palladium (7 mg, 0.006 mmol), and sodium bicarbonate (33 mg, 0.308 mmol) were dissolved in 5 mL of dioxane/$H_2O$ mixture (v/v, 4:1). The resulting mixture was subjected to microwave equipment (Biotage AB) for 20 min at 150° C. Ethyl acetate was added to the resulting mixture, dried with anhydrous magnesium sulfate, and filtered with Celite. The filtrate was dried under a reduced pressure, and subjected to a column chromatography (ethyl acetate: methanol=9:1 (v:v)). The resulting mixture was dissolved in ethanol and dried to obtain the title compound (23 mg, 52%).

$^1$H NMR (300 MHz, DMSO-$d_6$): δ 9.62 (s, 1H), 8.96 (t, 1H, J=6.2 Hz), 7.94 (d, 2H, J=8.2 Hz), 7.45 (t, 4H, J=8.3 Hz), 7.39-7.36 (m, 1H), 7.34 (d, 1H, J=2.0 Hz), 7.31 (d, 2H, J=1.35 Hz), 7.28 (t, 1H, J=1.4 Hz), 7.25 (dd, 1H, J=7.0 Hz, 2.2 Hz), 7.15 (d, 1H, J=7.8 Hz), 6.95 (td, 1H, J=8.2 Hz, 1.6 Hz), 6.76 (dd, 1H, J=8.0 Hz, 1.3 Hz), 6.58 (td, 1H, J=8.8 Hz, 1.3 Hz), 4.87 (brs, 2H), 4.51 (d, 2H, J=6.0 Hz), 2.16 (s, 3H).

Example 70

Preparation of N-(2-aminophenyl)-4-((2-methyl-3-(5-pyrimidinyl)benzamido)methyl)benzamide The procedure of Example 69 was repeated except for using pyrimidin-5-yl-5-boronic acid (19 mg, 0.154 mmol) instead of phenyl boronic acid, to obtain the title compound (28 mg, 62%).

$^1$H NMR (300 MHz, DMSO-$d_6$): δ 9.62 (s, 1H), 9.21 (s, 1H), 9.00 (t, 1H, J=5.9 Hz), 8.83 (s, 2H), 7.95 (d, 2H, J=8.2 Hz), 7.48-7.45 (m, 3H), 7.40 (d, 1H, J=3.3 Hz), 7.38 (s, 1H), 7.15 (d, 1H, J=7.9 Hz), 6.95 (td, 1H, J=8.7 Hz, 1.5 Hz), 6.76 (dd, 1H, J=8.0 Hz, 1.4 Hz), 6.58 (td, 1H, J=8.8 Hz, 1.3 Hz), 4.87 (brs, 2H), 4.52 (d, 2H, J=6.1 Hz), 2.21 (s, 3H).

Example 71

Preparation of N-(2-aminophenyl)-4-((2-methyl-3-(3-pyridinyl)benzamido)methyl)benzamide The procedure of Example 69 was repeated except for using pyridin-3-yl-boronic acid (19 mg, 0.154 mmol) instead of phenyl boronic acid, to obtain the title compound (25 mg, 56%).

$^1$H NMR (300 MHz, DMSO-$d_6$): δ 9.63 (s, 1H), 8.98 (t, 1H, J=6.0 Hz), 8.59 (dd, 1H, J=4.8 Hz, 1.6 Hz), 8.52 (d, 1H, J=1.7 Hz), 7.95 (d, 2H, J=8.2 Hz), 7.77 (dt, 1H, J=7.9 Hz, 4.0 Hz, 1.8 Hz), 7.50-7.45 (m, 3H), 7.42-7.36 (m, 2H), 7.31 (td, 1H, J=7.3 Hz, 2.0 Hz), 7.15 (d, 1H, J=7.3 Hz) 6.95 (td, 1H, J=8.0 Hz, 1.5 Hz), 6.76 (dd, 1H, J=8.0 Hz, 1.6 Hz), 6.58 (td, 1H, J=7.5 Hz, 1.2 Hz), 4.87 (brs, 2H), 4.52 (d, 2H, J=6.1 Hz), 2.18 (s, 3H).

Example 72

Preparation of N-(2-aminophenyl)-4-((2-methyl-3-(3-aminophenyl)benzmido)methyl)benzamide The procedure of Example 69 was repeated except for using 3-aminophenyl boronic acid (21 mg, 0.154 mmol) instead of phenyl boronic acid, to obtain the title compound (28 mg, 60%).

$^1$H NMR (300 MHz, DMSO-$d_6$): δ 9.63 (s, 1H), 8.94 (t, 1H, J=6.0 Hz), 7.95 (d, 2H, J=8.2 Hz), 7.46 (d, 2H, J=8.3 Hz), 7.31-7.24 (m, 2H), 7.19 (dd, 1H, J=6.8 Hz, 2.3 Hz), 7.15 (dd, 1H, J=8.0 Hz, 1.0 Hz), 7.05 (t, 1H, J=7.7 Hz), 6.95 (td, 1H, J=8.0 Hz, 1.4 Hz), 6.76 (dd, 1H, J=8.0 Hz, 1.3 Hz), 6.57 (qd, 2H, J=8.6 Hz, 1.3 Hz), 6.46 (t, 1H, J=1.7 Hz), 6.39 (d, 1H, J=7.6 Hz), 5.09 (brs, 2H), 4.90 ((brs, 2H), 4.50 (d, 2H, J=6.0 Hz), 2.16 (s, 3H).

Examples 73 to 79

As shown in the following Reaction Scheme, the inventive compounds were prepared by the method described in [Kim, J. K. et al. Org. Lett. 10:3543-3546, 2008].

Example 73

Preparation of N-(2-aminophenyl)-4-((3-bromo-4,5-dimethoxy-2-methylbenzamido)methyl)benzamide

Step 1: Preparation of methyl 4-((3-bromo-4,5-dimethoxy-2-methylbenzamide)methyl)benzoate

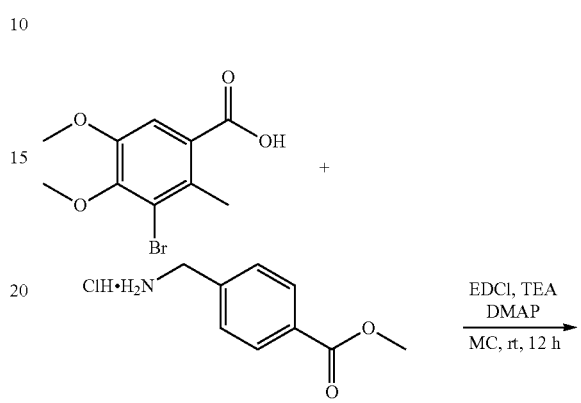

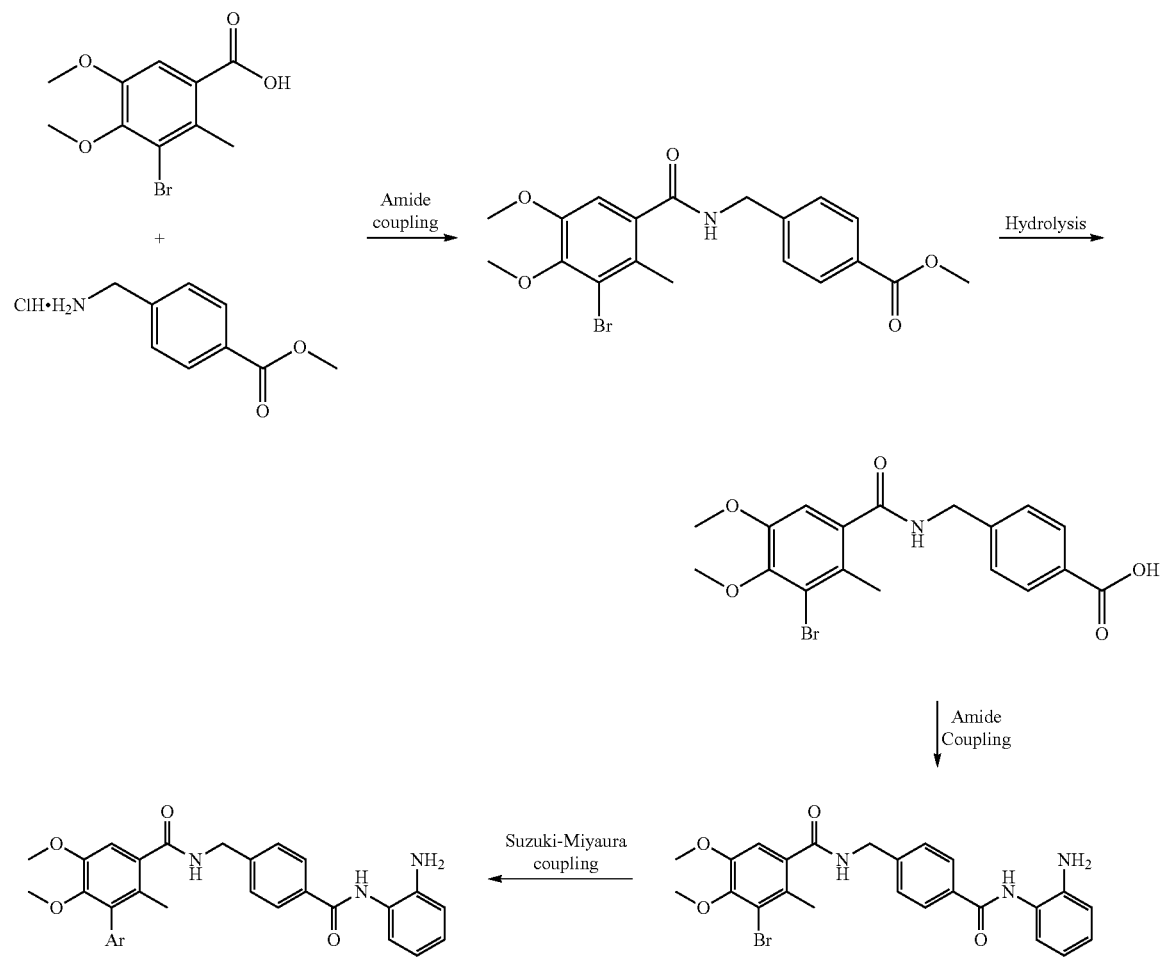

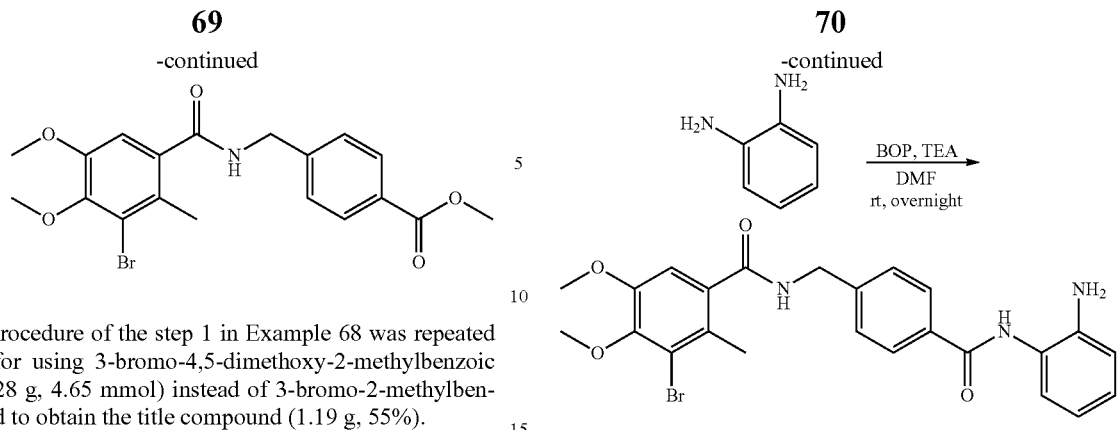

The procedure of the step 1 in Example 68 was repeated except for using 3-bromo-4,5-dimethoxy-2-methylbenzoic acid (1.28 g, 4.65 mmol) instead of 3-bromo-2-methylbenzoic acid to obtain the title compound (1.19 g, 55%).

$^1$H NMR (300 MHz, CDCl$_3$): δ 8.04 (d, 2H, J=8.3 Hz), 7.44 (d, 2H, J=8.1 Hz), 6.86 (s, 1H), 6.22 (t, 1H, J=5.4 Hz), 4.68 (d, 2H, J=5.9 Hz), 3.92 (s, 3H), 3.84 (s, 3H), 3.79 (s, 3H), 2.40 (s, 3H).

Step 2: Preparation of 4-((3-bromo-4,5-dimethoxy-2-methylbenzamido)methyl)benzoic acid

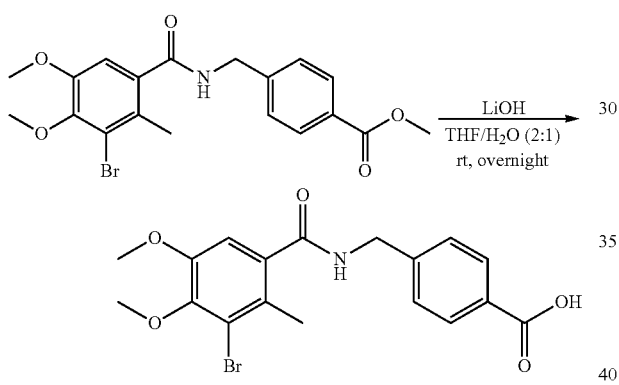

The procedure of the step 2 in Example 68 was repeated except for using methyl 4-((3-bromo-4,5-dimethoxy-2-methylbenzamido)methyl)benzoate (1.18 g, 2.80 mmol) obtained in the step 1 of Example 73 to obtain the title compound (1.08 g, 94%).

$^1$H NMR (300 MHz, DMSO-d$_6$): δ 12.86 (brs, 1H), 8.91 (t, 1H, J=5.4 Hz) 7.89 (d, 2H, J=8.4 Hz), 7.42 (d, 2H, J=8.2 Hz), 7.03 (s, 1H), 4.46 (d, 2H, J=5.9 Hz), 3.81 (s, 3H), 3.70 (s, 3H), 2.24 (s, 3H).

Step 3: Preparation of N-(2-aminophenyl)-4-((3-bromo-4,5-dimethoxy-2-methyl benzamido)methyl)benzamide

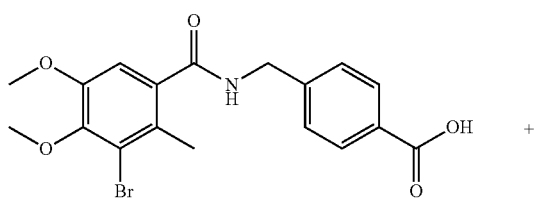

The procedure of the step 3 in Example 68 was repeated except for using methyl 4-((3-bromo-4,5-dimethoxy-2-methylbenzamido)methyl)benzoic acid (410 mg, 1.00 mmol) obtained of the step 2 in Example 73, to obtain the title compound (707 mg, 70%).

$^1$H NMR (300 MHz, DMSO-d$_6$): δ 9.63 (s, 1H), 8.94 (t, 1H, J=6.1 Hz) 7.95 (d, 2H, J=8.2 Hz), 7.45 (d, 2H, J=8.3 Hz), 7.15 (d, 1H, J=6.8 Hz) 7.05 (s, 1H), 6.95 (td, 1H, J=8.6 Hz, 1.4 Hz), 6.76 (dd, 1H, J=8.0 Hz, 1.4 Hz), 6.58 (td, 1H, J=7.6 Hz, 1.3 Hz), 4.88 (brs, 2H), 4.49 (d, 2H, J=6.0 Hz), 3.84 (s, 3H), 3.73 (s, 3H), 2.28 (s, 3H).

Example 74

Preparation of N-(2-aminophenyl)-4-((2-methyl-3-phenyl-4,5-dimethoxy-benzamido)methyl)benzamide

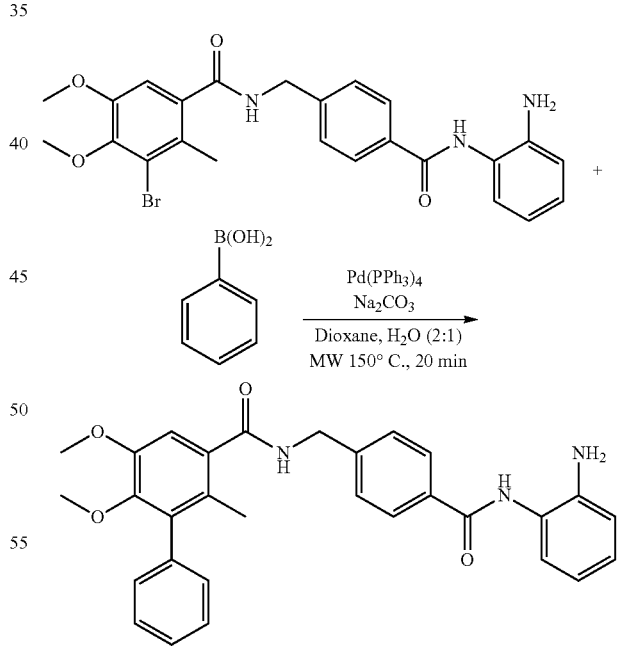

The procedure of Example 76 was repeated except for using N-(2-aminophenyl)-4-((3-bromo-4,5-dimethoxy-2-methylbenzamido)methyl)-benzamide (50 mg, 0.10 mmol) instead of the compound 1a, and phenyl boronic acid (18 mg, 0.15 mmol) to obtain the title compound (28 mg, 56%).

$^1$H NMR (300 MHz, DMSO-d$_6$): δ 9.62 (s, 1H), 8.89 (t, 1H, J=6.0 Hz), 7.94 (d, 2H, J=8.2 Hz), 7.43 (t, 4H, J=8.8 Hz), 7.36

(d, 1H, J=7.2 Hz), 7.17-7.13 (m, 3H), 7.06 (s, 1H), 6.95 (td, 1H, J=7.9 Hz, 1.4 Hz), 6.76 (dd, 1H, J=7.9 Hz, 1.2 Hz), 6.58 (td, 1H, J=7.7 Hz, 1.1 Hz), 4.87 (brs, 2H), 4.50 (d, 2H, J=5.9 Hz), 3.85 (s, 3H), 3.44 (s, 3H), 1.89 (s, 3H).

Example 75

Preparation of N-(2-aminophenyl)-4-((2-methyl-4,5-dimethoxy-3-(5-pyrimidinyl)-benzamido)methyl)benzamide The procedure of Example 74 was repeated except for using pyrimidin-5-yl-5-boronic acid (19 mg, 0.15 mmol) instead of phenyl boronic acid to obtain the title compound (41 mg, 82%).

$^1$H NMR (300 MHz, DMSO-$d_6$): δ 9.62 (s, 1H) 9.20 (s, 1H) 8.94 (t, 1H, J=5.9 Hz) 8.71 (s, 2H) 7.95 (d, 2H, J=8.2 Hz) 7.46 (d, 2H, J=8.2 Hz) 7.18 (s, 1H) 7.14 (d, 1H, J=7.7 Hz) 6.95 (td, 1H, J=7.9 Hz, 1.4 Hz) 6.76 (dd, 1H, J=8.0 Hz, 1.2 Hz) 6.58 (td, 1H, J=7.6 Hz, 1.1 Hz) 4.88 (brs, 2H), 4.51 (d, 2H, J=5.9 Hz) 3.88 (s, 3H) 3.52 (s, 3H) 1.97 (s, 3H).

Example 76

Preparation of N-(2-aminophenyl)-4-((2-methyl-3-(3-pyridinyl)-4,5-dimethoxy-benzamido)methyl)benzamide The procedure of Example 74 was repeated except for using N-(2-aminophenyl)-4-((3-bromo-4,5-dimethoxy-2-methylbenzamido)methyl)-benzamide (60 mg, 0.12 mmol) and pyridine-3-yl-3-boronic acid (22 mg, 0.18 mmol) instead of phenyl boronic acid to obtain the title compound (30 mg, 60%).

$^1$H NMR (300 MHz, DMSO-$d_6$): δ 9.62 (s, 1H), 8.92 (t, 1H, J=5.9 Hz), 8.57 (dd, 1H, J=4.8 Hz, 1.6 Hz), 8.38 (d, 1H, J=2.2 Hz), 7.94 (d, 2H, J=8.1 Hz), 7.65-7.57 (m, 2H), 7.47 (t, 2H, J=7.6 Hz), 7.14 (d, 1H, J=7.3 Hz), 7.12 (s, 1H), 6.95 (td, 1H, J=7.1 Hz, 1.3 Hz), 6.76 (d, 1H, J=7.9 Hz), 6.58 (t, 1H, J=6.9 Hz), 4.87 (brs, 2H), 4.51 (d, 2H, J=5.9 Hz), 3.86 (s, 3H), 3.47 (s, 3H) 1.92 (s, 3H).

Example 77

N-(2-aminophenyl)-4-((3-(3-aminophenyl)-4,5-dimethoxy-2-methyl-benzamido)methyl)benzamide The procedure of Example 74 was repeated except for using 3-aminophenyl boronic acid (21 mg, 0.15 mmol) instead of phenyl boronic acid to obtain the title compound (38 mg, 74%).

$^1$H NMR (300 MHz, DMSO-$d_6$): δ 9.62 (s, 1H), 8.87 (t, 1H, J=6.0 Hz), 7.94 (d, 2H, J=8.1 Hz), 7.45 (d, 2H, J=8.2 Hz), 7.15 (d, 1H, J=7.2 Hz), 7.04 (t, 1H, J=7.7 Hz), 7.00 (s, 1H), 6.95 (td, 1H, J=8.2 Hz, 1.4 Hz), 6.76 (dd, 1H, J=6.7 Hz, 1.3 Hz), 6.59 (dd, 1H, J=7.7 Hz, 1.2 Hz), 6.53 (td, 1H, J=6.8 Hz, 1.3 Hz), 6.32 (t, 1H, J=1.6 Hz), 6.26 (d, 1H, J=7.5 Hz), 5.06 (brs, 2H), 4.87 (brs, 2H), 4.49 (d, 2H, J=5.9 Hz), 3.83 (s, 3H), 3.46 (s, 3H), 1.90 (s, 3H).

Example 78

Preparation of N-(2-aminophenyl)-4-((2-methyl-3-(4-trifluoromethylphenyl)-4,5-dimethoxy-benzamido)methyl)benzamide The procedure of Example 74 was repeated except for using 4-trifluoromethylphenyl boronic acid (29 mg, 0.15 mmol) instead of phenyl boronic acid, to obtain the title compound (33 mg, 58%).

$^1$H NMR (300 MHz, DMSO-$d_6$): δ 9.62 (s, 1H), 8.91 (t, 1H, J=5.9 Hz), 7.94 (d, 2H, J=8.2 Hz), 7.79 (d, 2H, J=8.3 Hz), 7.45 (d, 2H, J=8.3 Hz), 7.41 (d, 2H, J=8.0 Hz), 7.14 (d, 1H, J=7.4 Hz), 7.11 (s, 1H), 6.95 (td, 1H, J=8.1 Hz, 1.3 Hz), 6.76 (dd, 1H, J=8.0 Hz, 1.2 Hz), 6.58 (td, 1H, J=7.6 Hz, 1.1 Hz), 4.87 (brs, 2H), 4.51 (d, 2H, J=5.9 Hz), 3.86 (s, 3H), 3.48 (s, 3H), 1.89 (s, 3H).

Example 79

Preparation of N-(2-aminophenyl)-4-((2-methyl-3-(3,5-difluorophenyl)-4,5-dimethoxy-benzamido)methyl)benzamide The procedure of Example 74 was repeated except for using 3,5-difluorophenyl boronic acid (24 mg, 0.15 mmol) instead of phenyl boronic acid, to obtain the title compound (28 mg, 52%).

$^1$H NMR (300 MHz, DMSO-$d_6$): δ 9.62 (s, 1H), 8.87 (t, 1H, J=6.4 Hz), 7.94 (d, 2H, J=8.2 Hz), 7.45 (d, 2H, J=8.2 Hz), 7.24 (tt, 1H, J=11.8 Hz, 2.3 Hz), 7.15 (d, 1H, J=7.9 Hz), 7.11 (s, 1H), 7.00-6.92 (m, 3H), 6.76 (d, 1H, J=7.9 Hz), 6.58 (td, 1H, J=7.6 Hz, 1.0 Hz), 4.87 (brs, 2H), 4.50 (d, 2H, J=5.8 Hz), 3.85 (s, 3H), 3.51 (s, 3H), 1.93 (s, 3H).

Examples 80 to 84

The inventive compounds were prepared as shown in the following Reaction Scheme:

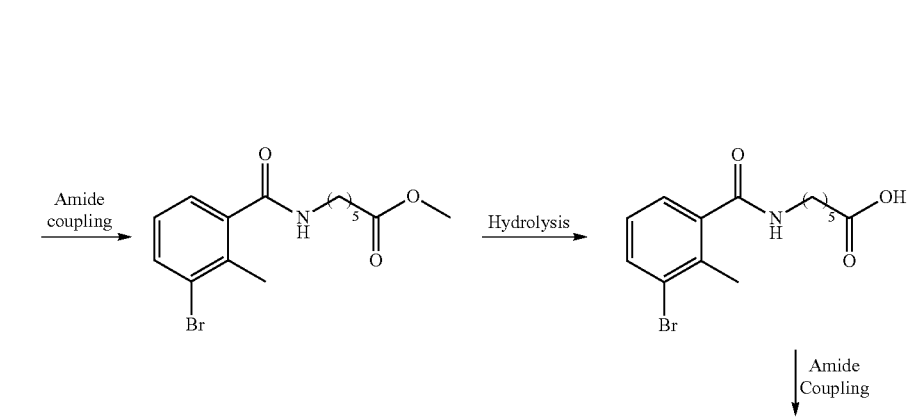

73 74

-continued

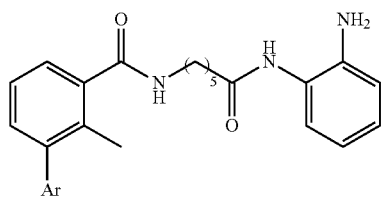
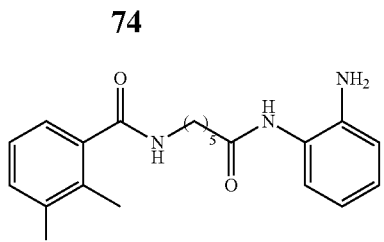

←  Suzuki-Miyaura coupling

Example 80

Preparation of N-(5-(2-aminophenylcarbamoyl)pentyl)-3-bromo-2-methylbenzamide

Step 1: Preparation of methyl 6-(3-bromo-2-methylbenzamido)hexanoate

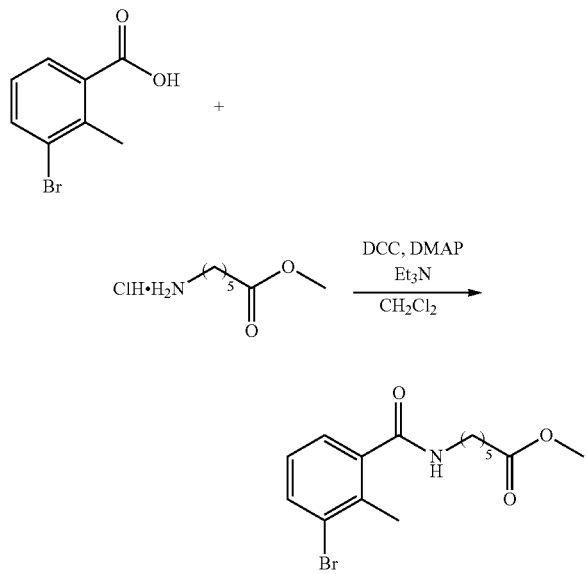

1.27 g of methyl 6-aminohexanoate hydrochloride (6.98 mmol) was dissolved in 25 ml of CH$_2$Cl$_2$ with stirring. 941 mg of triethylamine (9.3 mmol, 1.3 ml) was added to the mixture, and dicyclohexylcarbodiimide (DCC; 1.15 g, 5.58 mmol), dimethylaminopyridine (DMAP; 56.8 mg, 10 mol %), and 3-bromo-2-methylbenzoic acid (1.00 g, 4.65 mmol) was added thereto and stirred under a nitrogen atmosphere. After 24 hrs, the resulting mixture was subjected to thin layer chromatography to monitor the amount of the starting materials consumed, and the reaction was terminated by adding H$_2$O thereto and extracted with CH$_2$Cl$_2$. The separated organic layer was dried over MgSO$_4$ and removed the solvent under a reduced pressure. The residue thus obtained was subjected to a column chromatography (hexane:ethyl acetate=1:1, v/v) to obtain the title compound (497 mg, 31%).

$^1$H NMR (300 MHz, CDCl$_3$): δ 7.58 (d, 1H, J=7.95 Hz), 7.26-7.23 (m, 1H), 7.06 (t, 1H, J=7.785 Hz), 5.76 (s, 1H), 3.66 (s, 3H), 3.44 (q, 2H, J=6.7 Hz), 2.45 (s, 3H), 2.34 (t, 2H, J=7.32 Hz), 1.73-1.58 (m, 4H), 1.46-1.38 (m, 2H).

Step 2: Preparation of 6-(3-bromo-2-methylbenzamido)hexanoic acid

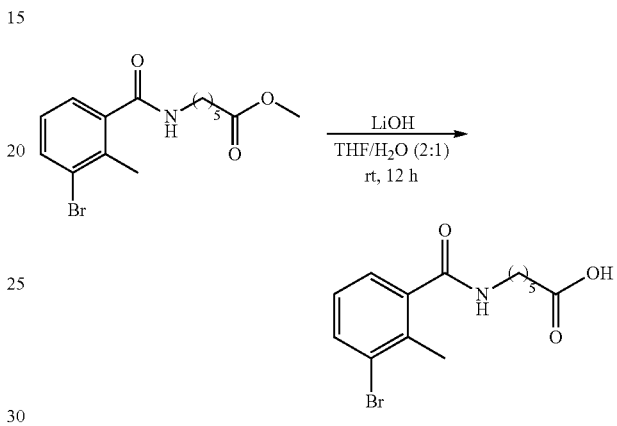

Methyl 6-(3-bromo-2-methylbenzamido)hexanoate obtained in the step 1 of Example 80 (315 mg, 0.92 mmol) and lithium hydroxide monohydrate (77 mg, 1.8 mmol) were dissolved in 9 mL of THF/H$_2$O (2:1), and stirred at room temperature for 12 hours. The resulting mixture was subjected to thin layer chromatography to monitor the amount of the starting materials consumed. 1N HCl was added dropwise to the residue to adjust its pH to 2. The resulting mixture was extracted with CH$_2$Cl$_2$, the separated organic layer was dried with MgSO$_4$, and the solvent was removed under a reduced pressure to obtain the title compound (301 mg, 99%).

$^1$H NMR (300 MHz, CDCl$_3$): δ 7.59 (d, 1H, J=8.01 Hz), 7.26-7.23 (m, 1H), 7.06 (t, 1H, J=7.785 Hz), 5.80 (t, 1H, J=4.89 Hz), 3.44 (q, 2H, J=6.69 Hz), 2.45 (s, 3H), 2.38 (t, 2H, J=7.245 Hz), 1.74-1.59 (m, 4H), 1.49-1.41 (m, 2H).

Step 3: Preparation of N-(5-(2-aminophenylcarbamoyl)pentyl)-3-bromo-2-methylbenzamide

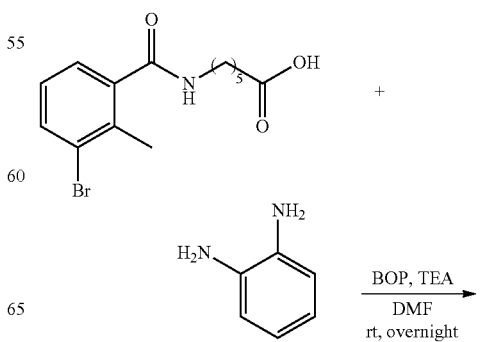

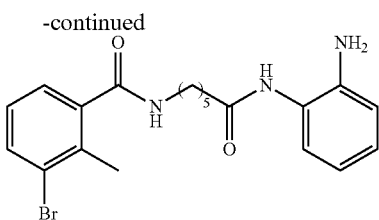

6-(3-Bromo-2-methylbenzamido)hexanoic acid obtained in the step 2 of Example 80 (200 mg, 0.609 mmol), phenylenediamine (132 mg, 1.22 mmol), 1H-benzothiazol-1-yloxytris-(dimethylamino)phosphonium hexafluorophosphate (BOP; 404 mg (0.914 mmol)) and 0.2 ml of triethylamine (1.22 mmol) were dissolved in 1.2 mL of DMF and stirred at room temperature for 36 hours. The resulting mixture was subjected to thin layer chromatography to monitor the amount of the starting materials consumed. When the reaction was terminated, $H_2O$ was added thereto, and extracted with ethyl acetate. The separated organic layer thus obtained was dried with anhydrous magnesium sulfate and distilled. The residue thus obtained was subjected to a column chromatography (methylene chloride:methanol=9:1, v/v) to obtain the title compound (173 mg, 68%).

$^1$H NMR (300 MHz, DMSO-$d_6$): δ 9.08 (s, 1H), 8.36 (t, 1H, J=8.36 Hz), 7.62 (d, 1H, J=7.92 Hz), 7.24 (d, 1H, J=4.98 Hz), 7.14 (t, 2H, J=7.68 Hz), 6.87 (t, 1H, J=7.62 Hz), 6.69 (d, 1H, J=7.98 Hz), 6.51 (t, 1H, J=7.545 Hz), 4.80 (s, 2H), 3.21 (q, 2H, J=6.38 Hz), 2.33-2.28 (m, 5H), 1.63-1.47 (m, 4H), 1.40-1.32 (m, 2H).

Example 81

Preparation of N-(5-(2-aminophenylcarbamoyl)pentyl)-2-methyl-3-phenyl-benzamide

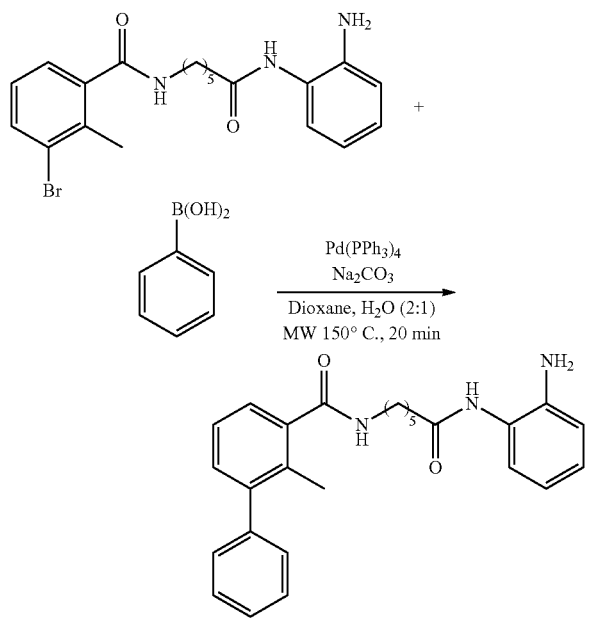

39 mg of the compound 1m obtained in the step 3 of Example 80 (0.093 mmol), phenyl boronic acid (17 mg, 0.140 mmol), tetrakis(triphenylphosphin)palladium (7 mg, 0.006 mmol) and sodium carbonate (30 mg, 0.30 mmol) were dissolved in 5 mL of dioxane/$H_2O$ mixture (v/v, 4:1). The resulting mixture was subjected to a microwave equipment (Biotage AB) for 20 min at 150° C. Ethyl acetate was added to the resulting mixture, dried with anhydrous magnesium sulfate, and filtered with celite. The filtrate was dried under a reduced pressure, and subjected to a column chromatography using ethyl acetate. Then a preparative HPLC (C18, 20% $H_2O$/$CH_3CN$, 20 ml/min) was performed to obtain the purified form of the title compound (25 mg, 64%).

$^1$H NMR (300 MHz, DMSO-$d_6$): δ 9.08 (s, 1H), 8.32 (t, 1H, J=8.36 Hz), 7.64-7.53 (m, 2H,), 7.47-7.35 (m, 3H), 7.31-7.20 (m, 5H), 7.14 (d, 1H, J=9 Hz), 6.87 (t, 1H, J=7.575 Hz), 6.70 (d, 1H, J=8.01 Hz), 6.51 (t, 1H, J=7.53 Hz), 4.81 (s, 2H), 3.24 (q, 2H, J=6.5 Hz), 2.32 (t, 2H, J=7.32 Hz), 2.15 (s, 3H), 1.64-1.50 (m, 4H), 1.42-1.35 (m, 2H).

Example 82

Preparation of N-(5-(2-aminophenylcarbamoyl)pentyl)-2-methyl-3-(2,4-dimethoxyphenyl)-benzamide The procedure of Example 81 was repeated except for using 2,4-dimethoxyphenyl boronic acid instead of phenyl boronic acid to obtain the title compound (27 mg, 58%).

$^1$H NMR (300 MHz, DMSO-$d_6$): δ 9.08 (s, 1H), 8.30 (t, 1H, J=5.535 Hz), 7.21 (s, 1H,), 7.19 (s, 1H), 7.16-7.08 (m, 2H), 6.96 (d, 1H, J=8.22 Hz), 6.88 (t, 1H, J=7.59 Hz), 6.71 (dd, 1H, J=7.98 Hz, 1.32 Hz), 6.65 (d, 1H, J=2.28 Hz), 6.59 (d, 1H, J=2.28 Hz), 6.52 (t, 1H, J=7.515 Hz), 4.81 (s, 2H), 3.81 (s, 3H), 3.69 (s, 3H), 3.23 (q, 2H, J=6.17 Hz), 2.32 (t, 2H, J=7.35 Hz), 2.00 (s, 3H), 1.65-1.52 (m, 4H), 1.42-1.35 (m, 2H).

Example 83

Preparation of N-(5-(2-aminophenylcarbamoyl)pentyl)-2-methyl-3-(3-pyridinyl)-benzamide The procedure of Example 81 was repeated except for using 3-pyridinyl boronic acid instead of phenyl boronic acid to obtain the title compound (24 mg, 79%).

$^1$H NMR (300 MHz, DMSO-$d_6$) δ 9.08 (s, 1H), 8.58 (dd, 1H, J=4.8 Hz, 1.59 Hz), 8.51 (d, 1H, J=1.65 Hz), 8.34 (t, 1H, J=5.64 Hz), 7.77-7.73 (m, 1H,), 7.47 (dd, 1H, J=7.8 Hz, 4.86 Hz), 7.32-725 (m, 2H), 7.13 (d, 1H, J=7.83 Hz), 6.96 (d, 1H, J=8.22 Hz), 6.86 (t, 1H, J=7.575 Hz), 6.68 (d, 1H, J=7.98 Hz), 6.49 (t, 1H, J=7.53 Hz), 4.80 (s, 2H), 3.23 (q, 2H, J=6.39 Hz), 2.30 (t, 2H, J=7.35 Hz), 2.15 (s, 3H), 1.63-1.51 (m, 4H), 1.41-1.33 (m, 2H).

Example 84

Preparation of N-(5-(2-aminophenylcarbamoyl)pentyl)-2-methyl-3-(4-pyridinyl)-benzamide The procedure of Example 81 was repeated except for using 4-pyridinyl boronic acid instead of phenyl boronic acid to obtain the title compound (15 mg, 76%).

$^1$H NMR (300 MHz, DMSO-$d_6$): δ 9.07 (s, 1H), 8.63-8.61 (m, 2H), 8.34 (t, 1H, J=5.475 Hz), 7.34-7.30 (m, 4H,), 7.26 (q, 1H, J=4.28 Hz), 7.13 (d, 1H, J=7.8 Hz), 6.86 (t, 1H, J=7.68 Hz), 6.68 (d, 1H, J=7.92 Hz), 6.50 (t, 1H, J=7.53 Hz), 4.79 (s, 2H), 3.23 (q, 2H, J=6.35 Hz), 2.30 (t, 2H, J=7.305 Hz), 2.16 (s, 3H), 1.66-1.48 (m, 4H), 1.41-1.33 (m, 2H).

Examples 85 to 91

The inventive compounds were prepared as shown in the following Reaction Scheme:

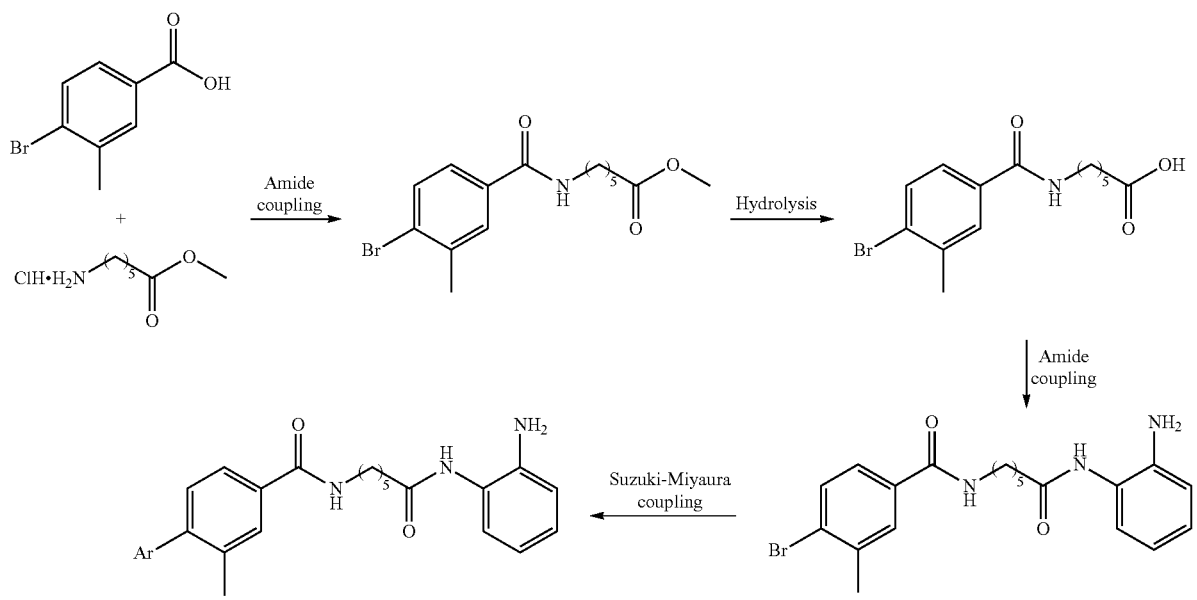

Example 85

Preparation of N-(5-(2-aminophenylcarbamoyl)pentyl)-4-bromo-3-methylbenzamide

Step 1: Preparation of methyl 6-(4-bromo-3-benzamido)hexanoate

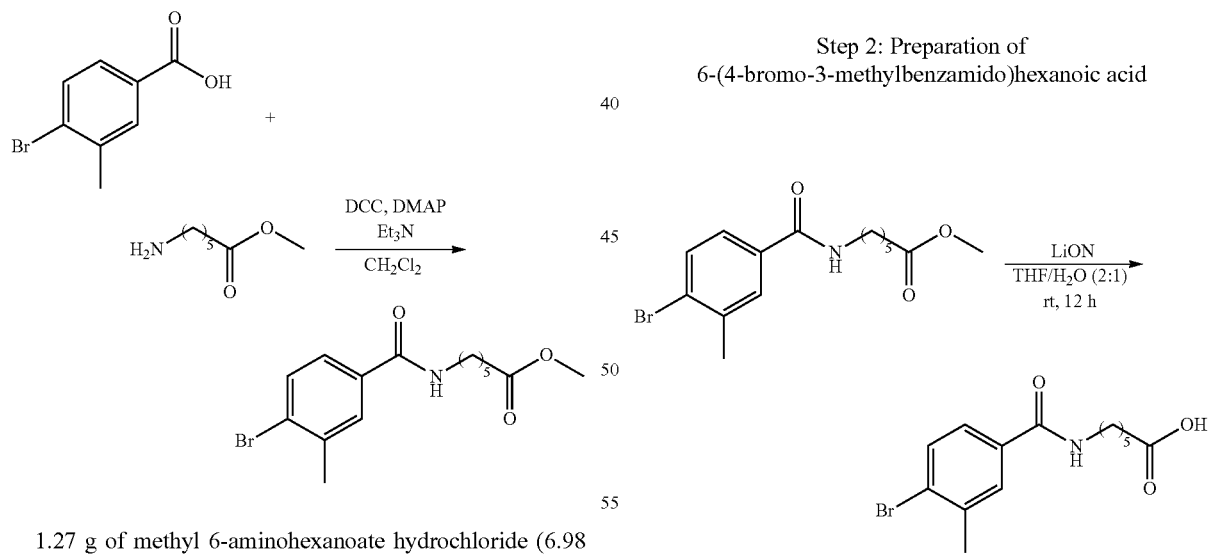

1.27 g of methyl 6-aminohexanoate hydrochloride (6.98 mmol) was dissolved in 20 mL of $CH_2Cl_2$ with stirring. 941 mg of trimethylamine (9.3 mmol, 1.3 mL) was added to the mixture and 1-ethyl-3-(3-dimethylaminopropyl)-carbodiimide hydrochloride (EDCI; 1.07 g, 5.58 mmol), dimethylaminopyridine (DMAP; 56.8 mg (10 mol %)), and 4-bromo-3-methylbenzoic acid (1.00 g, 4.65 mmol) were added thereto and stirred under a nitrogen atmosphere. After 20 hrs, the resulting mixture was subjected to thin layer chromatography to monitor the amount of the starting materials consumed. The reaction was terminated by adding $H_2O$ and extracted with $CH_2Cl_2$. The separated organic layer was dried with $MgSO_4$ and the solvent was removed under a reduced pressure. The residue thus obtained was subjected to a column chromatography (hexane:ethyl acetate=1:1, v/v), to obtain the title compound (1.25 g, 78%).

$^1$H NMR (300 MHz, $CDCl_3$): δ 7.65 (s, 1H), 7.57 (d, 1H, J=8.25 Hz), 7.41 (d, 1H, J=8.16 Hz), 6.19 (s, 1H), 3.66 (s, 3H), 3.45 (q, 2H, J=6.63 Hz), 2.43 (s, 3H), 2.33 (t, 2H, J=7.26 Hz), 1.72-1.58 (m, 4H), 1.44-1.38 (m, 2H).

Step 2: Preparation of 6-(4-bromo-3-methylbenzamido)hexanoic acid

The procedure of the step 2 in Example 80 was repeated except for using methyl 6-(4-bromo-3-benzamido)hexanoate (505 mg, 1.48 mmol) instead of methyl 6-(3-bromo-2-methylbenzamido)hexanoate, and lithium hydroxide monohydrate (124 mg, 2.95 mg), to obtain the title compound (475 mg, 98%).

$^1$H NMR (300 MHz, $CDCl_3$): δ 7.64 (s, 1H), 7.57 (d, 1H, J=8.25 Hz), 7.39 (dd, 1H, J=8.22 Hz, 1.92 Hz), 6.18 (t, 1H,

J=2.82 Hz), 3.45 (q, 2H, J=6.66 Hz), 2.43 (s, 3H), 2.38 (t, 2H, J=7.26 Hz), 1.74-1.59 (m, 4H), 1.49-1.41 (m, 2H).

Step 3: Preparation of N-(5-(2-aminophenylcarbamoyl)pentyl)-4-bromo-3-methylbenzamide

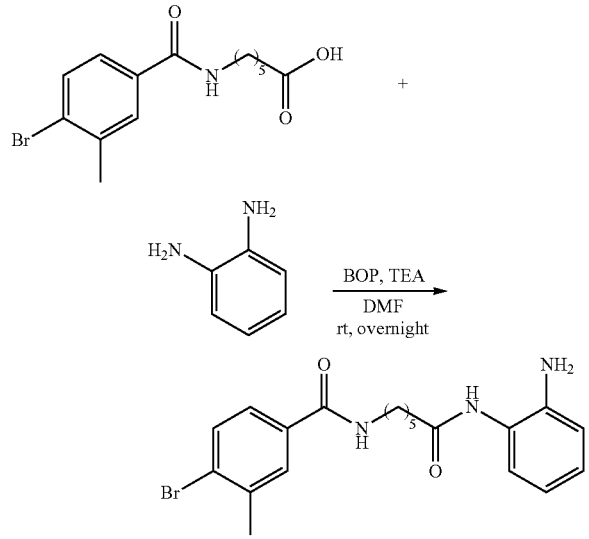

The procedure of the step 3 in Example 80 was repeated except for using 6-(4-bromo-3-methylbenzamido)hexanoic acid (300 mg, 0.914 mmol) instead of 6-(3-bromo-2-methylbenzamido)hexanoic acid, to obtain the title compound (349 mg, 91%).

$^1$H NMR (300 MHz, DMSO-d$_6$): δ 9.08 (s, 1H), 8.50 (t, 2H, J=5.505 Hz), 8.34 (t, 1H, J=5.475 Hz), 7.34-7.30 (m, 4H), 7.26 (q, 1H, J=4.28 Hz), 7.13 (d, 1H, J=7.8 Hz), 6.86 (t, 1H, J=7.68 Hz), 6.68 (d, 1H, J=7.92 Hz), 6.50 (t, 1H, J=7.53 Hz), 4.79 (s, 2H), 3.23 (q, 2H, J=6.35 Hz), 2.30 (t, 2H, J=7.305 Hz), 2.16 (s, 3H), 1.66-1.48 (m, 4H), 1.41-1.33 (m, 2H).

Example 86

Preparation of N-(5-(2-aminophenylcarbamoyl)pentyl)-3-methyl-4-phenyl-benzamide

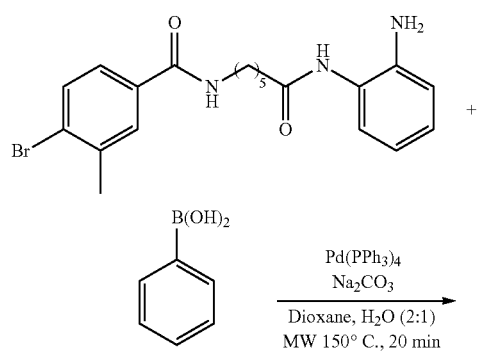

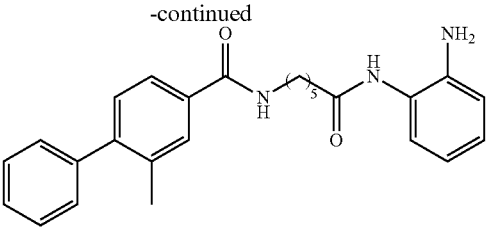

The procedure of Example 81 was repeated except for using N-(5-(2-aminophenylcarbamoyl)pentyl)-4-bromo-3-methylbenzamide instead of N-(5-(2-aminophenylcarbomoyl)pentyl)-3-bromo-2-methylbenzamide (compound 1m) to obtain the title compound (32 mg, 75%).

$^1$H NMR (300 MHz, CDCl$_3$): δ 7.70-7.57 (m, 3H), 7.49-7.36 (m, 5H), 7.30-7.18 (m, 3H), 7.03 (t, 1H, J=7.635 Hz), 6.77-6.73 (m, 2H), 6.41 (t, 1H, J=5.325 Hz), 3.86 (s, 2H), 3.50 (q, 2H, J=6.56 Hz), 2.44 (t, 2H, J=7.245 Hz), 2.27 (s, 3H), 1.87-1.77 (m, 2H), 1.73-1.64 (m, 2H), 1.55-1.48 (m, 2H).

Example 87

Preparation of N-(5-(2-aminophenylcarbamoyl)pentyl)-3-methyl-4-(2,4-dimethoxyphenyl)-benzamide The procedure of Example 81 was repeated except for using N-(5-(2-aminophenylcarbamoyl)pentyl)-4-bromo-3-methylbenzamide instead of N-(5-(2-aminophenylcarbomoyl)pentyl)-3-bromo-2-methylbenzamide, and 2,4-dimethoxyphenyl boronic acid instead of phenyl boronic acid to obtain the title compound (38 mg, 66%).

$^1$H NMR (300 MHz, CDCl$_3$): δ 7.64 (s, 1H), 7.55 (d, 1H, J=8.04 Hz), 7.49-7.43 (m, 1H), 7.21-7.17 (m, 2H), 7.02 (d, 1H, J=8.61 Hz), 6.78-6.74 (m, 2H), 6.57-6.54 (m, 2H), 6.36 (t, 1H, J=4.98 Hz), 3.73 (s, 2H), 3.49 (q, 2H, J=6.48 Hz), 2.43 (t, 2H, J=7.26 Hz), 2.14 (s, 3H), 1.86-1.76 (m, 2H), 1.71-1.62 (m, 2H), 1.54-1.46 (m, 2H).

Example 88

Preparation of N-(5-(2-aminophenylcarbamoyl)pentyl)-3-methyl-4-(3-pyridinyl)-benzamide The procedure of Example 81 was repeated except for using N-(5-(2-aminophenylcarbamoyl)pentyl)-4-bromo-3-methylbenzamide instead of N-(5-(2-aminophenylcarbomoyl)pentyl)-3-bromo-2-methylbenzamide, and 3-pyridinyl boronic acid instead of phenyl boronic acid to obtain the title compound (32 mg, 63%).

$^1$H NMR (300 MHz, DMSO-d$_6$): δ 9.07 (s, 1H), 8.59-8.56 (m, 2H), 8.48 (t, 1H, J=5.415 Hz), 7.82-7.80 (m, 2H), 7.74 (d, 1H, J=8.07 Hz), 7.48 (dd, 1H, J=7.845 Hz, 4.815 Hz), 7.31 (d, 1H, J=7.92 Hz), 7.12 (d, 1H, J=7.59 Hz), 6.86 (t, 1H, J=7.605 Hz), 6.69 (d, 1H, J=7.74 Hz), 6.50 (t, 1H, J=7.47 Hz), 4.79 (s, 2H), 3.28-3.23 (m, 2H), 2.33-2.26 (m, 5H), 1.64-1.53 (m, 4H), 1.37-1.33 (m, 2H).

Example 89

Preparation of N-(5-(2-aminophenylcarbamoyl)pentyl)-3-methyl-4-(4-pyridinyl)-benzamide The procedure of Example 81 was repeated except for using N-(5-(2-aminophenylcarbamoyl)pentyl)-4-bromo-3-methylbenzamide instead of N-(5-(2-aminophenylcarbomoyl)pentyl)-3-bromo-2-methylbenzamide, and 4-pyridinyl boronic acid instead of phenyl boronic acid to obtain the title compound (32 mg, 63%).

$^1$H NMR (300 MHz, DMSO-$d_6$): δ 9.07 (s, 1H), 8.85-8.63 (m, 2H), 8.49 (t, 1H, J=5.835 Hz), 7.79 (s, 1H), 7.74 (d, 1H, J=7.98 Hz), 7.41-7.38 (m, 2H), 7.31 (d, 1H, J=7.89 Hz), 7.13 (d, 1H, J=7.8 Hz), 6.86 (t, 1H, J=7.515 Hz), 6.69 (d, 1H, J=7.92 Hz), 6.50 (t, 1H, J=7.53 Hz), 4.79 (s, 2H), 3.28-3.24 (m, 2H), 2.33-2.27 (m, 5H), 1.64-1.53 (m, 4H), 1.37-1.33 (m, 2H).

Example 90

Preparation of N-(5-(2-aminophenylcarbamoyl)pentyl)-3-methyl-4-(5-pyrimidinyl)-benzamide The procedure of Example 81 was repeated except for using N-(5-(2-aminophenylcarbamoyl)pentyl)-4-bromo-3-methylbenzamide instead of N-(5-(2-aminophenylcarbomoyl)pentyl)-3-bromo-2-methylbenzamide, and 5-pyridinyl boronic acid instead of phenyl boronic acid to obtain the title compound (32 mg, 63%).

$^1$H NMR (300 MHz, DMSO-$d_6$): δ 9.21 (s, 1H), 9.07 (s, 1H), 8.87 (s, 2H), 8.51 (t, 1H, J=5.385 Hz), 7.82 (s, 1H), 7.79 (d, 1H, J=8.19 Hz), 7.39 (d, 1H, J=7.92 Hz), 7.12 (d, 1H, J=7.62 Hz), 6.86 (t, 1H, J=7.095 Hz), 6.69 (d, 1H, J=7.83 Hz), 6.50 (t, 1H, J=7.53 Hz), 4.79 (s, 2H), 3.28-3.24 (m, 2H), 2.33-2.30 (m, 5H), 1.64-1.53 (m, 4H), 1.37-1.33 (m, 2H).

Example 91

Preparation of N-(5-(2-aminophenylcarbamoyl)pentyl)-3-methyl-4-(3,5-dimethylphenyl)-benzamide The procedure of Example 81 was repeated except for using N-(5-(2-aminophenylcarbamoyl)pentyl)-4-bromo-3-methylbenzamide instead of N-(5-(2-aminophenylcarbomoyl)pentyl)-3-bromo-2-methylbenzamide, and 3,5-dimethyl phenyl boronic acid instead of phenyl boronic acid to obtain the title compound (35 mg, 77%).

$^1$H NMR (300 MHz, CDCl$_3$): δ 7.66 (s, 1H), 7.56 (d, 1H, J=8.07 Hz), 7.40 (s, 1H), 7.23-7.18 (m, 2H), 7.06-7.01 (m, 2H), 6.90 (s, 2H), 6.78-6.74 (m, 2H), 6.38 (t, 1H, J=5.235 Hz), 3.86 (s, 2H), 3.50 (q, 2H, J=6.55 Hz), 2.44 (t, 2H, J=7.23 Hz), 2.36 (s, 6H), 2.27 (s, 3H), 1.85-1.80 (m, 2H), 1.71-1.64 (m, 2H), 1.55-1.48 (m, 2H).

Examples 92 and 94

The inventive compounds were prepared as shown in the following Reaction Scheme:

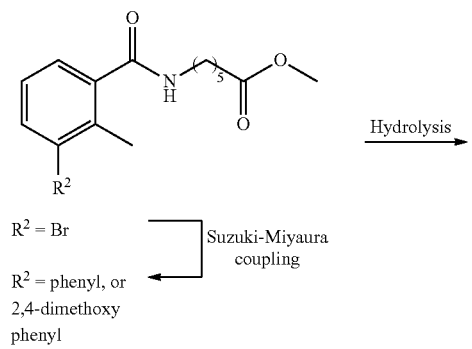

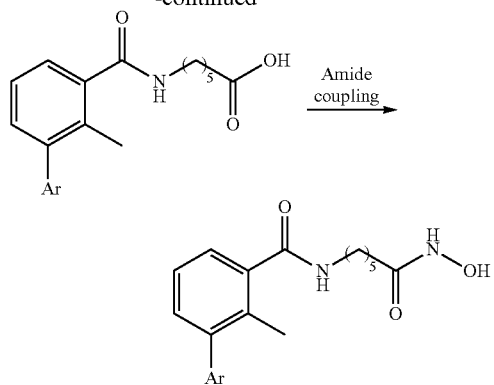

Example 92

Preparation of N-(5-(hydroxycarbamoyl)pentyl)-2-methyl-3-phenylbenzamide

Step 1: Preparation of methyl 6-(2-methyl-3-phenyl-benzamido)hexanoate

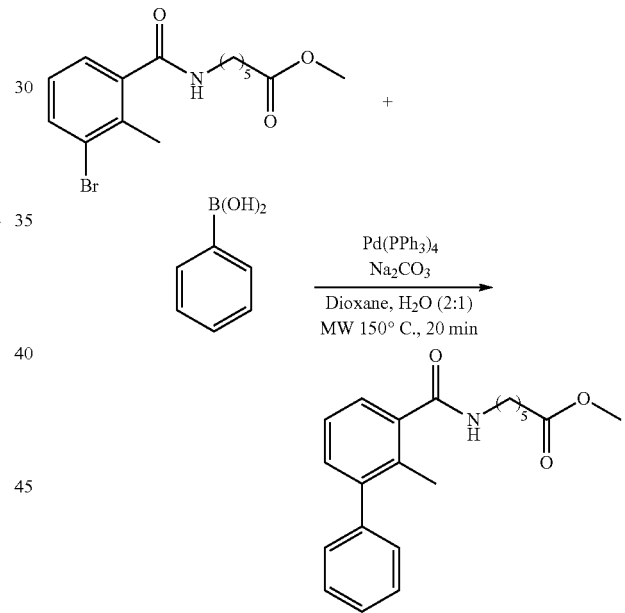

Methyl 6-(3-bromo-2-methylbenzamido)hexanoate obtained in the step 1 of Example 80 (100 mg, 0.292 mmol), phenyl boronic acid (53 mg, 0.438 mmol), tetrakis(triphenylphosphin)palladium (20 mg, 0.017 mmol) and sodium carbonate (62 mg, 0.584 mmol) were dissolved in 5 mL of dioxane/H$_2$O mixture (v/v, 4:1). The mixture was subjected to a microwave equipment (Biotage AB) for 15 min at 150° C. Ethyl acetate was added to the resulting mixture, dried with anhydrous magnesium sulfate and filtered with Celite. The filtrate was dried under a reduced pressure and subjected to a column chromatography (n-hexane:ethyl acetate=1:1) to obtain the title compound (107 mg, 99%).

$^1$H NMR (300 MHz, CDCl$_3$): δ 8.25 (d, 1H, J=7.83 Hz), 7.61-7.49 (m, 2H), 7.44-7.35 (m, 3H), 7.32-7.29 (m, 2H), 5.81 (t, 2H, J=5.16 Hz), 3.66 (s, 3H), 3.47 (q, 2H, J=6.2 Hz), 2.34 (t, 2H, J=7.08 Hz), 2.28 (s, 3H), 1.74-1.59 (m, 4H), 1.47-1.38 (m, 2H).

Step 2: Preparation of 6-(2-methyl-3-phenyl-benzamido)hexanoic acid

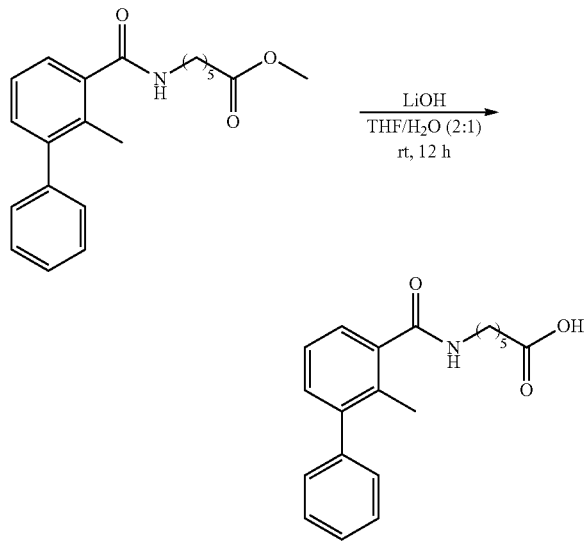

The procedure of the step 2 in Example 80 was repeated except that the methyl 6-(2-methyl-3-phenyl-benzamido)hexanoate (61 mg, 0.18 mmol) instead of methyl 6-(3-bromo-2-methylbenzamido)hexanoate, and 15 mg of lithium hydroxide monohydrate (0.36 mmol) were dissolved in 3 mL of THF/H₂O (2:1) to obtain the title compound (53 mg, 90%).

$^1$H NMR (300 MHz, CDCl$_3$): δ 8.24 (d, 1H, J=1.44 Hz), 7.61-7.49 (m, 2H), 7.44-7.35 (m, 3H), 7.32-7.29 (m, 2H), 5.83 (t, 2H, J=5.16 Hz), 3.47 (q, 2H, J=6.66 Hz), 2.37 (t, 2H, J=7.275 Hz), 2.27 (s, 3H), 1.75-1.60 (m, 4H), 1.51-1.41 (m, 2H).

Step 3: Preparation of N-(5-(hydroxycarbamoyl)pentyl)-2-methyl-3-phenyl benzamide

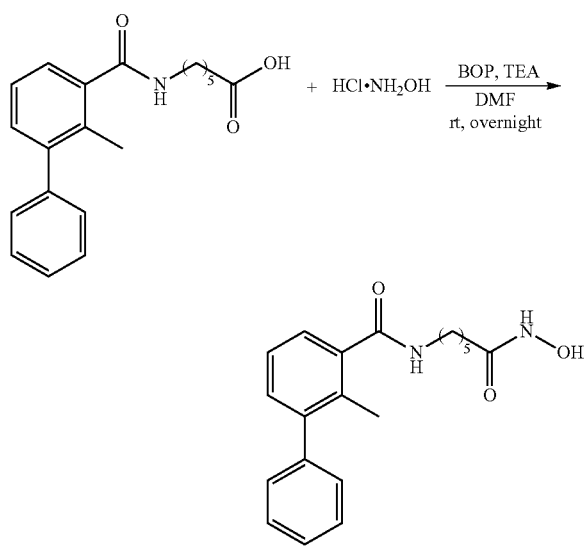

The procedure of the step 3 in Example 80 was repeated except that 6-(2-methyl-3-phenyl-benzamido)hexanoic acid (38 mg, 0.116 mmol)) instead of 6-(3-bromo-2-methylbenzamido)hexanoic acid and hydroxylamine hydrochloride (16 mg, 0.23 mmol) instead of 1,2-phenylenediamine were used and purified by a preparative HPLC (C18, 20% H₂O/CH₃CN, 20 ml/min) to obtain the title compound (8 mg, 20%).

$^1$H NMR (300 MHz, DMSO-d$_6$): δ 0.30 (s, 1H), 8.62 (s, 1H), 8.26 (t, 1H, J=5.55 Hz), 7.44-7.33 (m, 3H), 7.27-7.17 (m, 5H), 3.17 (q, 2H, J=6.42 Hz), 2.11 (s, 3H), 1.90 (t, 2H, J=7.32 Hz), 1.51-1.41 (m, 4H), 1.30-1.22 (m, 2H).

Example 93

Preparation of N-(5-(hydroxycarbamoyl)pentyl)-2-methyl-3-(2,4-dimethoxyphenyl)-benzamide

Step 1: Preparation of methyl 6-(2-methyl-3-(2,4-dimethoxyphenyl)-benzamido)hexanoate The procedure of the step 1 in Example 92 was repeated except that the methyl 6-(3-bromo-2-methylbenzamido)hexanoate (34 mg, 0.10 mmol), tetrakis(triphenylphosphin)palladium (12 mg, 0.010 mmol), sodium carbonate (21 mg, 0.20 mmol), and 2,4-dimethoxyphenyl boronic acid (27 mg, 0.15 mmol) instead of phenyl boronic acid were dissolved in 3 mL of dioxane/H₂O (4:1, v/v) to obtain the title compound (31 mg, 80%).

$^1$H NMR (300 MHz, CDCl$_3$): δ 7.30-7.27 (m, 2H), 7.21 (d, 1H, J=4.5 Hz), 7.00 (d, 1H, J=8.97), 6.55-6.53 (m, 2H), 5.83 (t, 1H, J=4.635 Hz), 3.85 (s, 3H), 3.73 (s, 3H), 3.66 (s, 3H), 3.45 (q, 2H, J=6.7), 2.33 (t, 2H, J=7.29 Hz), 2.16 (s, 3H), 1.71-1.61 (m, 4H), 1.47-1.40 (m, 2H).

Step 2: Preparation of 6-(2-methyl-3-(2,4-dimethoxyphenyl)-benzamido)hexanoic acid The procedure of the step 2 in Example 92 was repeated except that methyl 6-(2-methyl-3-(2,4-dimethoxyphenyl)-benzamido)hexanoate (30 mg, 0.075 mmol) and lithium hydroxide monohydrate (6 mg, 0.15 mmol) were dissolved in 3 mL of THF/H₂O (2:1) to obtain the title compound (27 mg, 94%).

$^1$H NMR (300 MHz, CDCl$_3$): δ 7.30-7.27 (m 1H), 7.22 (d, 1H, J=1.65 Hz), 7.20 (s, 1H), 7.00 (d, 1H, J=8.88 Hz), 6.56-6.53 (m, 2H), 5.84 (t, 1H, J=5.655 Hz), 3.85 (s, 3H), 3.73 (s, 3H), 3.46 (q, 2H, J=6.68 Hz), 2.37 (t, 2H, J=7.32 Hz), 2.16 (s, 3H), 1.72-1.59 (m, 4H), 1.50-1.42 (m, 2H).

Step 3: Preparation of N-(5-(hydroxycarbamoyl)pentyl)-2-methyl-3-(2,4-dimethoxy phenyl)-benzamide The procedure of the step 3 in Example 80 was repeated except that 6-(2-methyl-3-(2,4-dimethoxyphenyl)-benzamido)hexanoic acid instead of 6-(3-bromo-2-methylbenzamido)hexanoic acid, and hydroxylamine hydrochloride instead of 1,2-phenylenediamine were used and purified by a preparative HPLC (C18, 20% H₂O/CH₃CN, 20 ml/min) to obtain the title compound (27 mg, 35%).

$^1$H NMR (300 MHz, DMSO-d$_6$): δ 10.34 (s, 1H), 8.67 (s, 1H), 8.30 (t, 1H, J=5.49 Hz), 7.21-7.19 (m, 2H), 7.11-7.08 (m, 1H), 6.96 (d, 1H, J=8.25 Hz), 6.64 (d, 1H, J=2.28 Hz), 6.59 (dd, 1H, J=8.25 Hz, 2.366 Hz), 3.80 (s, 3H), 3.69 (s, 3H), 3.19 (q, 2H, J=6.43 Hz), 1.99 (s, 3H), 1.94 (t, 2H, J=7.35 Hz), 1.53-1.44 (m, 4H), 1.33-1.25 (m, 2H).

Example 94

Preparation of N-(5-(hydroxycarbamoyl)pentyl)-3-methyl-4-phenylbenzamide

The inventive compounds may be prepared as shown in the following Reaction Scheme:

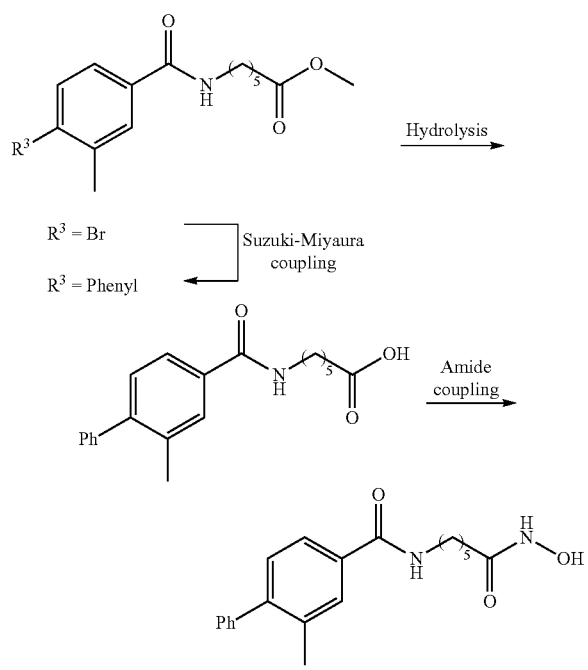

Step 1: Preparation of methyl 6-(3-methyl-4-phenyl-benzamido)hexanoate

The procedure of the step 1 in Example 92 was repeated except for using methyl 6-(4-bromo-3-methylbenzamido)hexanoate (200 mg, 0.584 mmol) instead of methyl 6-(3-bromo-2-methylbenzamido)hexanoate to obtain the title compound (195 mg, 98%).

$^1$H NMR (300 MHz, CDCl$_3$): δ 8.24 (d, 1H, J=6.66 Hz), 7.71 (s, 1H), 7.63-7.47 (m, 3H), 7.44-7.35 (m, 3H), 7.30-7.24 (m, 2H), 6.51 (t, 1H, J=5.43 Hz), 3.63 (s, 3H), 3.47 (q, 2H, J=6.65 Hz), 2.35-2.28 (m, 5H), 1.72-1.59 (m, 4H), 1.46-1.36 (m, 2H).

Step 2: Preparation of 6-(3-methyl-4-phenyl-benzamido)hexanoic acid

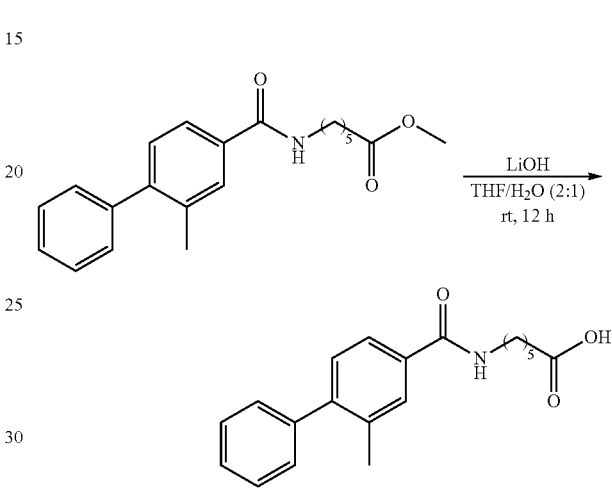

The procedure of the step 2 in Example 80 was repeated except for using methyl 6-(3-methyl-4-phenyl-benzamido)hexanoate (195 mg, 0.574 mmol) instead of methyl 6-(3-bromo-2-methylbenzamido)hexanoate, and lithium hydroxide monohydrate (54 mg, 1.29 mmol) to obtain the title compound (186 mg, 99%).

$^1$H NMR (300 MHz, CDCl$_3$): δ 8.25 (d, 1H, J=6.57 Hz), 7.69 (s, 1H), 7.59 (d, 1H, J=8.34 Hz), 7.51 (t, 1H, J=7.185 Hz), 7.45-7.36 (m, 3H), 7.31 (s, 1H), 7.29 (s, 1H), 6.23 (t, 1H, J=5.31 Hz), 3.49 (q, 2H, J=6.65 Hz), 2.39 (t, 2H, J=7.305 Hz), 2.30 (s, 3H), 1.75-1.61 (m, 4H), 1.51-1.42 (m, 2H).

Step 3: Preparation of N-(5-(hydroxycarbamoyl)pentyl)-3-methyl-4-phenyl benzamide

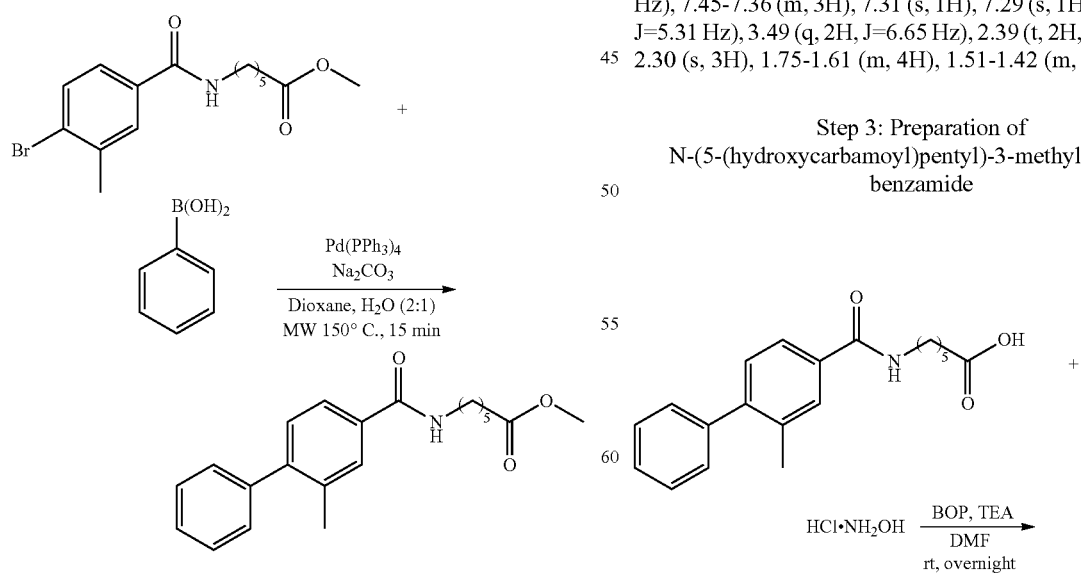

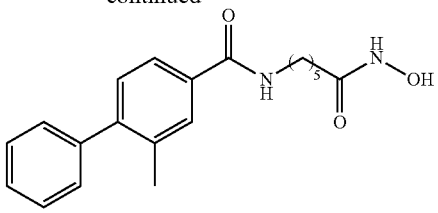

The procedure of the step 3 in Example 80 was repeated except that 6-(3-methyl-4-phenyl-benzamido)hexanoic acid (70 mg (0.215 mmol)) instead of 6-(3-bromo-2-methylbenzamido)hexanoic acid, and 30 mg of hydroxylamine hydrochloride (0.43 mmol) instead of 1,2-phenylenediamine were used and purified by a preparative HPLC (C18, 20% $H_2O$/ $CH_3CN$, 20 ml/min) to obtain the title compound (38 mg, 51%).

$^1H$ NMR (300 MHz, DMSO-$d_6$): δ 10.34 (s, 1H), 8.67 (s, 1H), 8.45 (t, 1H, J=5.49 Hz), 7.77 (s, 1H), 7.71 (d, 1H, J=7.89 Hz), 7.49-7.34 (m, 5H), 7.27 (d, 1H, J=7.92 Hz), 3.25 (q, 2H, J=6.54 Hz), 2.25 (s, 3H), 1.95 (t, 2H, J=7.32 Hz), 1.57-1.47 (m, 4H), 1.32-1.23 (m, 2H).

Experimental Example 1

Effect of Amide Compound on Runx2

Mouse premyoblast cell (C2C12 cell) was transfected using receptor vector 6xOSE2-Luc in order to investigate the activity of the amide compound of the present invention on Runx2.

Specifically, the receptor vector 6xOSE2-Luc was prepared by inserting an artificial promoter linked by six tandem copies of the OSE2 (osteoblast specific element-2) into vector pGL3 (Promega; Madison, Wis., U.S.A.), and then, cloned into the C2C12 cell to be transfected (Kim et al., *Journal of Cellular Biochemistry*, 91: 1239-1247, 2004). The OSE2 is the binding site of Runx2 in the promoter of osteocalcin which is a bone marker.

C2C12 cells (5,000 cells/well) were plated onto 96-well plates using 10% FBS (fetal bovine serum; Hyclone)-containing DMEM (Dulbecco's Modified Eagle's Medium), the medium was replaced with 5% FBS-containing DMEM after 24 hrs, and treated with each of the amide compounds obtained in Examples 1 to 94 at various concentrations of 2.5 μM, 5.0 μM, 10 μM, and 20 μM. As a control, dimethyl sulfoxide (DMSO) vehicle was applied to the cell in an amount same as that of the amide compound. After 24 hrs, the luciferase activity in the cell lysate was measured by using Dual-Luciferase Reporter Assay System (Promega). The luciferase activity of the amide compound of the present invention was calculated as a value relative to that observed for the control which was set as 1. The results are given in Table 1.

TABLE 1

| Example No. | Dosage | | | |
| --- | --- | --- | --- | --- |
| | 2.5 μM | 5.0 μM | 10 μM | 20 μM |
| 1 | 21.4 | 26.2 | 19.9 | 15.8 |
| 2 | 27.3 | 24.8 | 19.7 | 21.7 |
| 3 | 25.2 | 25.7 | 22.7 | 18.7 |
| 4 | 37 | 42.2 | 36.6 | 36.7 |
| 5 | 30.4 | 25.3 | 17.7 | 15.4 |
| 6 | 14.2 | 18.3 | 17.2 | 9.3 |
| 7 | 24.6 | 26.9 | 24.3 | 18.4 |
| 8 | 28.5 | 33.4 | 36 | 30.1 |
| 9 | 12.4 | 11.3 | 9.7 | 9.4 |
| 10 | 7.9 | 11.6 | 14.4 | 16.7 |
| 11 | 8.3 | 12.3 | 15.6 | 16.8 |
| 12 | 5.5 | 9 | 12.2 | 10.4 |
| 13 | 7.9 | 8 | 9.3 | 7.2 |
| 14 | 12 | 15.7 | 15.4 | 16.9 |
| 15 | 7.4 | 10.4 | 12 | 14 |
| 16 | 12.2 | 12.3 | 8.5 | 9.2 |
| 17 | 11.2 | 14.7 | 16.3 | 15.8 |
| 18 | 15.3 | 16.2 | 20.2 | 18.5 |
| 19 | 10.8 | 9.9 | 11.7 | 14 |
| 20 | 16.2 | 19.4 | 19.3 | 16.8 |
| 21 | 6.4 | 8.7 | 11.6 | 11.7 |
| 22 | 12.4 | 9.5 | 10.2 | 10.3 |
| 23 | 3.9 | 5.1 | 18.1 | 33.2 |
| 24 | 11.8 | 17.3 | 19.6 | 21.2 |
| 25 | 6.8 | 11.3 | 17.9 | 19.7 |
| 26 | 1.6 | 2.3 | 4.4 | 18.4 |
| 27 | 9.9 | 17.5 | 22.5 | 20.3 |
| 28 | 4.6 | 7.7 | 14.3 | 23.7 |
| 29 | 3.4 | 5.6 | 10.5 | 10 |
| 30 | 13.5 | 20.5 | 28.8 | 30.4 |
| 31 | 12.2 | 21.2 | 26.2 | 29.3 |
| 32 | 4.4 | 9.2 | 18.5 | 23.8 |
| 33 | 1.8 | 3.4 | 10 | 29 |
| 34 | 3.7 | 7.4 | 18 | 23 |
| 35 | 2.9 | 6.7 | 14.2 | 22.3 |
| 36 | 2.1 | 3 | 8 | 13 |
| 37 | 1.6 | 2.6 | 6.8 | 12.5 |
| 38 | 3 | 8.2 | 23 | 43.3 |
| 39 | 1.4 | 2.1 | 5.3 | 25.6 |
| 40 | 1.1 | 1.1 | 1.7 | 1.6 |
| 41 | 2.5 | 4.6 | 12.4 | 28 |
| 42 | 3.1 | 10.8 | 22.3 | 17.9 |
| 43 | 1.1 | 1.3 | 1.8 | 3.2 |
| 44 | 1.2 | 1.2 | 1.3 | 1.4 |
| 47 | 1.1 | 1.2 | 1.3 | 1.6 |
| 48 | 3.7 | 7.2 | 11.4 | 14.3 |
| 49 | 4.8 | 10.6 | 28.1 | 26.5 |
| 50 | 1.9 | 5 | 22.1 | 42.7 |
| 51 | 1.2 | 2.1 | 10.4 | 26.4 |
| 52 | 2.4 | 4.7 | 12.6 | 20.4 |
| 53 | 1.7 | 3 | 5.6 | 13.3 |
| 54 | 1.5 | 2.9 | 8.9 | 19.8 |
| 55 | 2.7 | 3.7 | 5.5 | 13.3 |
| 56 | 1.1 | 1.1 | 1.1 | 1.1 |
| 57 | 7.3 | 8.9 | 10.9 | 10.7 |
| 58 | 11.7 | 17.1 | 21.6 | 21.6 |
| 59 | 3.3 | 4.5 | 4.1 | 3.8 |
| 60 | 5.4 | 5.9 | 7 | 8.6 |
| 61 | 9.6 | 10.6 | 14.2 | 15.6 |
| 62 | 4.6 | 5.8 | 5.5 | 6.6 |
| 63 | 8.3 | 10.3 | 13.1 | 14.2 |
| 64 | 11.3 | 10.7 | 10.1 | 9.5 |
| 65 | 12.9 | 15.7 | 13.5 | 11.4 |
| 66 | 14.2 | 9.4 | 7.2 | 7.2 |
| 67 | 1.4 | 2 | 2.9 | 6.1 |
| 68 | 9.0 | 10.1 | 12.8 | 15.6 |
| 69 | 13.5 | 22.0 | 29.2 | 30.6 |
| 70 | 8.9 | 20.6 | 30.1 | 40.2 |
| 71 | 18.7 | 34.8 | 36.5 | 32.7 |
| 72 | 17.6 | 29.8 | 29.6 | 31.4 |
| 73 | 24.2 | 32.3 | 30.8 | 25.9 |
| 74 | 25.1 | 31.1 | 38.5 | 38.9 |
| 75 | 2.5 | 4.7 | 12.4 | 27.8 |
| 76 | 4.5 | 8.5 | 20.8 | 32.9 |
| 77 | 4.9 | 11.0 | 24.5 | 33.5 |
| 78 | 6.4 | 12.8 | 19.1 | 21.1 |
| 79 | 13.5 | 24.4 | 31.3 | 31.7 |
| 80 | 0.9 | 1.8 | 2.7 | 5.4 |
| 81 | 1.6 | 3.4 | 7.5 | 10.7 |
| 82 | 1.5 | 2.5 | 6.0 | 10.9 |
| 83 | 1.3 | 2.1 | 5.6 | 15.7 |
| 84 | 1.9 | 3.3 | 7.8 | 17.3 |

TABLE 1-continued

| Example No. | Dosage | | | |
|---|---|---|---|---|
| | 2.5 μM | 5.0 μM | 10 μM | 20 μM |
| 85 | 2.15 | 6.7 | 13.9 | 14.3 |
| 86 | 1.2 | 1.9 | 3.4 | 3.7 |
| 87 | 1.7 | 2.6 | 5.6 | 8.5 |
| 88 | 6.0 | 16.8 | 28.1 | 41.2 |
| 89 | 9.6 | 17.9 | 23.7 | 25.3 |
| 90 | 1.7 | 3.7 | 9.5 | 22.1 |
| 91 | 1.1 | 1.5 | 2.9 | 3.9 |
| 92 | 4.1 | 8.8 | 12.4 | 11.5 |
| 93 | 1.3 | 1.9 | 4.8 | 11.2 |
| 94 | 1.6 | 3.4 | 7.5 | 10.7 |

The expression of Runx2 (Cbfa1/Pebp2aA/AML3/Osf2) transcription factor having Runt domain is essential for osteoblast differentiation relating to bone formation, which was demonstrated in the studies on a gene deficiency disease of knockout mouse and human (See Komori et al., Cell, 89, 755-764, 1997; Ducy et al., Cell, 89, 747-754, 1997; Otto et al., Cell, 89, 765-772, 1997; Mundlos et al., 89, 773-779, 1997). Runx2 is a transcription factor that can regulate bone formation in the uppermost part, and the expression of Runx2 is enhanced by a bone formation-stimulating factor. Therefore, Runx2 transcription activity of the cell after administration of the inventive compound is proportional to the bone formation-inducing ability of the compound. The expression of Runx2 is critical to determine bone formation ability of the compound. Alternatively, osteocalcin, osteopontin, and bone sialoprotein, which are markers of osteoblast, have promoters containing a Runx-binding site, that is, osteoblast specific factor binding element 2 (OSE2). Thus, a compound which elevates the expression level of Runx2 may lead to the increased activity of all the promoters.

As shown in Table 1, the amide compound of the present invention shows an activity which is up to 43.3 fold higher compared with the control group. Accordingly, the amide compound of the present invention increases the expression of Runx2, and thus, it facilitates osteoblast formation and effective for the prevention and treatment of osteoporosis.

Experimental Example 2

Effect of Amide Compound on Alkaline Phosphatase (ALP)

To examine the effect of the amide compound of the present invention on a promoter activity of ALP, which is a marker of osteoblast differentiation, ALP activity was measured by using basic vector pGL3 which is luciferase-measuring vector containing a promoter region of ALP (including base sequence from −229 to +81 position of mice ALP promoter).

Specifically, according to the [Kim H J et al, Journal of Cellular Biochemistry, 91: 1239-1247, 2004], a vector was prepared by inserting mice ALP promoter (sequence No: 1) into basic vector pGL3 (Promega; Madison, Wis., U.S.A.), and then, cloned into the C2C12 cell to be transfected.

The transfected cell was treated with the compounds obtained in Example 8 or 27 respectively (5.0 μM) as a test group and DMSO vehicle as a control group, respectively. After 24 hrs, the cell was treated with phosphate-buffered-saline solution and treated with cell lysis buffer for luciferase, and then the lysed supernatant was collected. The amount of the protein in the obtained supernatant was measured, and the supernatant was added onto 96-well plate in order to be included 30 μg of protein per well. A substrate for luciferase was added thereto, and the optical density was measured by using luminometer (BMG, FlUOstar OPTIMA). The result is given in FIGS. 1 and 2.

Figure 2:
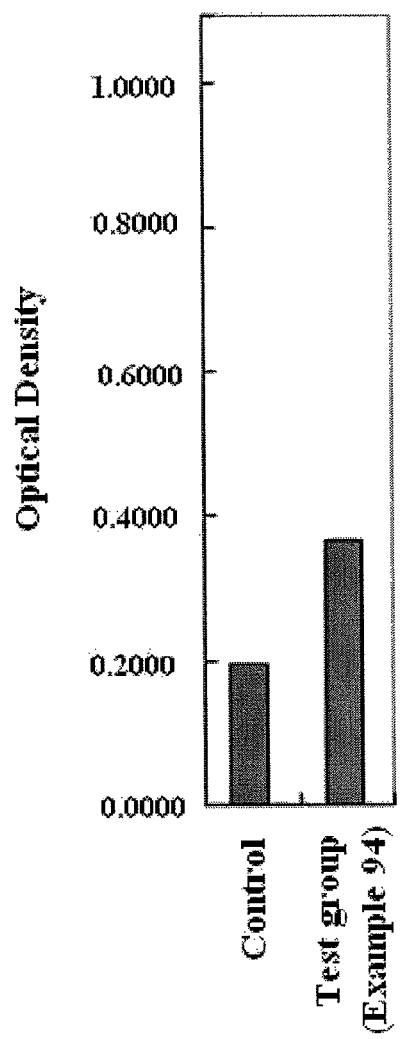
FIG. 2: the effect of the compound (Example 94) according to the present invention on the promoter activity of alkaline phosphatase, a marker of osteoblast differentiation.

As shown in FIGS. 1 and 2, it has been found that ALP activity of the test group is elevated to 2-fold or more compared to the control group. This result indicates that the amide compound of the present invention stimulates the formation of bone broken due to osteoporosis, and can be therefore used for preventing and treating osteoporosis.

Experimental Example 3

Effect on Mice Calvarias Loss Inhibition

To investigate the effect of the amide compound of the present invention on the inhibition of mice bone loss, trolox effect of the amide compound of the present invention on bone loss induced by interleukin-1 (IL-1) in vivo by using the compounds obtained in Example 8 and 27.

Specifically, 5 to 7 ml of collagen (Cellmatrix type I-A; Wako co., Japan, Cat. No. 637-00653) was poured into petri dish (60×15 mm), and lyophlilized. The lyophlilized collagen sponge was made to the desired size which is appropriate to be implanted, and in order to induce local bone loss of mice, interleukin-1 (Peprotech; London, GB) was diluted with phosphate-buffered-saline solution to 2 μg per one mouse to be treated onto collagen sponge. The collagen sponge treated with interleukin-1 was contacted to the surface of mice carvarias through mice scalp incision, was implanted to 5 mice (5-week-male, ICR strain) in the test group and the control group, respectively, and was sutured. 7 days later, the mice were sacrificed to obtain calvarias. The test group was intraperitoneally injected with the dose of 0.2 mg of the compound obtained in Example 8 per one mouse from the next day of surgery to the day before the sacrifice. The control group was intraperitoneally injected with 100 μl of DMSO. After 7 days, the mice were sacrificed, and the extracted calvarias were washed 3-4 times with phosphate-buffered-saline solution and fixed in 4% paraformaldehyde for 24 hrs. Micro-computed tomography scan (SMX-90CT; Shimadzu, Japan) was performed for the fixed mice calvarias and 3-dimensional image thereof was obtained. The result is given in FIG. 3a.

Further, bone mineral content (BMC) was measured by using TRI 3D-BON (RATOC system Engineering Co., Tokyo, Japan) based on the 3-dimensional image (see Volume Graphics, VG studio Max 1.2.1). The result is given in FIG. 3b.

Figure 3A:
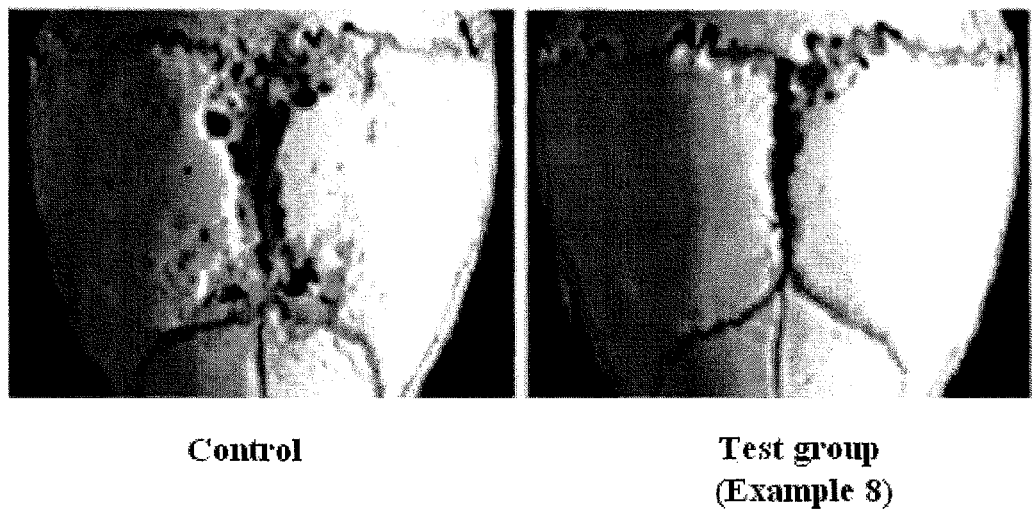
FIG. 3a: a 3-dimensional image of micro-computed tomography scanning, which is conducted to investigate the effect of the compound (Example 8) according the present invention on bone loss induced by interleukin-1 in vivo.
Figure 3B:
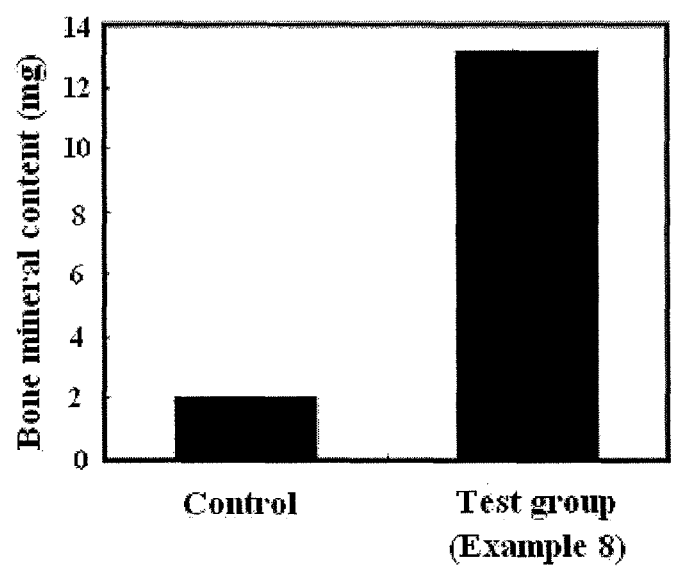

As shown in FIGS. 3a and 3b, it has been confirmed that bone loss in calvarias was suppressed in the test group treated with the amide compound of the present invention compared to the control group treated with vehicle, and the whole BMC is increased.

Histological studies were conducted in order to investigate the number of osteoclastic cells directly relating to bone loss. Specifically, the calvarias were decalcificated (solution was replaced every 2-3 days) with 12% EDTA (pH 7.2-7.4) for 14 days and embedded in paraffin. TRAP staining (Sigma-Aldrich) was performed on the embedded whole calvarias. The result is given in FIG. 3c.

In addition, the whole area of osteoclast which is red-stained, that is, TRAP-positive was shown in graph by using image J program. The result is given in FIG. 3d.

Figure 3C:
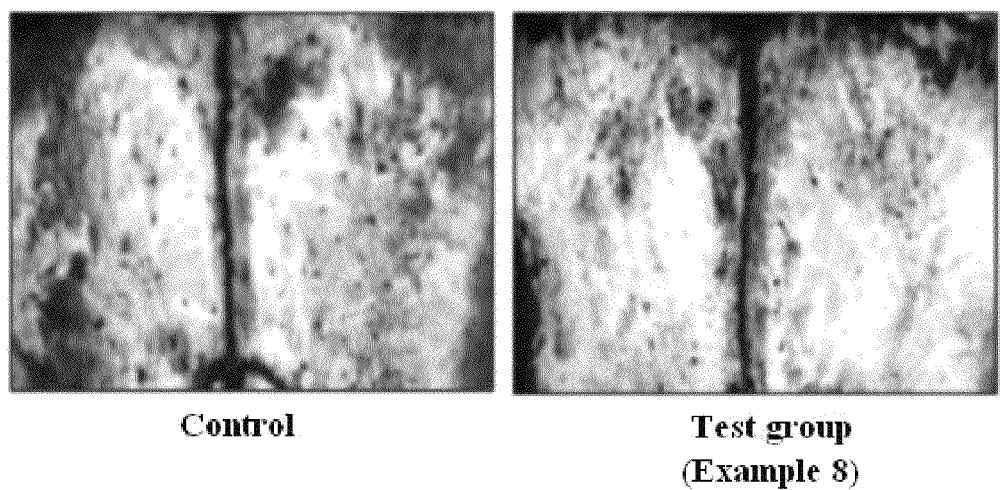
FIG. 3c: a photograph showing the result of TRAP dying the whole calvarias, which is taken to investigate the effect of the compound (Example 8) according the present invention on bone loss induced by interleukin-1 in vivo.
Figure 3D:
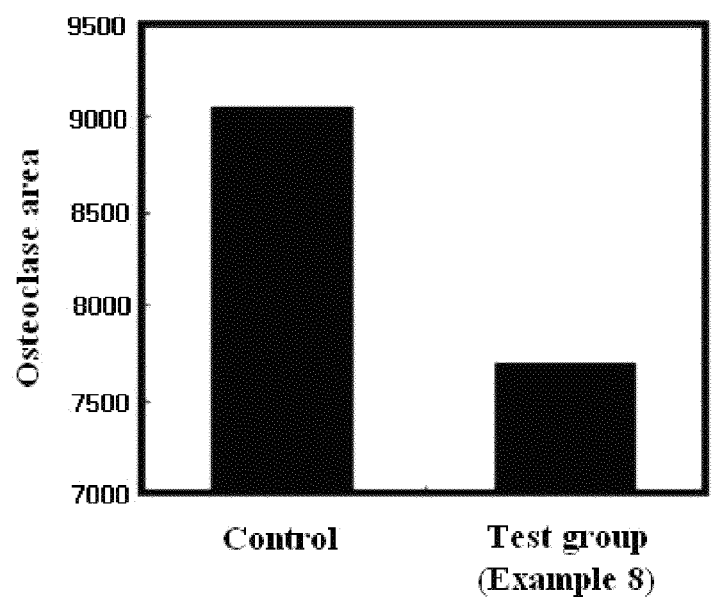
FIG. 3d: the result of evaluating the area occupied by osteoclast based on the image of FIG. 3c.

As shown in FIGS. 3c and 3d, it has been found that osteoclast leading to bone loss was remarkably reduced in the test group treated with the amide compound of the present invention compared to the control group treated with vehicle.

The procedure of the Experimental Example 3 was repeated except for using the compound obtained in Example 94 instead of the compound obtained in Example 8, to examine the effect on mice calvarias loss inhibition. The result is given in FIG. 4a.

Figure 4A:
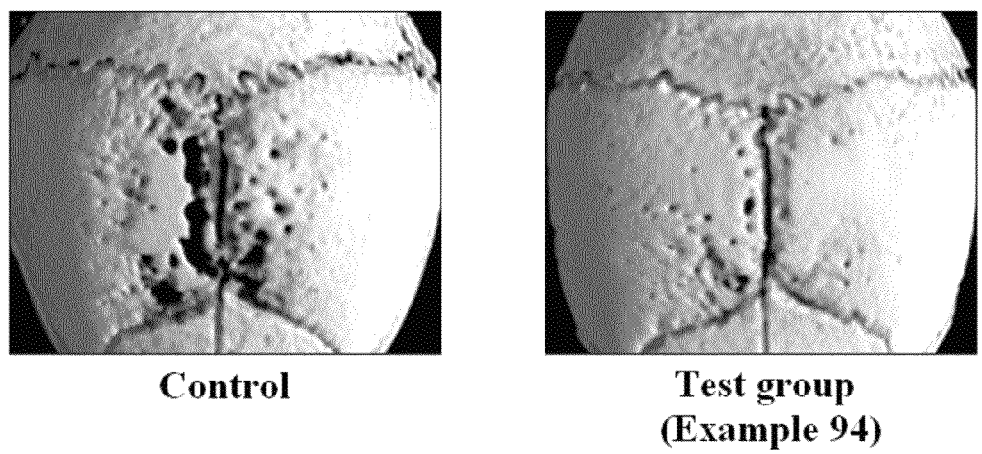
FIG. 4a: a 3-dimensional image of micro-computed tomography scanning, which is conducted to investigate the effect of the compound (Example 94) according to the present invention on bone loss induced by interleukin-1 in vivo.

As shown in FIG. 4a, it has been confirmed that bone loss in calvarias was suppressed in the test group treated with the amide compound of the present invention compared to the control group treated with vehicle.

Histological studies were conducted in order to investigate the number of osteoclastic cells directly relating to bone loss. Specifically, the calvarias were decalcificated (solution was replaced every 2-3 days) with 12% EDTA (pH 7.2-7.4) for 14 days and embedded in paraffin.

H-E (Hematotoxin-eosin) and TRAP staining (Sigma-Aldrich) were performed on the embedded whole calvarias. The results are given in FIGS. 4b and 4c, respectively. In addition, the whole area of osteoclast of the test and control group was shown in graph by using image J program. The result is given in FIG. 4d.

Figure 4B:
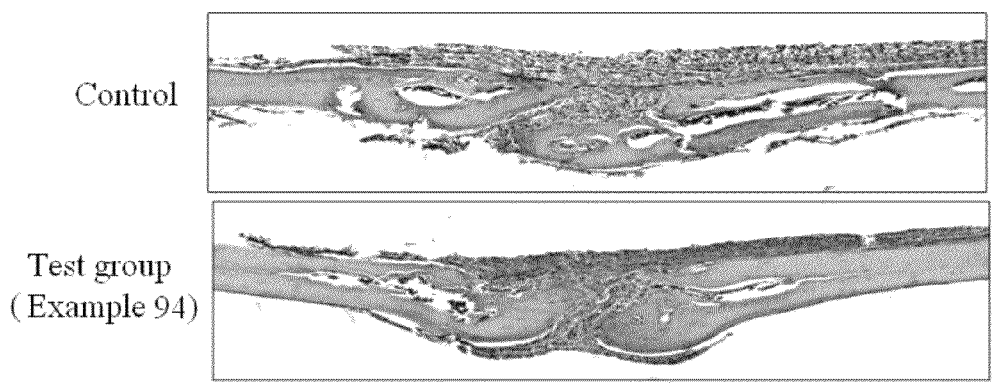
FIG. 4b: photograph showing the TRAP staining results of the whole calvarias to investigate the effect of the compound (Example 94) according to the present invention on bone loss induced by interleukin-1 in vivo, respectively.
Figure 4C:
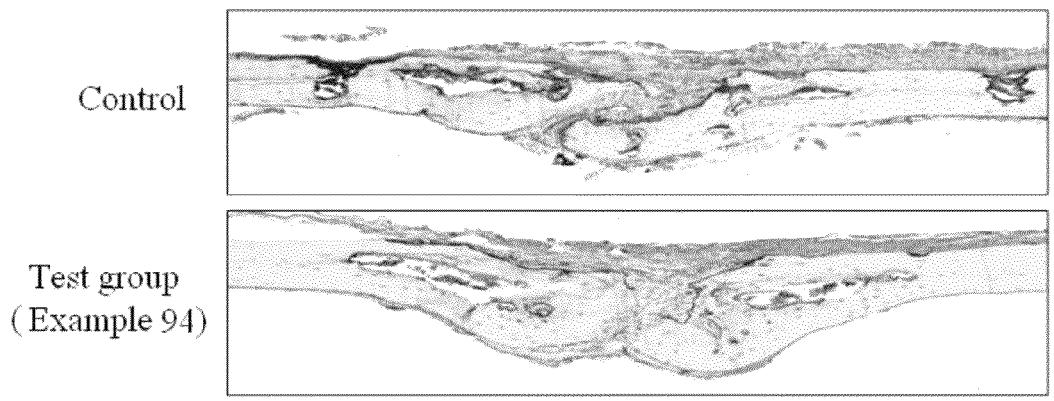
FIG. 4c: photograph showing the H-E staining results of the whole calvarias to investigate the effect of the compound (Example 94) according to the present invention on bone loss induced by interleukin-1 in vivo, respectively.
Figure 4D:
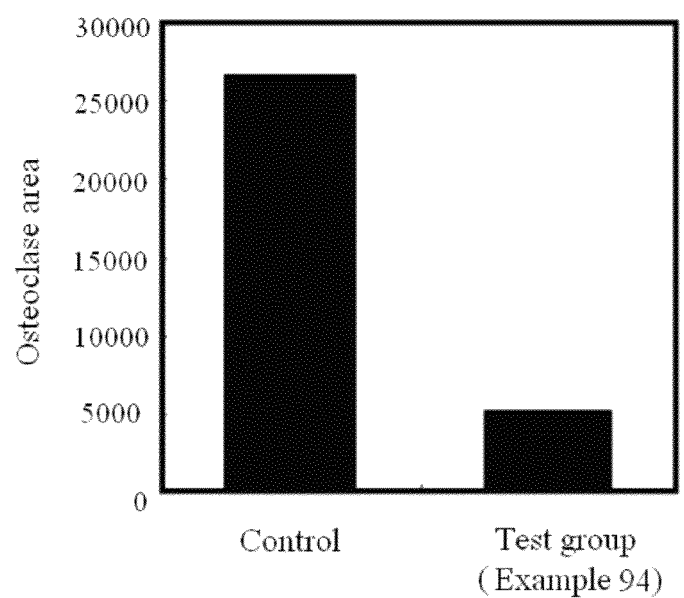
FIG. 4d: the result of evaluating the area occupied by osteoclast based on the image of FIG. 4b.

As shown in FIGS. 4b to 4d, it has been found that osteoclast leading to bone loss was remarkably reduced in the test group treated with the amide compound of the present invention compared to the control group treated with vehicle.

Experimental Example 4

Effect on Bone Formation in Case of Rats Calvarias Loss

To investigate the effect of the amide compound according to the present invention on bone formation, bone formation ability of the said compound in the rats calvarias loss site was examined in vivo by using the compounds obtained in Example 8 and 27.

Specifically, the hole of the diameter of 8 mm was made in calavarias of rats by using trephine bur, and the collagen sponge prepared in Experimental Example 3 treated with 0.2 mg of the compound obtained in Example 8 in 15 μl of DMSO was placed at the site of loss. As a control group, the collagen sponge treated with only 100 μl of DMSO was treated at the site of loss. After 6 days from the suture of the calvarias scalp, the rats were sacrificed to obtain calvarias. Micro-computed tomography scan (SMX-90CT; Shimadzu, Japan) was performed and 3-dimensional image thereof was obtained. The result is given in FIG. 5a.

Further, bone mineral content (BMC) of the test and control group was measured by using TRI 3D-BON (RATOC system Engineering Co., Tokyo, JP) based on the 3-dimensional image (see, *Volume Graphics*, VG studio Max 1.2.1). The result is given in FIG. 5b.

Figure 5A:
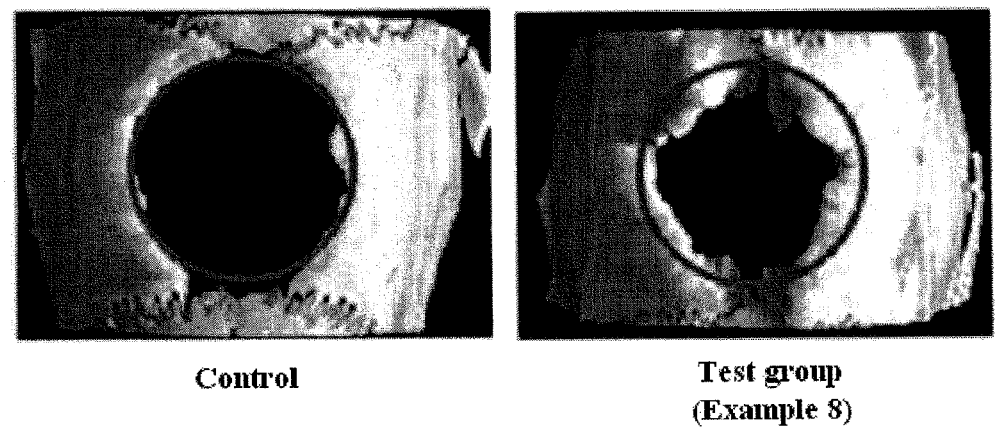
FIG. 5a: a 3-dimensional image of micro-computed tomography scanning, which is conducted to investigate the effect of the compound (Example 8) according the present invention on bone formation in the brain of rats in vivo.
Figure 5B:
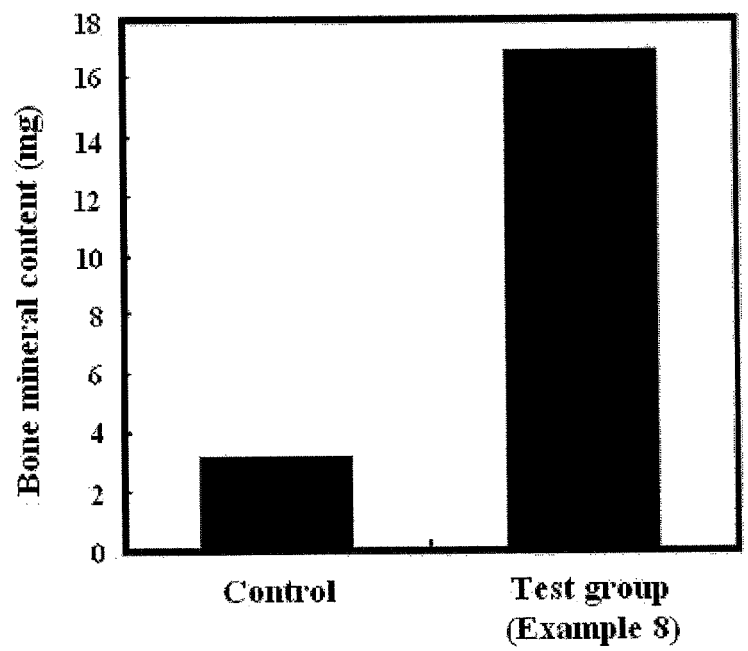

As shown in FIGS. 5a and 5b, it has been found that BMC, (that is, bone content) in the rats treated with the amide compound of the present invention was unexpectedly increased compared to the control group. From this result, it is confirmed that the amide compound of the present invention has an excellent ability of bone formation.

The procedure of the Experimental Example 4 was repeated except for using 0.2 mg or 0.5 mg of the compound obtained in Example 94 instead of 0.2 mg of the compound obtained in Example 8, to examine the effect on bone formation in case of Rats Calvarias Loss. The result is given in FIG. 6a.

Further, bone mineral content (BMC) of the test and control group was measured by using TRI 3D-BON (RATOC system Engineering Co., Tokyo, JP) based on the 3-dimensional image. The result is given in FIG. 6b.

Figure 6A:
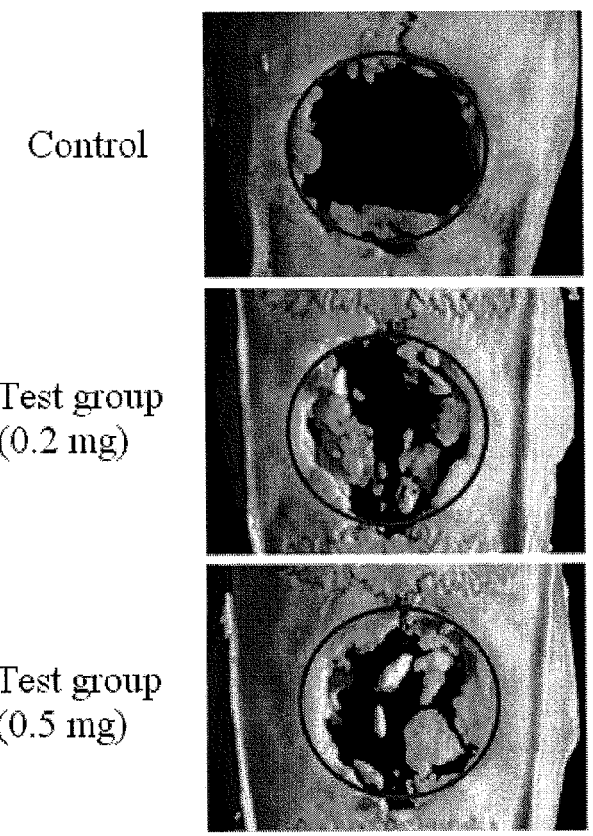
FIG. 6a: a 3-dimensional image of micro-computed tomography scanning, which is conducted to investigate the effect of the compound (Example 94) according the present invention on bone formation in the brain of rats in vivo.
Figure 6B:
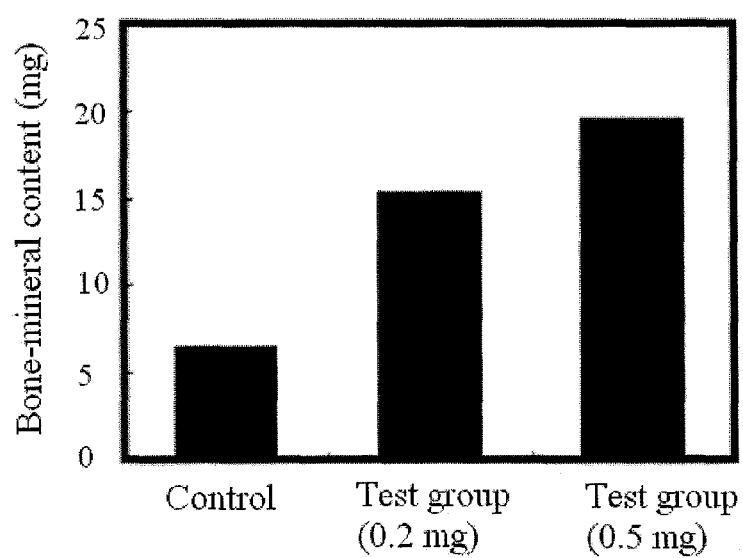

As shown in FIGS. 6a and 6b, it has been found that BMC (that is, bone content) in the rats treated with the amide compound of the present invention was unexpectedly increased compared to the control group. From this result, it is confirmed that the amide compound of the present invention has an excellent ability of bone formation.

While the invention has been described with respect to the above specific embodiments, it should be recognized that various modifications and changes may be made to the invention by those skilled in the art which also fall within the scope of the invention as defined by the appended claims.

What is claimed is:

1. An amide compound of formula (I) or a pharmaceutically acceptable salt thereof:

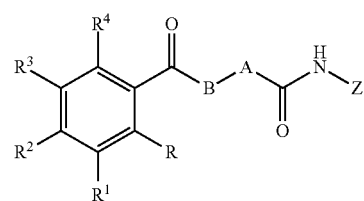

(I)

wherein,
A is

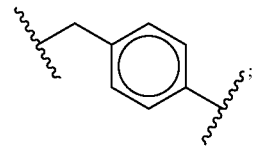

B is NH and R is selected from the group consisting of H, halogen, $C_1$-$C_6$ alkyl, $C_1$-$C_6$ alkoxy, aryl, substituted aryl, heteroaryl and substituted heteroaryl, or B and R are fused together to form an isoindolin-1-one ring;

$R^1$ to $R^4$ are each independently selected from the group consisting of H, halogen, $C_1$-$C_6$ alkyl, $C_1$-$C_6$ alkoxy, aryl, substituted aryl, heteroaryl and substituted heteroaryl, provided that at least one of $R^1$ and $R^2$ is not hydrogen, when B and R are fused together to form an isoindolin-1-one ring, and at least one of R and $R^1$ is $C_1$-$C_6$ alkyl, when B is NH;

Z is

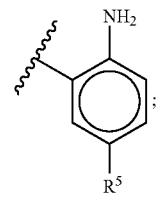

and
$R^5$ is H or 2-thiophenyl.

2. The compound of claim 1, which is the compound of formula (i) or (ii):

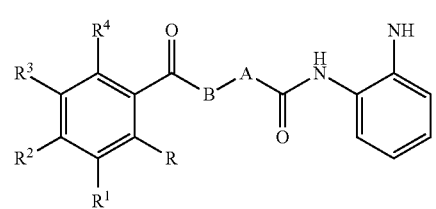

(i)

wherein A is

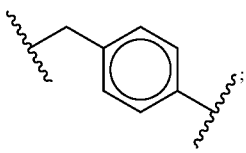

and B, R and $R^1$ to $R^4$ are as defined in claim 1.

3. The compound of claim 1, which is the compound of formula (iii) or (iv):

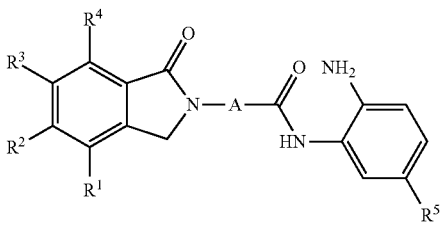

(iv)

wherein A is

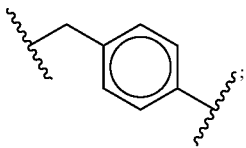

and B, R and $R^1$ to $R^5$ are as defined in claim 1.

4. The compound of claim 3, which is the compound of formula (iv):

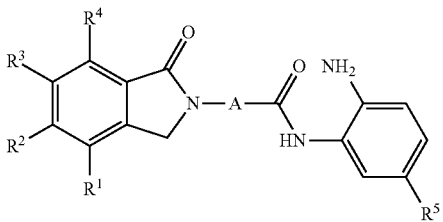

(iv)

wherein A is

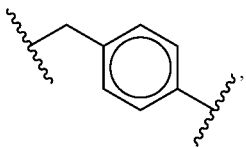

and $R^5$ is H.

5. The compound of claim 1, which is selected from the group consisting of:

N-(2-aminophenyl)-4-((4-bromo-5,6-dimethoxy-1-oxoisoindolin-2-yl)methyl)benzamide;
N-(2-aminophenyl)-4-((5,6-dimethoxy-1-oxo-4-phenylisoindolin-2-yl)methyl)benzamide;
N-(2-aminophenyl)-4-((5,6-dimethoxy-4-(3,5-dimethylphenyl)-1-oxoisoindolin-2-yl)methyl)benzamide;
N-(2-aminophenyl)-4-((5,6-dimethoxy-1-oxo-4-(pyridin-3-yl)isoindolin-2-yl)methyl)benzamide;
N-(2-aminophenyl)-4-((5,6-dimethoxy-4-(4-methoxyphenyl)-1-oxoisoindolin-2-yl)methyl)benzamide;
N-(2-aminophenyl)-4-((4-(4-(trifluoromethyl)phenyl)-5,6-dimethoxy-1-oxoisoindolin-2-yl)methyl)benzamide;
N-(2-aminophenyl)-4-((5,6-dimethoxy-4-(3,4-dimethoxyphenyl)-1-oxoisoindolin-2-yl)methyl)benzamide;
N-(2-aminophenyl)-4-((5,6-dimethoxy-1-oxo-4-(pyrimidin-5-yl)isoindolin-2-yl)methyl)benzamide;
N-(2-aminophenyl)-4-((4-bromo-1-oxoisoindolin-2-yl)methyl)benzamide;
N-(2-aminophenyl)-4-((1-oxo-4-(pyrimidin-5-yl)isoindolin-2-yl)methyl)benzamide;
N-(2-aminophenyl)-4-((1-oxo-4-phenylisoindolin-2-yl)methyl)benzamide;
N-(2-aminophenyl)-4-((4-(3,5-dimethylphenyl)-1-oxoisoindolin-2-yl)methyl)benzamide;
N-(2-aminophenyl)-4-((4-(4-trifluoromethyl)phenyl)-1-oxoisoindolin-2-yl)methyl)benzamide;
N-(2-aminophenyl)-4-((1-oxo-4-(pyridin-3-yl)isoindolin-2-yl)methyl)benzamide;
N-(2-aminophenyl)-4-((4-(4-methoxyphenyl)-1-oxoisoindolin-2-yl)methyl)benzamide;
N-(2-aminophenyl)-4-((4-(3,4-dimethoxyphenyl)-1-oxoisoindolin-2-yl)methyl)benzamide;
N-(2-aminophenyl)-4-((4-(3,5-difluorophenyl)-1-oxoisoindolin-2-yl)methyl)benzamide;
N-(2-aminophenyl)-4-((4-(3-aminophenyl)-1-oxoisoindolin-2-yl)methyl)benzamide;
N-(2-aminophenyl)-4-((4-(benzo[d][1,3]dioxol-6-yl)-1-oxoisoindolin-2-yl)methyl)benzamide;
N-(2-aminophenyl)-4-[4-(4-cyanophenyl)-1-oxo-2,3-dihydro-1H-isoindol-2-yl]methylbenzamide;
N-(2-aminophenyl)-4-((4-(naphthalen-2-yl)-1-oxoisoindolin-2-yl)methyl)benzamide;
N-(2-aminophenyl)-4-((4-(6-methoxypyridin-3-yl)-1-oxoisoindolin-2-yl)methyl)benzamide;
N-(2-aminophenyl)-4-[4-(3-acetamidophenyl)-1-oxo-2,3-dihydro-1H-isoindol-2-yl]methylbenzamide;
N-(2-aminophenyl)-4-((4-(3-fluoro-4-methoxyphenyl)-1-oxoisoindolin-2-yl)methyl)benzamide;
N-(2-aminophenyl)-4-[1-oxo-4-(4-phenylphenyl)-2,3-dihydro-1H-isoindol-2-yl]methylbenzamide;
3-[2-(4-[(2-aminophenyl)carbamoyl]phenylmethyl)-1-oxo-2,3-dihydro-1H-isoindol-4-yl]benzamide;
N-(2-aminophenyl)-4-((4-(3-fluoro-4-methylphenyl)-1-oxoisoindolin-2-yl)methyl)benzamide;
4-((4-(4-tert-butylphenyl)-1-oxoisoindolin-2-yl)methyl)-N-(2-aminophenyl)benzamide;
N-(2-aminophenyl)-4-((1-oxo-4-(4-phenoxyphenyl)isoindolin-2-yl)methyl)benzamide;
N-(2-aminophenyl)-4-((4-(4-fluorophenyl)-1-oxoisoindolin-2-yl)methyl)benzamide;
N-(2-amino-5-(thiophen-2-yl)phenyl)-4-((4-bromo-1-oxoisoindolin-2-yl)methyl)benzamide;
N-(2-amino-5-(thiophen-2-yl)phenyl)-4-((1-oxo-4-(pyrimidin-5-yl)isoindolin-2-yl)methyl)benzamide;
N-(2-amino-5-(thiophen-2-yl)phenyl)-6-(1-oxo-4-(pyrimidin-5-yl)isoindolin-2-yl)hexanamide;
N-(2-amino-5-(thiophen-2-yl)phenyl)-4-((5,6-dimethoxy-1-oxo-4-(pyridin-3-yl)isoindolin-2-yl)methyl)benzamide;

N-(2-aminophenyl)-4-((5-bromo-1-oxoisoindolin-2-yl)methyl)benzamide;
N-(2-aminophenyl)-4-((1-oxo-5-phenylisoindolin-2-yl)methyl)benzamide;
N-(2-aminophenyl)-4-((1-oxo-5-(pyrimidin-5-yl)isoindolin-2-yl)methyl)benzamide;
N-(2-aminophenyl)-4-((5-(4-(trifluoromethyl)phenyl)-1-oxoisoindolin-2-yl)methyl)benzamide;
N-(2-aminophenyl)-4-((5-(3,5-difluorophenyl)-1-oxoisoindolin-2-yl)methyl)benzamide;
N-(2-aminophenyl)-4-((1-oxo-5-(pyridin-3-yl)isoindolin-2-yl)methyl)benzamide;
N-(2-aminophenyl)-4-((5-(3,5-dimethylphenyl)-1-oxoisoindolin-2-yl)methyl)benzamide;
N-(2-aminophenyl)-4-((5-(4-methoxyphenyl)-1-oxoisoindolin-2-yl)methyl)benzamide;
N-(2-aminophenyl)-4-((5-(3,4-dimethoxyphenyl)-1-oxoisoindolin-2-yl)methyl)benzamide;
N-(2-aminophenyl)-4-[5-(4-cyanophenyl)-1-oxo-2,3-dihydro-1H-isoindol-2-yl]methylbenzamide;
N-(2-aminophenyl)-4-((5-(benzo[d][1,3]dioxol-6-yl)-1-oxoisoindolin-2-yl)methyl)benzamide;
N-(2-aminophenyl)-4-((5-(naphthalen-2-yl)-1-oxoisoindolin-2-yl)methyl)benzamide;
N-(2-aminophenyl)-4-((3-bromo-2-methylbenzamido)methyl)benzamide;
N-(2-aminophenyl)-4-((2-methyl-3-phenyl-benzamido)methyl)benzamide;
N-(2-aminophenyl)-4-((2-methyl-3-(5-pyrimidinyl)benzamido)methyl)benzamide;
N-(2-aminophenyl)-4-((2-methyl-3-(3-pyridinyl)benzamido)methyl)benzamide;
N-(2-aminophenyl)-4-((2-methyl-3-(3-aminophenyl)benzmido)methyl)benzamide;
N-(2-aminophenyl)-4-((3-bromo-4,5-dimethoxy-2-methylbenzamido)methyl)benzamide;
N-(2-aminophenyl)-4-((2-methyl-3-phenyl-4,5-dimethoxy-benzamido)methyl)benzamide;
N-(2-aminophenyl)-4-((2-methyl-4,5-dimethoxy-3-(5-pyrimidinyl)-benzamido)methyl)benzamide;
N-(2-aminophenyl)-4-((2-methyl-3-(3-pyridinyl)-4,5-dimethoxy-benzamido)methyl)benzamide;
N-(2-aminophenyl)-4-((3-(3-aminophenyl)-4,5-dimethoxy-2-methyl-benzamido)methyl)benzamide;
N-(2-aminophenyl)-4-((2-methyl-3-(4-trifluoromethylphenyl)-4,5-dimethoxy-benzamido)methyl)benzamide;
N-(2-aminophenyl)-4-((2-methyl-3-(3,5-difluorophenyl)-4,5-dimethoxy-benzamido)methyl)benzamide.

6. A pharmaceutical composition comprising the compound of claim 1 and a pharmaceutically acceptable carrier.

7. A method for treating a bone disorder comprising administering the compound of claim 1 into a subject in need thereof, wherein the bone disorder is selected from the group consisting of osteoporosis, osteodystrophy, bone fracture, periodontal disease, Paget's disease, bone metastasis, and rheumatoid arthritis.

* * * * *